US008404730B2

(12) United States Patent
Park et al.

(10) Patent No.: US 8,404,730 B2
(45) Date of Patent: Mar. 26, 2013

(54) 3-SUBSTITUTED PROPANAMINE COMPOUNDS

(75) Inventors: Chun-Eung Park, Seoul (KR); Kyung-Hyun Min, Daejeon (KR); Yong-Je Shin, Daejeon (KR); Yu-Jin Shin, Daejeon (KR); Hae-Jeong Yoon, Daejeon (KR); Won Kim, Daejeon (KR); Eun-Ju Ryu, Daejeon (KR); Coo-Min Chung, Daejeon (KR); Hui-Ho Kim, Daejeon (KR)

(73) Assignee: SK Biopharmaceuticals Co., Ltd., Seoul (KR)

( * ) Notice: Subject to any disclaimer, the term of this patent is extended or adjusted under 35 U.S.C. 154(b) by 5 days.

(21) Appl. No.: 13/276,804

(22) Filed: Oct. 19, 2011

(65) Prior Publication Data

US 2012/0046312 A1    Feb. 23, 2012

Related U.S. Application Data

(62) Division of application No. 12/477,263, filed on Jun. 3, 2009, now Pat. No. 8,101,642.

(60) Provisional application No. 61/059,109, filed on Jun. 5, 2008.

(51) Int. Cl.
*A61K 31/41* (2006.01)
*C07D 257/04* (2006.01)

(52) U.S. Cl. .................. 514/381; 548/250; 548/254

(58) Field of Classification Search ............ 548/250, 548/254; 514/381
See application file for complete search history.

(56) References Cited

U.S. PATENT DOCUMENTS

| 4,710,502 | A | 12/1987 | Wright, Jr. et al. | |
| 7,037,932 | B2 | 5/2006 | Gallagher et al. | |
| 8,101,642 | B2 * | 1/2012 | Park et al. | 514/381 |
| 2007/0123535 | A1 | 5/2007 | Greenhouse et al. | |

FOREIGN PATENT DOCUMENTS

| WO | 9723480 | 7/1997 |
| WO | 99/43656 | 9/1999 |
| WO | 2004043931 | 5/2004 |
| WO | 2004072071 | 8/2004 |
| WO | 2005118539 | 12/2005 |
| WO | 2007/006132 | 1/2007 |
| WO | 2008/140197 | 11/2008 |
| WO | 2010/044585 | 4/2010 |

OTHER PUBLICATIONS

The International Search Report and Written Opinion by the International Search Authority, issued on Jan. 14, 2010, in the PCT application No. PCT/KR2009/003041.
Berge et al., "Pharmaceutical salts," Journal of Pharmaceutical Sciences, vol. 66, Issue 1, pp. 1-19, Jan. 1977.

Gu et al., "Stable expression of biogenic amine transporters reveals differences in inhibitor sensitivity, kinetics, and ion dependence," Mar. 11, 1994 The Journal of Biological Chemistry, vol. 269, 7124-7130.
Galli et al., "Sodium-dependent norepinephrine-induced currents in norepinephrine-transporter-transfected HEK-293 cells blocked by cocaine and antidepressants," J Exp Biol. Oct. 1995;198(Pt 10):2197-212.
Pristupa et al., "Pharmacological heterogeneity of the cloned and native human dopamine transporter: disassociation of [3H]WIN 35,428 and [3H]GBR 12,935 binding," Mol Pharmacol. Jan. 1994;45(1):125-35.
The extended European Search Report by the European Patent Office, issued on Mar. 27, 2012, in the corresponding European patent application No. 09758543.4.
D1: Ilarionov et al., "Relationship between antireserpine and aphrodisiac effects. Pharmacologic aspects," Farmatsiya (Sofia, Bulgaria), 40(3), 32-8 Coden: FMTYA2; ISSN: 0428-0296, 1990.
D2: Avramova et al., "Synthesis and Pharmacologic assessment of carbamic and carbonic acid esters with 1-aryl-3-dimethylamino-1-propanols. Part 3," Pharmazie, Coden: Pharat; ISSN: 0031-7144, vol. 38, No. 7, Jul. 1983, pp. 443-444.
D3: Avramova et al., "Synthesis and Pharmacologic study of the esters of carbamic and carbonic acids with 1-phenyl-2, 2-dimethyl-3-dialkylamino-1-propanols. Part 2," Pharmazie, Coden: Pharat; ISSN: 0031-7144, vol. 38, No. 6, Jun. 1981, pp. 410-412.
D4: Spasov et al., "Stereochemistry of diastereomeric 3-(dialkylamino) propanols and O-substituted derivatives," Journal Fuer Praktische Chemie (Leipzig), Coden: Jpceao; ISSN: 0021-8383, vol. 323, No. 5, 1981, pp. 793-800.
D5: Matsui et al., "Preparation of 3-(5-isoxaxolyl)- or 3-phenylpropylaine derivatives as central muscle relaxants," retrieved from STN, database accession No. 1999:566027; WO 99/43656 A1 (Maruho Kabushikikaisha, Japan) Sep. 2, 1999.
D6: Osadebe et al., "Determination and correlation of the reversed-phase thin-layer chromatographic parameter (RM) of a series of 3-(4-substituted-1-piperazinyl)-1-substituted-1-phenyl propanol derivatives with their LD50 values," Bollettino Chimico Farmaceutico, 143(6), 253-260 Coden: Bcfaai; ISSN: 0006-6648, 2004.
D10: Database Registry (Online), Chemical Abstracts Service, Columbus, Ohio, U.S.; Jun. 8, 2008, XP 002669691, database accession No. 1026221-94-2.
D11: Database Registry (Online), Chemical Abstracts Service, Columbus, Ohio, U.S.; Jun. 8, 2008, XP 002669692, database accession No. 1026357-55-0.
D12: Database Registry (Online), Chemical Abstracts Service, Columbus, Ohio, U.S.; Jun. 12, 2008, XP 002669693, database accession No. 1027550-70-4.

*Primary Examiner* — Golam M M Shameem

(57) ABSTRACT

Racemic or enantiomerically enriched 3-substituted propanamine compounds represented by the following structural formula (I):

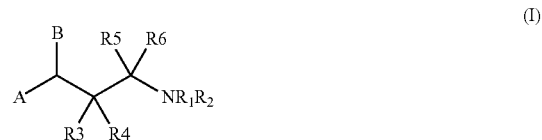

or a pharmaceutically acceptable salt thereof are disclosed. Pharmaceutical compositions containing the subject compounds are also disclosed. The subject compounds are useful for the treatment of diseases of the central nervous system, such as depression, anxiety and pain disorders.

3 Claims, No Drawings

3-SUBSTITUTED PROPANAMINE COMPOUNDS

RELATED APPLICATIONS

This application claims priority from U.S. Provisional Application Ser. No. 61/059,109, filed Jun. 5, 2008, the disclosure of which is incorporated herein in its entirety.

FIELD OF THE INVENTION

The present invention relates, in general, to racemic or enantiomerically enriched novel 3-substituted propanamine derivatives and pharmaceutically useful salts thereof, a pharmaceutical composition comprising an effective amount of racemic or enantiomerically enriched novel 3-substituted propanamine derivatives as monoamine neurotransmitter re-uptake inhibitors to treat central nervous system diseases and a method of treating central nervous system diseases in a mammal. More particularly, the present invention relates to racemic or enantiomerically enriched novel 3-substituted propanamine derivatives having various azole moieties and pharmaceutically useful salts thereof, useful to treat the diseases of the central nervous system such as depression, anxiety and pain disorder.

BACKGROUND OF THE INVENTION

The three biogenic amines, serotonin, norepinephrein and dopamine are most closely linked to CNS disorders such as depression. The majority of antidepressants in current use selectively inhibit the reuptake of serotonin and/or norepinephrine. Although a strong dopamine re-uptake inhibiting activity is considered with the risk of undesirable central stimulation effects, many reports have disclosed that the triple monoamine neurotransmitter, i.e serotonin, norepinephrine and dopamine, re-uptake inhibitors are useful for the treatment of CNS disorders such as depression, anxiety, attention deficit hyperactivity disorder, obesity, drug addiction and pain disorder. For example, International Patent Application No. WO 2004/072071 discloses the novel 8-aza-bicyclo[3,2,1]octane derivatives useful as monoamine neurotransmitter re-uptake inhibitors.

3-substituted propanamine compounds are effectively used for controlling various central nervous system (CNS) disorders. For example, International Patent Application No. WO 04/43931 discloses 3-substituted propanamine derivatives that are suitable for treating anxiety, depression, sleep disorder. Similarly heteroaryloxy 3-substituted propanamine is disclosed in U.S. Pat. Nos. 7,037,932 and 3-Amino-1-arylpropyl indole derivatives are disclosed in International Patent Application No. WO 05/118539 as monoamine reuptake inhibitor for the treatment of various central nervous system disorders. Active research and development efforts have continued to be directed to the application of 3-substituted propanamine compounds for the treatment of CNS disorders.

SUMMARY OF THE INVENTION

A principal object of the present invention is to provide 3-substituted propanamine derivatives, represented by the following structural formula (I):

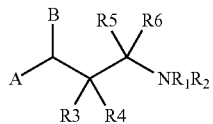

or any of its isomers or pharmaceutically acceptable salts thereof wherein

A is selected from the group consisting of phenyl, naphtyl, benzothiophenyl, pyridyl, quinolyl, isoquinolyl, benzodioxolyl, benzodioxinyl, indolyl, fluorenyl and benzofuranyl, which can be substituted with one or more identical or different substituents selected from the group consisting of hydrogen, halogen, straight or branched $C_{1-4}$ alkyl, straight or branched $C_{1-3}$ alkoxy, phenyl, phenyloxy, nitro, cyano, trifluoromethyl, trifluoromethoxy, methane sulfonyl and thienyl;

$R_1$ and $R_2$ are same or different and independently selected from the group consisting of hydrogen, straight or branched $C_{1-4}$ alkyl and substituted or unsubstituted phenyl $C_{1-4}$ alkyl; or $R_1$ and $R_2$ are fused with nitrogen atom to form cyclic group which has 4 to 7 carbon atoms;

$R_3$, $R_4$, $R_5$ and $R_6$ are same or different and independently selected from the group consisting of hydrogen, straight or branched $C_{1-4}$ alkyl and substituted or unsubstituted phenyl;

B is selected from the group consisting of O-carbamoyl, straight or branched $C_{1-4}$ alkoxy, carbonate and an azole selected from the group consisting of imidazole, triazole, benzotriazole, tetrazole, 5-methyl tetrazole and 5-phenyl tetrazole which are linked by nitrogen as represented by the following structural formula (II):

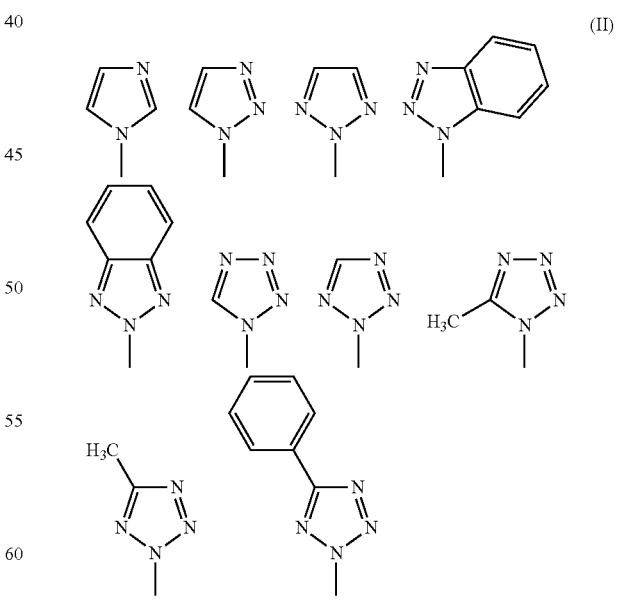

More specifically, the present 3-substituted propanamine compounds represented by the above formula (I) comprise racemic of enantiomerically enriched compounds represented by the following structural formula (III):

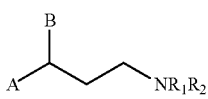
(III)

wherein A, B, $R_1$ and $R_2$ are as defined therein and each of $R_3$ through $R_6$ is hydrogen.

More specifically, the present 3-substituted propanamine compounds represented by the above formula (III) comprise any of its enantiomeric isomers represented by the following structural formula (IV) and (V):

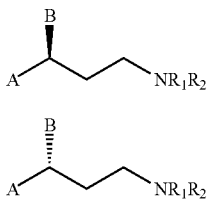
(IV)

(V)

wherein
A, B, $R_1$ and $R_2$ are as defined above.

More specifically, the present 3-substituted propanamine compounds represented by the above formula (I) comprise racemic of enantiomerically enriched compounds represented by the following structural formula (XI)

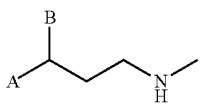
(XI)

wherein A, B are as defined therein, each of $R_3$ through $R_6$ is hydrogen and one of $R_1$ and $R_2$ is hydrogen and the other is methyl.

It is another object of the present invention to provide a pharmaceutical composition comprising an effective amount of racemic or enantiomerically enriched 3-substituted propanamine compounds represented by the above structural formula (I), in particular, the compounds represented by the above structural formula (III), (IV) and (V) for treating disorders of central nervous system such as depression, anxiety and pain disorder.

It is still another object of the present invention to provide a method of treating disorders of central nervous system such as depression, anxiety and pain disorder in a mammal by administering an effective amount of racemic or enantiomerically enriched 3-substituted propanamine compounds represented by the above structural formula (I), in particular, the compounds represented by the above structural formula (III), (IV) and (V) and a pharmaceutical acceptable carrier to a mammal in need thereof.

DETAILED DESCRIPTION OF THE INVENTION

In accordance with the present invention, the compound represented by the structural formula (I) and pharmaceutical acceptable salts thereof can be prepared by techniques and procedures readily available to one of ordinary skill in the art, for example by following the procedures as set forth in the following schemes. These schemes are not intended to limit the scope of the invention in any way. All substituents, unless otherwise indicated, are previously defined. The reagents and starting materials are readily available to one of ordinary skill in the art.

In accordance with the present invention, the compounds of this invention represented by the structural formula (I), (III), (IV) and (V) and pharmaceutically acceptable salts thereof can be prepared by the following steps starting from readily available starting materials represented by the following general formula (VI)

(VI)

wherein
A is selected from the group consisting of phenyl, naphtyl, benzothiophenyl, pyridyl, quinolyl, isoquinolyl, benzodioxolyl, benzodioxinyl, indolyl, fluorenyl and benzofuranyl, which can be substituted with one or more identical or different substituents selected from the group consisting of hydrogen, halogen, straight or branched chain alkyl of from 1 to 4 carbon atoms, straight or branched chain alkoxy of from 1 to 3 carbon atoms, phenyl, phenyloxy, nitro, cyano, trifluoromethyl, trifluoromethoxy, methanesulfonyl and thienyl;

The method for preparing the novel compounds of the general formula (III) will be described below in detail.

Initially, the starting material represented by the above general formula (VI) is reacted with readily available amine (VII) and paraformaldehyde $HNR_1R_2$ (VII)

wherein
$R_1$ and $R_2$ are same or different and independently selected from the group consisting of hydrogen, lower alkyl of from 1 to 4 carbon atoms, substituted or unsubstituted phenyl-$C_{1-4}$ alkyl or $R_1$ and $R_2$ are fused with nitrogen atom to form cyclic group which has 4 to 7 carbon atoms;
to synthesize 1,3-aminoketone compound represented by the general formula (VIII).

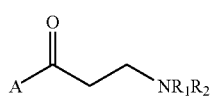
(VIII)

wherein
A, $R_1$ and $R_2$ are the same as defined above.

The compound of formula (VIII) is followed by the treatment with sodium borohydride in methanol to yield the corresponding 1,3-diaminoalchol compound represented by the general formula (IX).

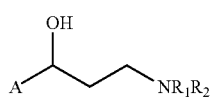
(IX)

The compound of formula (IX) is reacted with triphenylphosphine, diisopropyl azodicarboxylate and azole compounds such as imidazole, triazole, tetrazole, 5-methyltetrazole, 5-phenyltetrazole, benzotriazole represented by the structural formula (II) to give the compound represented by the general formula (III).

(III)

wherein

A and B are the same as defined above.

$R_1$ and $R_2$ are same and different and independently selected from the group consisting of hydrogen, lower alkyl of from 1 to 4 carbon atoms, substituted or unsubstituted phenyl-$C_{1-4}$ alkyl or $R_1$ and $R_2$ are fused to form cyclic group with nitrogen atom;

This procedure is summarized as set forth in Reaction Scheme I below.

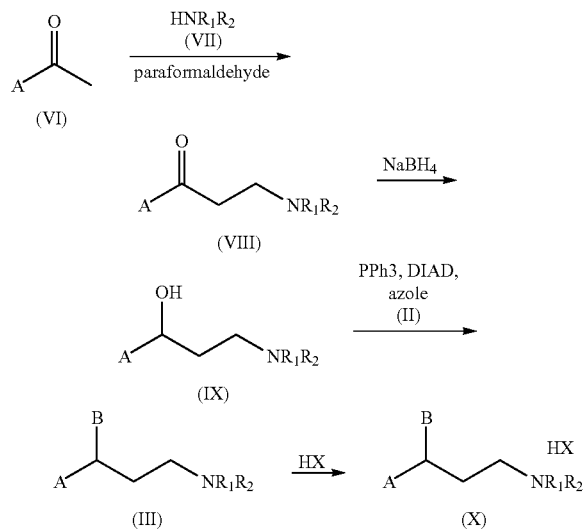

Reaction Scheme I

Details of the reaction condition described in reaction scheme I are as follows.

In the first step, the concentration of the starting material (VI) is about to 0.005 to 3 moles with paraformaldehyde ranging from about 3.0 to 5.0 equivalents, amine (VII) ranging from about 3.0 to 5.0 equivalents and aq. HCl. The reaction is carried out at temperature about 90☐. For the conversion of the compound (VIII) to the compound (IX), sodium borohydride ranging from about 1.0 to 2.5 equivalents is used in methanol. The resulting compound is treated with 1.5 equivalents of PPh3, diisopropyl azodicarboxylate and azole compound to give the compound (III).

Additionally, the compounds of formula (III) may be converted into pharmaceutically acceptable salts (X) by treating the compound (III) with acid as described in the reaction scheme I. In the reaction scheme I, HX represents an acid capable of forming a pharmacologically useful salt with the basic nitrogen atom. Specific examples of the anhydrous acid used for the preparation of the compound (X) from the compound (III) include hydrochloric acid, hydrobromic acid, sulfuric acid, phosphoric acid, acetic acid, benzoic acid, carbonic acid, citric acid, malonic acid, salicylic acid, malic acid, fumaric acid, oxalic acid, succinic acid, tartaric acid, lactic acid, gluconic acid, ascorbic acid, maleic acid, aspartic acid, camphorsulfonic acid, p-toluenesulfonic acid, benzene sulfonic acid, methane sulfonic acid, ethane sulfonic acid, hydroxymethane sulfonic acid and hydroxyethane sulfonic acid and the like. Additional acids can refer to "Pharmaceutical Salts", J. Pharm. Sci., 1977; 66(1): 1-19. This preparation is executed in a reaction media which can be exemplified by an ethereal solvent such as THF, an alcoholic solvent such as methanol, an ester solvent such as ethyl acetate, and aromatic solvent, and any compositional mixture thereof. An ethereal solvent is recommended as an addition solution, including ethyl ether, propyl ether, isopropyl ether, butyl ether, isobutyl ether. The concentration of the compound (III) is on the order of about 0.01 to 5 moles.

The methods for preparing the compounds of the general formula (III) in which $R_1$ is hydrogen and $R_2$ is methyl, i.e. the compounds of the general formula (XI), will be described below.

The compounds of general formula (III) wherein $R_1$ and $R_2$ are methyl is treated with ethyl chloroformate, sodium bicarbonate and potassium hydroxide to yield the monomethyl amine compound represented by the structural formula (XI).

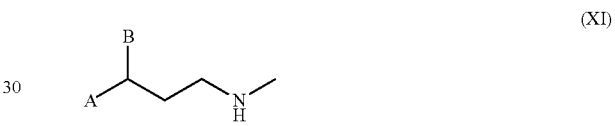

(XI)

Wherein

A and B are the same as defined above.

The compound of formula (XI) may be converted into pharmaceutically acceptable salt (XII) as described above.

This procedure of preparing the compounds of general formula (XI) and pharmaceutically acceptable salts thereof is summarized as set forth in Reaction Scheme II below.

Reaction Scheme II

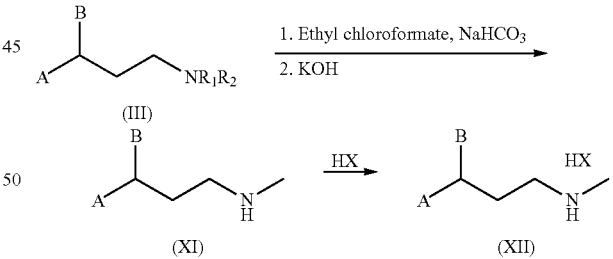

Details of the reaction condition described in reaction scheme II are as follows. For the conversion of compound (III) in which $R_1$ and $R_2$ are methyl, to the compound (XI), ethyl chloroformate ranging from 10 to 15 equivalents, sodium bicarbonate ranging from 20 to 25 equivalents and similar amount of potassium hydroxide are used at temperature about 100☐.

In reaction scheme II, HX represents an acid capable of forming a pharmacologically useful salt with the basic nitrogen atom as described above.

Enantiomeric isomers represented by the structural formula (IV) and (V) are obtained from racemic mixture (III) by means of chiral preparative Liquid Chromatography ("prep- LC"). The methods for preparing the general formula (IV) and (V) will be described below.

The racemic mixture (III) is dissolved in a small amount of isopropylalcohol and separated by chiral preparative Liquid Chromatography. Separation is performed by using a CHIRALPACK OD-H column (manufactured by Daicel Chemical Industries, Ltd.) as the Prep-LC column, at a column temperature of 25° C., with n-hexane/isopropylalcohol including 0.1% triethylamine (90:10) as the eluent. Enantiomeric isomers represented by the structural formula (IV) and (V) can be obtained in the ratio of 1:1 from the racemic mixture (III).

This procedure is summarized as set forth in reaction scheme III below.

Reaction Scheme III

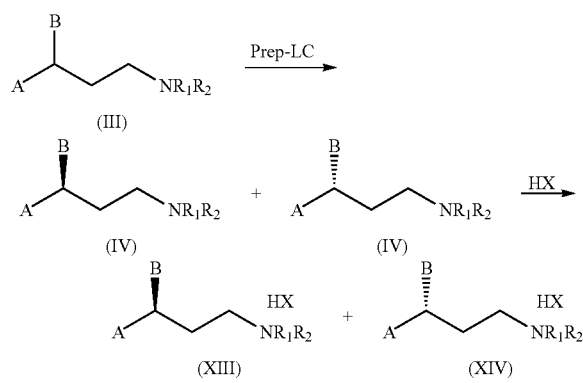

In reaction scheme III, HX represents an acid capable of forming a pharmacologically useful salt with the basic nitrogen atom as described above.

The compounds of formula (IV) and (V) may be converted into pharmaceutically acceptable salts (XIII) and (XIV) as described above.

The compounds prepared according to the above methods include the following compounds.
[3-(3,4-Dichloro-phenyl)-3-tetrazol-2-yl-propyl]-dimethyl-amine
[3-(3,4-Dichloro-phenyl)-3-tetrazol-2-yl-propyl]-methyl-amine
S-[3-(3,4-Dichloro-phenyl)-3-tetrazol-2-yl-propyl]-methyl-amine
[3-Benzotriazol-2-yl-3-(3,4-dichloro-phenyl)-propyl]-dimethyl-amine
Dimethyl-(3-naphthalen-2-yl-3-[1,2,3]triazol-2-yl-propyl)-amine
Dimethyl-(3-naphthalen-2-yl-3-tetrazol-2-yl-propyl)-amine
(3-Benzotriazol-2-yl-3-naphthalen-2-yl-propyl)-dimethyl-amine
Dimethyl-[3-(5-methyl-tetrazol-2-yl)-3-naphthalen-2-yl-propyl]-amine
[3-(6-Chloro-naphthalen-2-yl)-3-tetrazol-1-yl-propyl]-dimethyl-amine
Dimethyl-[3-(4-phenoxy-phenyl)-3-tetrazol-2-yl-propyl]-amine
Dimethyl-[3-(4-phenoxy-phenyl)-3-tetrazol-1-yl-propyl]-amine
[3-(6-Chloro-naphthalen-2-yl)-3-[1,2,3]triazol-2-yl-propyl]-dimethyl-amine
[3-(6-Chloro-naphthalen-2-yl)-3-[1,2,3]triazol-1-yl-propyl]-dimethyl-amine
[3-(6-Chloro-naphthalen-2-yl)-3-tetrazol-2-yl-propyl]-dimethyl-amine
[3-(4-Methoxy-phenyl)-3-[1,2,3]-triazol-2-yl-propyl]-dimethyl-amine
(3-Biphenyl-3-yl-3-tetrazol-2-yl-propyl)-dimethyl-amine
[3-(4-Benzyloxy-phenyl)-3-tetrazol-2-yl-propyl]-dimethyl-amine
(3-Biphenyl-4-yl-3-tetrazol-2-yl-propyl)-dimethyl-amine
Dimethyl-[3-naphthalen-2-yl-3-(5-phenyl-tetrazol-2-yl)-propyl]-amine
Dimethyl-[3-(6-methyl-naphthalen-2-yl)-3-tetrazol-2-yl-propyl]-amine
[3-(6-Methoxy-naphthalen-2-yl)-3-tetrazol-2-yl-propyl]-dimethyl-amine
[3-(6-Methoxy-naphthalen-2-yl)-3-[1,2,3]triazol-2-yl-propyl]-dimethyl-amine
[3-Benzotriazol-1-yl-3-(3,4-dichloro-phenyl)-propyl]-dimethyl-amine
2-[1-(3,4-Dichloro-phenyl)-3-pyrrolidin-1-yl-propyl]-2H-[1,2,3]triazole
[3-(3,4-Dichloro-phenyl)-3-[1,2,3]triazol-2-yl-propyl]-dimethyl-amine
[3-(3,4-Dichloro-phenyl)-3-tetrazol-2-yl-propyl]-diethyl-amine
2-[1-(3,4-Dichloro-phenyl)-3-pyrrolidin-1-yl-propyl]-2H-tetrazole
Dimethyl-(3-naphthalen-1-yl-3-tetrazol-2-yl-propyl)-amine
Dimethyl-(3-naphthalen-1-yl-3-[1,2,3]triazol-2-yl-propyl)-amine
[3-(3,4-Dichloro-phenyl)-3-(5-methyl-tetrazol-2-yl)-propyl]-dimethyl-amine
[3-(3,4-Dichloro-phenyl)-3-(5-phenyl-tetrazol-2-yl)-propyl]-dimethyl-amine
[3-(3,4-Difluoro-phenyl)-3-tetrazol-1-yl-propyl]-dimethyl-amine
[3-(3,4-Difluoro-phenyl)-3-tetrazol-2-yl-propyl]-dimethyl-amine
[3-(3,4-Difluoro-phenyl)-3-[1,2,3]triazol-1-yl-propyl]-dimethyl-amine
[3-(3,4-Difluoro-phenyl)-3-[1,2,3]triazol-2-yl-propyl]-dimethyl-amine
[3-(3,4-Dimethyl-phenyl)-3-[1,2,3]triazol-1-yl-propyl]-dimethyl-amine
[3-(3,4-Dimethyl-phenyl)-3-[1,2,3]triazol-2-yl-propyl]-dimethyl-amine
[3-(3,4-Dimethyl-phenyl)-3-tetrazol-1-yl-propyl]-dimethyl-amine
[3-(3,4-Dimethyl-phenyl)-3-tetrazol-2-yl-propyl]-dimethyl-amine
[3-(4-Chloro-phenyl)-3-tetrazol-1-yl-propyl]-dimethyl-amine
[3-(4-Chloro-phenyl)-3-tetrazol-2-yl-propyl]-dimethyl-amine
Dimethyl-(3-phenyl-3-[1,2,3]triazol-1-yl-propyl)-amine
Dimethyl-(3-phenyl-3-[1,2,3]triazol-2-yl-propyl)-amine
[3-(4-Chloro-phenyl)-3-[1,2,3]triazol-1-yl-propyl]-dimethyl-amine
[3-(4-Chloro-phenyl)-3-[1,2,3]triazol-2-yl-propyl]-dimethyl-amine
[3-(3,4-Dichloro-phenyl)-3-[1,2,3]triazol-2-yl-propyl]-dimethyl-amine
[3-(3,4-Dichloro-phenyl)-3-imidazol-1-yl-propyl]-dimethyl-amine
[3-(3-Methoxy-naphthalen-2-yl)-3-tetrazol-2-yl-propyl]-dimethyl-amine
[3-(3-Methoxy-naphthalen-2-yl)-3-(5-methyl-tetrazol-2-yl)-propyl]-dimethyl-amine

[3-(6-Fluoro-naphthalen-2-yl)-3-tetrazol-2-yl-propyl]-dimethyl-amine
[3-(6-Fluoro-naphthalen-2-yl)-3-(5-methyl-tetrazol-2-yl)-propyl]-dimethyl-amine
[3-(1,4-Dimethoxy-naphthalen-2-yl)-3-tetrazol-2-yl-propyl]-dimethyl-amine
[3-(1,4-Dimethoxy-naphthalen-2-yl)-3-(5-methyl-tetrazol-2-yl)-propyl]-dimethyl-amine
[3-(3,5-Dimethoxy-naphthalen-2-yl)-3-tetrazol-2-yl-propyl]-dimethyl-amine
[3-(3,5-Dimethoxy-naphthalen-2-yl)-3-(5-methyl-tetrazol-2-yl)-propyl]-dimethyl-amine
[3-(3,5-Dimethoxy-naphthalen-2-yl)-3-tetrazol-1-yl-propyl]-dimethyl-amine
Dimethyl-[3-(4-methyl-naphthalen-1-yl)-3-tetrazol-2-yl-propyl]-amine
Dimethyl-[3-(4-methyl-naphthalen-1-yl)-3-(5-methyl-tetrazol-2-yl)-propyl]-amine
[3-(4-Fluoro-naphthalen-1-yl)-3-tetrazol-2-yl-propyl]-dimethyl-amine
[3-(4-Fluoro-naphthalen-1-yl)-3-(5-methyl-tetrazol-2-yl)-propyl]-dimethyl-amine
(3-Isoquinolin-1-yl-3-tetrazol-2-yl-propyl)-dimethyl-amine
[3-Isoquinolin-1-yl-3-(5-methyl-tetrazol-2-yl)-propyl]-dimethyl-amine
(3-Benzo[1,3]dioxol-5-yl-3-tetrazol-2-yl-propyl)-dimethyl-amine
[3-Benzo[1,3]dioxol-5-yl-3-(5-methyl-tetrazol-2-yl)-propyl]-dimethyl-amine
[3-Benzo[1,3]dioxol-5-yl-3-(5-methyl-tetrazol-1-yl)-propyl]-dimethyl-amine
[3-(3,4-Dimethoxy-phenyl)-3-tetrazol-2-yl-propyl]-dimethyl-amine
[3-(2,3-Dihydro-benzo[1,4]dioxin-2-yl)-3-tetrazol-2-yl-propyl]-dimethyl-amine
[3-(2,3-Dihydro-benzo[1,4]dioxin-2-yl)-3-(5-methyl-tetrazol-2-yl)-propyl]-dimethyl-amine
Dimethyl-(3-quinolin-2-yl-3-tetrazol-2-yl-propyl)-amine
Dimethyl-[3-(5-methyl-tetrazol-2-yl)-3-quinolin-2-yl-propyl]-amine
Dimethyl-[3-(1-methyl-1H-indol-2-yl)-3-tetrazol-2-yl-propyl]-amine
Dimethyl-[3-(1-methyl-1H-indol-2-yl)-3-(5-methyl-tetrazol-2-yl)-propyl]-amine
Dimethyl-[3-(1,2,3,4-tetrahydro-naphthalen-2-yl)-3-tetrazol-2-yl-propyl]-amine
[3-(6-Chloro-pyridin-3-yl)-3-tetrazol-2-yl-propyl]-dimethyl-amine
(3-Benzo[b]thiophen-2-yl-3-tetrazol-2-yl-propyl)-dimethyl-amine
[3-Benzo[b]thiophen-2-yl-3-(5-methyl-tetrazol-2-yl)-propyl]-dimethyl-amine
(3-Benzofuran-2-yl-3-tetrazol-2-yl-propyl)-dimethyl-amine
[3-Benzofuran-2-yl-3-(5-methyl-tetrazol-2-yl)-propyl]-dimethyl-amine
(3-Benzofuran-2-yl-3-tetrazol-1-yl-propyl)-dimethyl-amine
[3-(3,4-Difluoro-phenyl)-3-(5-methyl-tetrazol-2-yl)-propyl]-dimethyl-amine
Dimethyl-[3-tetrazol-2-yl-3-(2,4,5-trifluoro-phenyl)-propyl]-amine
Dimethyl-[3-(5-methyl-tetrazol-2-yl)-3-(2,4,5-trifluoro-phenyl)-propyl]-amine
[3-(3-Bromo-4-fluoro-phenyl)-3-tetrazol-2-yl-propyl]-dimethyl-amine
[3-(3-Bromo-4-fluoro-phenyl)-3-(5-methyl-tetrazol-2-yl)-propyl]-dimethyl-amine
[3-(6-Methoxy-naphthalen-2-yl)-3-(5-methyl-tetrazol-2-yl)-propyl]-dimethyl-amine
Dimethyl-[3-(5-methyl-tetrazol-2-yl)-3-(4-phenoxy-phenyl)-propyl]-amine
[3-(4-Bromo-phenyl)-3-tetrazol-2-yl-propyl]-dimethyl-amine
[3-(4-Bromo-phenyl)-3-(5-methyl-tetrazol-2-yl)-propyl]-dimethyl-amine
Dimethyl-[3-tetrazol-2-yl-3-(4-trifluoromethyl-phenyl)-propyl]-amine
Dimethyl-[3-(5-methyl-tetrazol-2-yl)-3-(4-trifluoromethyl-phenyl)-propyl]-amine
Dimethyl-[3-tetrazol-2-yl-3-(2,3,4-trichloro-phenyl)-propyl]-amine
Dimethyl-[3-(5-methyl-tetrazol-2-yl)-3-(2,3,4-trichloro-phenyl)-propyl]-amine
[3-(3-Chloro-4-methoxy-phenyl)-3-tetrazol-2-yl-propyl]-dimethyl-amine
[3-(3-Chloro-4-methoxy-phenyl)-3-(5-methyl-tetrazol-2-yl)-propyl]-dimethyl-amine
[3-(4-tert-Butyl-phenyl)-3-(5-methyl-tetrazol-2-yl)-propyl]-dimethyl-amine
[3-(2,5-Difluoro-phenyl)-3-(5-methyl-tetrazol-2-yl)-propyl]-dimethyl-amine
[3-(2,4-Dichloro-phenyl)-3-(5-methyl-tetrazol-2-yl)-propyl]-dimethyl-amine
[3-(3-Chloro-phenyl)-3-(5-methyl-tetrazol-2-yl)-propyl]-dimethyl-amine
[3-(2-Chloro-phenyl)-3-(5-methyl-tetrazol-2-yl)-propyl]-dimethyl-amine
[3-(2,5-Difluoro-phenyl)-3-tetrazol-2-yl-propyl]-dimethyl-amine
[3-(2,4-Dichloro-phenyl)-3-tetrazol-2-yl-propyl]-dimethyl-amine
[3-(3-Chloro-phenyl)-3-tetrazol-2-yl-propyl]-dimethyl-amine
Dimethyl-[3-(5-methyl-tetrazol-2-yl)-3-(4-trifluoromethoxy-phenyl)-propyl]-amine
[3-(3-Bromo-4-methyl-phenyl)-3-(5-methyl-tetrazol-2-yl)-propyl]-dimethyl-amine
Dimethyl-[3-tetrazol-2-yl-3-(4-trifluoromethoxy-phenyl)-propyl]-amine
[3-(4-Bromo-3-methyl-phenyl)-3-tetrazol-2-yl-propyl]-dimethyl-amine
[3-(4-Methanesulfonyl-phenyl)-3-(5-methyl-tetrazol-2-yl)-propyl]-dimethyl-amine
[3-(4-Isopropyl-phenyl)-3-(5-methyl-tetrazol-2-yl)-propyl]-dimethyl-amine
[3-(9H-Fluoren-2-yl)-3-(5-methyl-tetrazol-2-yl)-propyl]-dimethyl-amine
Methyl-(3-naphthalen-2-yl-3-[1,2,3]triazol-2-yl-propyl)-amine
[3-Benzotriazol-2-yl-3-(3,4-dichloro-phenyl)-propyl]-methyl-amine
Methyl-[3-(5-methyl-tetrazol-2-yl)-3-naphthalen-2-yl-propyl]amine
(3-Benzotriazol-2-yl-3-naphthalen-2-yl-propyl)-methyl-amine
(3-Biphenyl-4-yl-3-tetrazol-2-yl-propyl)-methyl-amine
[3-(3,4-Dichloro-phenyl)-3-(5-methyl-tetrazol-2-yl)-propyl]-methyl-amine
[3-(4-Chloro-phenyl)-3-tetrazol-2-yl-propyl]-methyl-amine
[3-(3,4-Dichloro-phenyl)-3-[1,2,3]triazol-2-yl-propyl]-methyl-amine
[3-(3,4-Dichloro-phenyl)-3-tetrazol-2-yl-propyl]-methyl-amine
Methyl(3-naphthalen-2-yl-3-tetrazol-2-yl-propyl)-amine

[3-(6-Chloro-naphthalen-2-yl)-3-tetrazol-2-yl-propyl]-methyl-amine
Methyl-(3-naphthalen-1-yl-3-tetrazol-2-yl-propyl)-amine
Methyl-[3-(6-methyl-naphthalen-2-yl)-3-tetrazol-2-yl-propyl]-amine
Methyl-[3-naphthalen-2-yl-3-(5-phenyl-tetrazol-2-yl)-propyl]-amine
(3S)-3-(3,4-dichlorophenyl)-N-methyl-3-(2H-tetrazol-2-yl)propan-1-amine
(3R)-3-(3,4-dichlorophenyl)-N-methyl-3-(2H-tetrazol-2-yl)propan-1-amine
(3S)-3-(2H-benzotriazol-2-yl)-3-(3,4-dichlorophenyl)-N-methylpropan-1-amine
(3R)-3-(2H-benzotriazol-2-yl)-3-(3,4-dichlorophenyl)-N-methylpropan-1-amine
(3S)-3-(3,4-dichlorophenyl)-N-methyl-3-(2H-1,2,3-triazol-2-yl)propan-1-amine
(3S)-3-(3,4-dichlorophenyl)-N-methyl-3-(5-methyl-2H-tetrazol-2-yl)propan-1-amine
(3R)-3-(3,4-dichlorophenyl)-N-methyl-3-(5-methyl-2H-tetrazol-2-yl)propan-1-amine
(3R)-3-(3,4-dichlorophenyl)-N-methyl-3-(2H-1,2,3-triazol-2-yl)propan-1-amine
(3R)-N-methyl-3-(2-naphthyl)-3 (2H-tetrazol-2-yl)propan-1-amine
(3S)-N-methyl-3-(2-naphthyl)-3 (2H-tetrazol-2-yl)propan-1-amine
[3-(3-Methoxy-naphthalen-2-yl)-3-tetrazol-2-yl-propyl]-methyl-amine
[3-(3-Methoxy-naphthalen-2-yl)-3-(5-methyl-tetrazol-2-yl)-propyl]-methyl-amine
[3-(6-Fluoro-naphthalen-2-yl)-3-tetrazol-2-yl-propyl]-methyl-amine
[3-(6-Fluoro-naphthalen-2-yl)-3-(5-methyl-tetrazol-2-yl)-propyl]-methyl-amine
[3-(1,4-Dimethoxy-naphthalen-2-yl)-3-tetrazol-2-yl-propyl]-methyl-amine
[3-(1,4-Dimethoxy-naphthalen-2-yl)-3-(5-methyl-tetrazol-2-yl)-propyl]-methyl-amine
[3-(3,5-Dimethoxy-naphthalen-2-yl)-3-tetrazol-2-yl-propyl]-methyl-amine
[3-(3,5-Dimethoxy-naphthalen-2-yl)-3-(5-methyl-tetrazol-2-yl)-propyl]-methyl-amine
[3-(3,5-Dimethoxy-naphthalen-2-yl)-3-tetrazol-1-yl-propyl]-methyl-amine
Methyl-[3-(4-methyl-naphthalen-1-yl)-3-tetrazol-2-yl-propyl]-amine
Methyl-[3-(4-methyl-naphthalen-1-yl)-3-(5-methyl-tetrazol-2-yl)-propyl]-amine
[3-(4-Fluoro-naphthalen-1-yl)-3-tetrazol-2-yl-propyl]-methyl-amine
[3-(4-Fluoro-naphthalen-1-yl)-3-(5-methyl-tetrazol-2-yl)-propyl]-methyl-amine
(3-Benzo[1,3]dioxol-5-yl-3-tetrazol-2-yl-propyl)-methyl-amine
[3-Benzo[1,3]dioxol-5-yl-3-(5-methyl-tetrazol-2-yl)-propyl]-methyl-amine
[3-Benzo[1,3]dioxol-5-yl-3-(5-methyl-tetrazol-1-yl)-propyl]-methyl-amine
[3-(3,4-Dimethoxy-phenyl)-3-tetrazol-2-yl-propyl]-methyl-amine
[3-(2,3-Dihydro-benzo[1,4]dioxin-2-yl)-3-tetrazol-2-yl-propyl]-methyl-amine
[3-(2,3-Dihydro-benzo[1,4]dioxin-2-yl)-3-(5-methyl-tetrazol-2-yl)-propyl]-methyl-amine
Methyl-[3-(1,2,3,4-tetrahydro-naphthalen-2-yl)-3-tetrazol-2-yl-propyl]-amine
[3-(6-Chloro-pyridin-3-yl)-3-tetrazol-2-yl-propyl]-methyl-amine
(3-Benzo[b]thiophen-2-yl-3-tetrazol-2-yl-propyl)-methyl-amine
[3-Benzo[b]thiophen-2-yl-3-(5-methyl-tetrazol-2-yl)-propyl]-methyl-amine
(3-Benzofuran-2-yl-3-tetrazol-2-yl-propyl)-methyl-amine
[3-Benzofuran-2-yl-3-(5-methyl-tetrazol-2-yl)-propyl]-methyl-amine
(3-Benzofuran-2-yl-3-tetrazol-1-yl-propyl)-methyl-amine
[3-(3,4-Difluoro-phenyl)-3-tetrazol-2-yl-propyl]-methyl-amine
[3-(3,4-Difluoro-phenyl)-3-(5-methyl-tetrazol-2-yl)-propyl]-methyl-amine
Methyl-[3-tetrazol-2-yl-3-(2,4,5-trifluoro-phenyl)-propyl]-amine
Methyl-[3-(5-methyl-tetrazol-2-yl)-3-(2,4,5-trifluoro-phenyl)-propyl]-amine
[3-(3-Bromo-4-fluoro-phenyl)-3-tetrazol-2-yl-propyl]-methyl-amine
[3-(3-Bromo-4-fluoro-phenyl)-3-(5-methyl-tetrazol-2-yl)-propyl]-methyl-amine
[3-(6-Methoxy-naphthalen-2-yl)-3-tetrazol-2-yl-propyl]-methyl-amine
[3-(6-Methoxy-naphthalen-2-yl)-3-(5-methyl-tetrazol-2-yl)-propyl]-methyl-amine
Methyl-[3-(4-phenoxy-phenyl)-3-tetrazol-2-yl-propyl]-amine
Methyl-[3-(5-methyl-tetrazol-2-yl)-3-(4-phenoxy-phenyl)-propyl]-amine
[3-(4-Bromo-phenyl)-3-tetrazol-2-yl-propyl]-methyl-amine
[3-(4-Bromo-phenyl)-3-(5-methyl-tetrazol-2-yl)-propyl]-methyl-amine
Methyl-[3-tetrazol-2-yl-3-(4-trifluoromethyl-phenyl)-propyl]-amine
Methyl-[3-(5-methyl-tetrazol-2-yl)-3-(4-trifluoromethyl-phenyl)-propyl]-amine
Methyl-[3-tetrazol-2-yl-3-(2,3,4-trichloro-phenyl)-propyl]-amine
Methyl-[3-(5-methyl-tetrazol-2-yl)-3-(2,3,4-trichloro-phenyl)-propyl]-amine
[3-(3-Chloro-4-methoxy-phenyl)-3-tetrazol-2-yl-propyl]-methyl-amine
[3-(3-Chloro-4-methoxy-phenyl)-3-(5-methyl-tetrazol-2-yl)-propyl]-methyl-amine
[3-(2-Chloro-phenyl)-3-(5-methyl-tetrazol-2-yl)-propyl]-methyl-amine
[3-(3-Chloro-phenyl)-3-(5-methyl-tetrazol-2-yl)-propyl]-methyl-amine
[3-(2,4-Dichloro-phenyl)-3-(5-methyl-tetrazol-2-yl)-propyl]-methyl-amine
[3-(2,5-Difluoro-phenyl)-3-(5-methyl-tetrazol-2-yl)-propyl]-methyl-amine
[3-(3-Chloro-phenyl)-3-tetrazol-2-yl-propyl]-methyl-amine
[3-(2,4-Dichloro-phenyl)-3-tetrazol-2-yl-propyl]-methyl-amine
[3-(2,5-Difluoro-phenyl)-3-tetrazol-2-yl-propyl]-methyl-amine
[3-(4-Methanesulfonyl-phenyl)-3-(5-methyl-tetrazol-2-yl)-propyl]-methyl-amine
[3-(4-Isopropyl-phenyl)-3-(5-methyl-tetrazol-2-yl)-propyl]-methyl-amine
[3-(9H-Fluoren-2-yl)-3-(5-methyl-tetrazol-2-yl)-propyl]-methyl-amine
(3S)-Methyl-[3-(5-methyl-tetrazol-2-yl)-3-naphthalen-2-yl-propyl]-amine
(3S)-Methyl-[3-naphthalen-2-yl-3-(5-phenyl-tetrazol-2-yl)-propyl]-amine
(3R)-Methyl-[3-(5-methyl-tetrazol-2-yl)-3-naphthalen-2-yl-propyl]-amine
(3R)-Methyl-[3-naphthalen-2-yl-3-(5-phenyl-tetrazol-2-yl)-propyl]-amine (3R)-[3-(6-Fluoro-naphthalen-2-yl)-3-(5-methyl-tetrazol-2-yl)-propyl]-methyl-amine (3S)-[3-(6-Fluoro-naphthalen-2-yl)-3-(5-methyl-tetrazol-2-yl)-propyl]-methyl-amine The compound or pharmaceutically acceptable salt thereof according to the present invention can be used for treating CNS disorders such as depression, anxiety and pain disorder.

In therapeutic use as agents for various CNS disorders such as depression, anxiety and pain disorder, the compounds of the present invention, alone or in combination with pharmaceutically acceptable carrier, are administered to patients at a dosage of from 0.7 to 7,000 mg per day. For a normal human adult with a body weight of approximately 70 kg, the administration amount is translated into a daily dose of 0.01 to 100 mg per kg of body weight. The specific dosage employed, however, may vary depending upon the requirements of the patient, the severity of patient's condition and the activity of the compound. The determination of optimum dosages for a particular situation must clinically be done and is within the skill of the art.

In utilizing the compounds of the present invention for the central nervous system, the compounds represented by general structural formula (I), (III), (IV) and (V) can be administered in any form or mode which makes the compound bioavailable in effective amounts, including the oral, rectal, transdermal, subcutaneous, intravenous, intramuscular or intranasal routs. However it is preferred to administer the compounds orally. Since the compounds absorb well orally, it usually will not be necessary to resort to parenteral administration. For oral administration, the compounds having the general formula (I), (III), (IV) and (V) is preferably combined with a pharmaceutical carrier. The ratio of the carrier to the compound of structural formula (I), (III), (IV) and (V) is not critical to express the effects of the medicine on the central nervous system, and they can vary considerably depending on whether the composition is to be filled into capsules or formed into tablets. In tableting, various edible pharmaceutical carriers or the mixture thereof can be used. A suitable carriers, for example, are a mixture of lactose, diabasic calcium phosphate and/or corn starch. Other pharmaceutically acceptable ingredients can be further added, including lubricants such as magnesium stearate.

The present invention includes methods of treating depression, anxiety and pain disorder in a mammal which comprises administering the composition of the compound of structural formula (I), (III), (IV) and (V) to a mammal in need of therapy.

A better understanding of the present invention may be obtained in light of following examples which are set forth to illustrate, but are not to be construed to limit, the present invention.

Example 1

[3-(3,4-Dichloro-phenyl)-3-tetrazol-2-yl-propyl]-dimethyl-amine

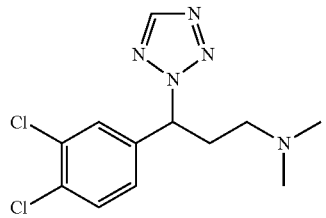 [SMILES: CN(C)CCC(c1ccc(Cl)c(Cl)c1)n1ncnn1]

To a solution of 3,4-dichloroacetophenone (2 mmol) in ethanol was added dimethylamine (5 equiv.), paraformaldehyde (5 equiv.) and aq. HCl. After 12 h, the solvent was removed and ethyl acetate and 1N NaOH were added and organic layer was extracted 3 times. It was dried over $MgSO_4$, filtered, evaporated and the filtrate was concentrated at reduced pressure. The residue was purified by column chromatography eluting with ethyl acetate and hexane. The product was dissolved in methanol and added $NaBH_4$ (2 equiv.). After 2 h, sat. $NaHCO_3$ and ethyl acetate were added and the organic layer was extracted 3 times with ethyl acetate. It was dried over $MgSO_4$, filtered, evaporated and the filtrate was concentrated at reduced pressure. The residue was purified by column chromatography eluting with ethyl acetate and methanol. The resulting residue was dissolved in THF and was added 1H-tetrazole (1.5 equiv.), triphenylphosphine (1.5 equiv.) and diisopropyl azodicarboxylate (1.5 equiv.) dropwise at 0□ and warmed to room temperature. After 2 h, the solvent was removed and the residue was purified by column chromatography eluting with ethyl acetate and methanol. Yield 35%

1H-NMR (CDCl3, 200 MHz) δ 2.2 (m, 7H), 2.6 (m, 2H), 6.0 (t, 1H), 7.2 (dd, 1H), 7.4 (dd, 1H), 7.5 (d, 1H), 8.5 (s, 1H)

Example 2

[3-(3,4-Dichloro-phenyl)-3-tetrazol-2-yl-propyl]-methyl-amine

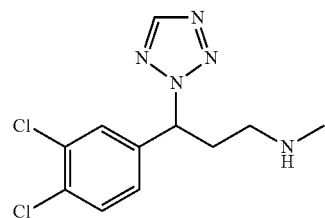

To a solution of [3-(3,4-Dichloro-phenyl)-3-tetrazol-2-yl-propyl]-dimethyl-amine (2 mmol) in chloroform was added ethylchloroformate (>10 equiv.) and $NaHCO_3$ (>20 equiv.) and this solution was refluxed for 3 h. After that, chloroform was evaporated and ethyl acetate was added and then this organic layer was washed with water 3 times. It was dried over $MgSO_4$, filtered, evaporated and the filtrate was concentrated at reduced pressure. The residue was dissolved in ethanol and potassium hydroxide (>20 equiv.) dissolved in water was added and refluxed for 3 days. After that, ethyl acetate and sat. NaHCO3 were added and the organic layer was extracted. It was dried over $MgSO_4$, filtered, evaporated and the filtrate was concentrated at reduced pressure. The residue was purified by column chromatography eluting with ethyl acetate and methanol: Yield 80%

1H-NMR (CDCl3, 200 MHz) δ 2.4 (m, 3H), 2.5 (m, 3H), 2.7 (m, 1H), 6.2 (m, 1H), 7.2 (m, 1H), 7.4 (m, 1H), 7.5 (s, 1H), 8.5 (s, 1H)

Example 3

S-[3-(3,4-Dichloro-phenyl)-3-tetrazol-2-yl-propyl]-methyl-amine

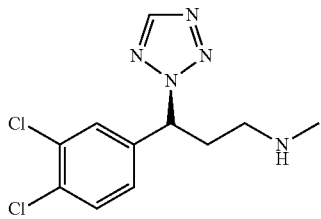

S-[3-(3,4-Dichloro-phenyl)-3-tetrazol-2-yl-propyl]-methyl-amine was obtained from the [3-(3,4-Dichloro-phenyl)-3-tetrazol-2-yl-propyl]-methyl-amine using a CHIRAL-PACK OD-H column (manufactured by Daicel Chemical Industries, Ltd.) as the Prep-LC column, at a column temperature of 25° C., with n-hexane/isopropylalcohol including 0.1% triethylamine (90:10) as the eluent.

1H-NMR (CDCl3, 200 MHz) δ 2.4 (m, 3H), 2.5 (m, 3H), 2.7 (m, 1H), 6.2 (m, 1H), 7.2 (m, 1H), 7.4 (m, 1H), 7.5 (s, 1H), 8.5 (s, 1H)

Example 4

[3-Benzotriazol-2-yl-3-(3,4-dichloro-phenyl)-propyl]-dimethyl-amine

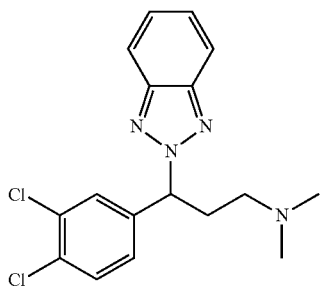 [SMILES: CN(C)CCC(c1ccc(Cl)c(Cl)c1)n1nc2ccccc2n1]

The procedure given in Example 1 was followed using benzotriazole as a reactant, instead of tetrazole, to give [3-Benzotriazol-2-yl-3-(3,4-dichloro-phenyl)-propyl]-dimethyl-amine 1H-NMR (CDCl3, 200 MHz) δ 2.2 (s, 8H), 2.5 (m, 1H), 2.8 (m, 1H), 6.1 (m, 1H), 7.4 (m, 4H), 7.6 (t, 1H), 7.9 (m, 2H)

Example 5

Dimethyl-(3-naphthalen-2-yl-3-[1,2,3]triazol-2-yl-propyl)-amine

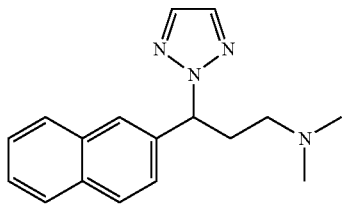 [SMILES: CN(C)CCC(c1ccc2ccccc2c1)n1nccn1]

The procedure given in Example 1 was followed using 2-acetonaphthone and 1H-1,2,3-triazole as reactants, instead of 3,4-dichloroacetophenone and 1H-tetrazole, to give Dimethyl-(3-naphthalen-2-yl-3-[1,2,3]triazol-2-yl-propyl)-amine.

1H-NMR (CDCl3, 200 MHz) δ 2.2 (s, 8H), 2.5 (m, 1H), 2.8 (m, 1H), 6.1 (m, 1H), 7.4 (m, 3H), 7.6 (d, 2H), 7.8 (m, 5H)

Example 6

Dimethyl-(3-naphthalen-2-yl-3-tetrazol-2-yl-propyl)-amine

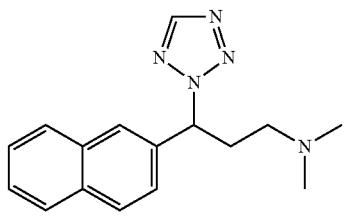 [SMILES: CN(C)CCC(c1ccc2ccccc2c1)n1ncnn1]

The procedure given in Example 1 was followed using 2-acetonaphthone as a reactant, instead of 3,4-dichloroacetophenone, to give Dimethyl-(3-naphthalen-2-yl-3-tetrazol-2-yl-propyl)-amine.

1H-NMR (CDCl3, 200 MHz) δ 2.2 (s, 8H), 2.5 (m, 1H), 2.8 (m, 1H), 6.1 (m, 1H), 7.5 (m, 3H), 7.8 (m, 4H), 8.5 (s, 1H)

Example 7

(3-Benzotriazol-2-yl-3-naphthalen-2-yl-propyl)-dimethyl-amine

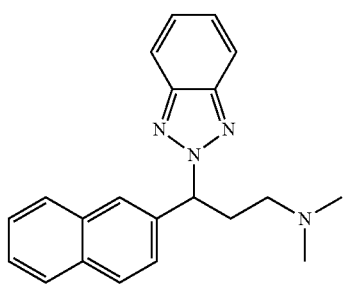 [SMILES: CN(C)CCC(c1ccc2ccccc2c1)n1nc2ccccc2n1]

The procedure given in Example 1 was followed using 2-acetonaphthone and benzotriazole as reactants, instead of 3,4-dichloroacetophenone and 1H-tetrazole, to give (3-Benzotriazol-2-yl-3-naphthalen-2-yl-propyl)-dimethyl-amine.

1H-NMR (CDCl3, 200 MHz) δ 2.2 (s, 8H), 2.5 (m, 1H), 2.8 (m, 1H), 6.1 (m, 1H), 7.4 (m, 5H), 7.5 (d, 1H), 7.8 (m, 6H)

Example 8

Dimethyl-[3-(5-methyl-tetrazol-2-yl)-3-naphthalen-2-yl-propyl]-amine

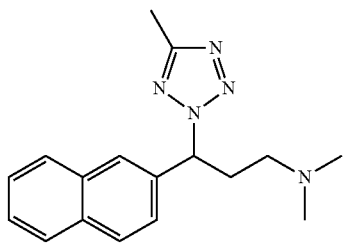 [SMILES: Cc1nnn(C(CCN(C)C)c2ccc3ccccc3c2)n1]

The procedure given in Example 1 was followed using 2-acetonaphthone and 5-methyl-1H-tetrazole as reactants, instead of 3,4-dichloroacetophenone and 1H-tetrazole, to give Dimethyl-[3-(5-methyl-tetrazol-2-yl)-3-naphthalen-2-yl-propyl]-amine.

1H-NMR (CDCl3, 200 MHz) δ 2.2 (s, 8H), 2.5 (m, 1H), 2.8 (m, 1H), 6.1 (m, 4H), 7.5 (d, 3H), 7.8 (d, 4H)

Example 9

[3-(6-Chloro-naphthalen-2-yl)-3-tetrazol-1-yl-propyl]-dimethyl-amine

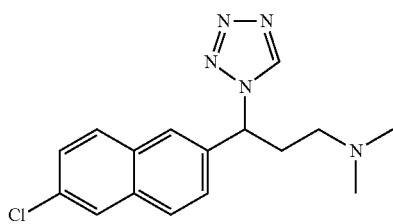 [SMILES: CN(C)CCC(c1ccc2cc(Cl)ccc2c1)n1cnnn1]

The procedure given in Example 1 was followed using 6-Chloro-2-acetonaphthone as a reactant, instead of 3,4-dichloroacetophenone, to give [3-(6-Chloro-naphthalen-2-yl)-3-tetrazol-1-yl-propyl]-dimethyl-amine.

1H-NMR (CDCl3, 200 MHz) δ 2.2 (s, 8H), 2.5 (m, 1H), 2.8 (m, 1H), 6.7 (m, 1H), 7.5 (m, 3H), 7.8 (dd, 2H), 8.1 (s, 1H), 8.6 (s, 1H)

Example 10

Dimethyl-[3-(4-phenoxy-phenyl)-3-tetrazol-2-yl-propyl]-amine

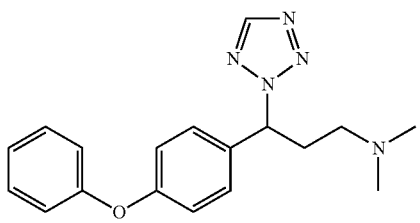 [SMILES: CN(C)CCC(c1ccc(Oc2ccccc2)cc1)n1ncnn1]

The procedure given in Example 1 was followed using 4-phenoxyacetophenone as a reactant, instead of 3,4-dichloroacetophenone, to give Dimethyl-[3-(4-phenoxy-phenyl)-3-tetrazol-2-yl-propyl]-amine.

1H-NMR (CDCl3, 200 MHz) δ 2.2 (s, 8H), 2.5 (m, 1H), 2.8 (m, 1H), 6.1 (m, 1H), 6.9 (m, 4H), 7.1 (m, 1H), 7.4 (m, 4H), 8.5 (s, 1H)

Example 11

Dimethyl-[3-(4-phenoxy-phenyl)-3-tetrazol-1-yl-propyl]-amine

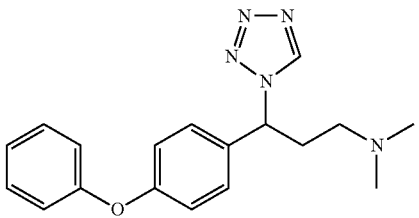 [SMILES: CN(C)CCC(c1ccc(Oc2ccccc2)cc1)n1cnnn1]

The procedure given in Example 1 was followed using 4-phenoxyacetophenone as a reactant, instead of 3,4-dichloroacetophenone, to give Dimethyl-[3-(4-phenoxy-phenyl)-3-tetrazol-1-yl-propyl]-amine.

1H-NMR (CDCl3, 200 MHz) δ 2.2 (s, 8H), 2.5 (m, 1H), 2.8 (m, 1H), 5.8 (m, 1H), 6.9 (m, 4H), 7.1 (m, 1H), 7.4 (m, 4H), 8.5 (s, 1H)

Example 12

[3-(6-Chloro-naphthalen-2-yl)-3-[(1,2,3]triazol-2-yl-propyl]-dimethyl-amine

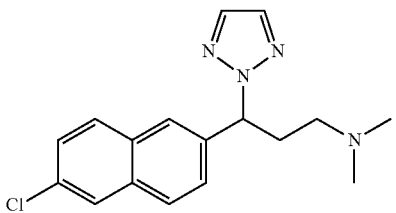 [SMILES: CN(C)CCC(c1ccc2cc(Cl)ccc2c1)n1nccn1]

The procedure given in Example 1 was followed using 6-Chloro-2-acetonaphthone and 1H-1,2,3-triazole as reactants, instead of 3,4-dichloroacetophenone and 1H-tetrazole, to give [3-(6-Chloro-naphthalen-2-yl)-3-[1,2,3]triazol-2-yl-propyl]-dimethyl-amine 1H-NMR (CDCl3, 200 MHz) δ 2.2 (s, 8H), 2.5 (m, 1H), 2.8 (m, 1H), 6.7 (m, 1H), 7.4 (m, 3H), 7.6 (m, 2H), 7.8 (m, 2H), 8.4 (s, 1H)

Example 13

[3-(6-Chloro-naphthalen-2-yl)-3-[1,2,3]triazol-1-yl-propyl]-dimethyl-amine

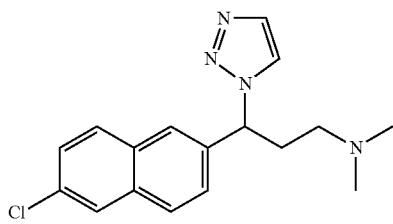

The procedure given in Example 1 was followed using 6-Chloro-2-acetonaphthone and 1H-1,2,3-triazole as reactants, instead of 3,4-dichloroacetophenone and 1H-tetrazole, to give [3-(6-Chloro-naphthalen-2-yl)-3-[1,2,3]triazol-1-yl-propyl]-dimethyl-amine.

1H-NMR (CDCl3, 200 MHz) δ 2.2 (s, 8H), 2.5 (m, 1H), 2.8 (m, 1H), 6.7 (m, 1H), 7.4 (m, 3H), 7.6 (m, 2H), 7.8 (m, 2H), 8.2 (s, 1H)

Example 14

[3-(6-Chloro-naphthalen-2-yl)-3-tetrazol-2-yl-propyl]-dimethyl-amine

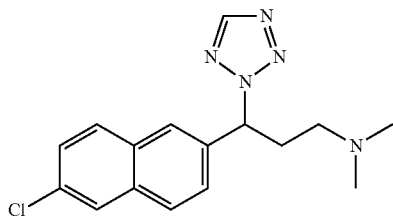 [SMILES: CN(C)CCC(c1ccc2cc(Cl)ccc2c1)n1ncnn1]

The procedure given in Example 1 was followed using 6-Chloro-2-acetonaphthone as a reactant, instead of 3,4-dichloroacetophenone, to give [3-(6-Chloro-naphthalen-2-yl)-3-tetrazol-2-yl-propyl]-dimethyl-amine.

1H-NMR (CDCl3, 200 MHz) δ 2.2 (s, 8H), 2.5 (m, 1H), 2.8 (m, 1H), 6.7 (m, 1H), 7.5 (m, 3H), 7.8 (dd, 2H), 8.3 (s, 1H), 8.5 (s, 1H)

Example 15

[3-(4-Methoxy-phenyl)-3-[1,2,3]triazol-2-yl-propyl]-dimethyl-amine

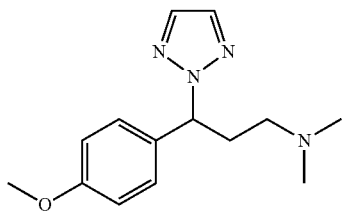

The procedure given in Example 1 was followed using 4-methoxyacetophenone and 1H-1,2,3-triazole as reactants, instead of 3,4-dichloroacetophenone and 1H-tetrazole, to give [3-(4-Methoxy-phenyl)-3-[1,2,3]triazol-2-yl-propyl]-dimethyl-amine.

1H-NMR (CDCl3, 200 MHz) δ 2.2 (s, 8H), 2.5 (m, 2H), 2.8 (m, 1H), 5.7 (m, 1H), 6.8 (dd, 2H), 7.3 (dd, 2H), 7.6 (s, 2H)

Example 16

(3-Biphenyl-3-yl-3-tetrazol-2-yl-propyl)-dimethyl-amine

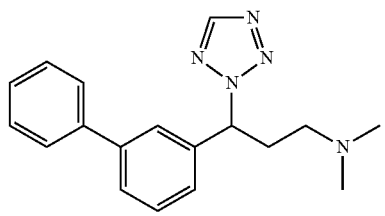 [SMILES: CN(C)CCC(c1cccc(-c2ccccc2)c1)n1ncnn1]

The procedure given in Example 1 was followed using 3-phenylacetophenone as a reactant, instead of 3,4-dichloroacetophenone, to give (3-Biphenyl-3-yl-3-tetrazol-2-yl-propyl)-dimethyl-amine.

1H-NMR (CDCl3, 200 MHz) δ 2.2 (s, 8H), 2.5 (m, 1H), 2.8 (m, 1H), 6.2 (m, 1H), 7.5 (m, 9H), 8.5 (s, 1H)

Example 17

[3-(4-Benzyloxy-phenyl)-3-tetrazol-2-yl-propyl]-dimethyl-amine

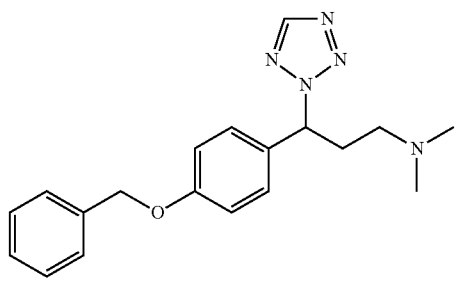 [SMILES: CN(C)CCC(c1ccc(OCc2ccccc2)cc1)n1ncnn1]

The procedure given in Example 1 was followed using 4-benzyloxyacetophenone as a reactant, instead of 3,4-dichloroacetophenone, to give [3-(4-Benzyloxy-phenyl)-3-tetrazol-2-yl-propyl]-dimethyl-amine.

1H-NMR (CDCl3, 200 MHz) δ 2.2 (s, 8H), 2.5 (m, 1H), 2.8 (m, 1H), 5.0 (s, 2H), 6.1 (m, 1H), 7.0 (m, 2H), 7.4 (m, 7H), 8.5 (s, 1H)

Example 18

(3-Biphenyl-4-yl-3-tetrazol-2-yl-propyl)-dimethyl-amine

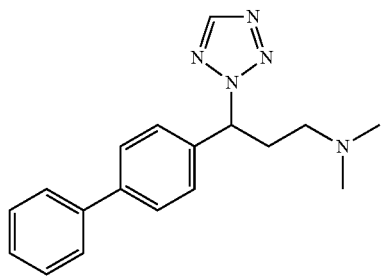 [SMILES: CN(C)CCC(c1ccc(-c2ccccc2)cc1)n1ncnn1]

The procedure given in Example 1 was followed using 4-phenylacetophenone as a reactant, instead of 3,4-dichloroacetophenone, to give (3-Biphenyl-4-yl-3-tetrazol-2-yl-propyl)-dimethyl-amine.

1H-NMR (CDCl3, 200 MHz) δ 2.2 (s, 8H), 2.5 (m, 1H), 2.8 (m, 1H), 6.1 (m, 1H), 7.4 (m, 9H), 8.5 (s, 1H)

Example 19

Dimethyl-[3-naphthalen-2-yl-3-(5-phenyl-tetrazol-2-yl)-propyl]-amine

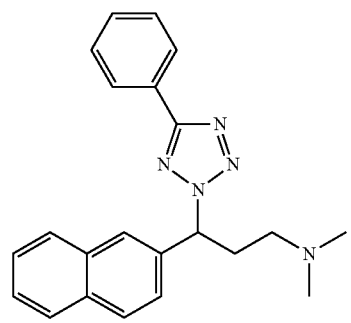 [SMILES: CN(C)CCC(c1ccc2ccccc2c1)n1nnc(-c2ccccc2)n1]

The procedure given in Example 1 was followed using 2-acetonaphthone and 5-Methyl-1H-tetrazole as reactants, instead of 3,4-dichloroacetophenone and 1H-tetrazole, to give Dimethyl-[3-naphthalen-2-yl-3-(5-phenyl-tetrazol-2-yl)-propyl]-amine.

1H-NMR (CDCl3, 200 MHz) δ 2.2 (s, 8H), 2.5 (m, 1H), 2.8 (m, 1H), 6.1 (m, 1H), 7.5 (m, 5H), 7.6 (m, 1H), 7.8 (m, 3H), 8.0 (s, 1H), 8.2 (m, 2H)

Example 20

Dimethyl-[3-(6-methyl-naphthalen-2-yl)-3-tetrazol-2-yl-propyl]-amine

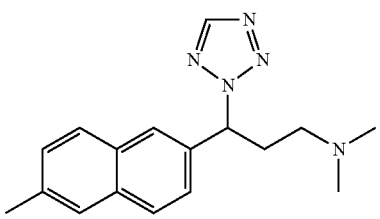

The procedure given in Example 1 was followed using 6-Methylacetonaphthone as a reactant, instead of 3,4-dichloroacetophenone, to give Dimethyl-[3-(6-methyl-naphthalen-2-yl)-3-(5-methyl-tetrazol-2-yl)-propyl]-amine.

1H-NMR (CDCl3, 200 MHz) δ 2.2 (s, 8H), 2.5 (m, 3H), 2.8 (m, 1H), 6.1 (m, 1H), 7.3 (dd, 1H), 7.5 (m, 2H), 7.7 (dd, 2H), 7.9 (s, 1H), 8.5 (s, 1H)

Example 21

[3-(6-Methoxy-naphthalen-2-yl)-3-tetrazol-2-yl-propyl]-dimethyl-amine

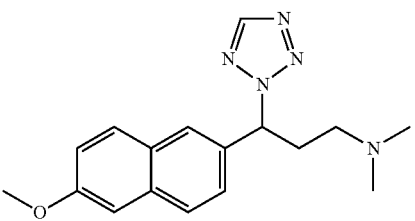

The procedure given in Example 1 was followed using 6-Methoxyacetonaphthone as a reactant, instead of 3,4-dichloroacetophenone, to give [3-(6-Methoxy-naphthalen-2-yl)-3-tetrazol-2-yl-propyl]-dimethyl-amine.

1H-NMR (CDCl3, 200 MHz) δ 2.2 (s, 8H), 2.5 (m, 1H), 2.8 (m, 1H), 3.9 (s, 3H), 6.1 (m, 1H), 7.3 (dd, 1H), 7.5 (m, 2H), 7.7 (dd, 2H), 7.9 (s, 1H), 8.5 (s, 1H)

Example 22

[3-(6-Methoxy-naphthalen-2-yl)-3-[1,2,3]triazol-2-yl-propyl]-dimethyl-amine

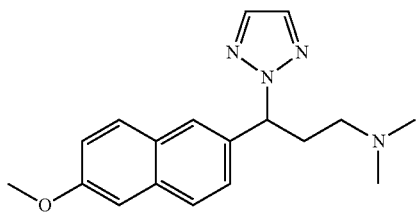

The procedure given in Example 1 was followed using 6-Methoxyacetonaphthone and 1H-1,2,3-triazole as reactants, instead of 3,4-dichloroacetophenone and 1H-tetrazole, to give [3-(6-Methoxy-naphthalen-2-yl)-3-[1,2,3]triazol-2-yl-propyl]-dimethyl-amine.

1H-NMR (CDCl3, 200 MHz) δ 2.2 (s, 8H), 2.5 (m, 1H), 2.8 (m, 1H), 3.9 (s, 3H), 6.1 (m, 1H), 7.3 (dd, 1H), 7.5 (m, 2H), 7.7 (dd, 2H), 7.9 (s, 1H), 8.5 (s, 2H)

Example 23

[3-Benzotriazol-1-yl-3-(3,4-dichloro-phenyl)-propyl]-dimethyl-amine

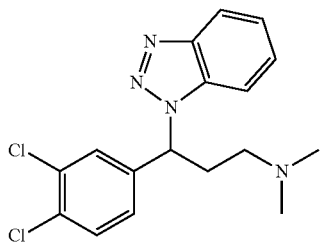 [SMILES: CN(C)CCC(c1ccc(Cl)c(Cl)c1)n1nnc2ccccc21]

The procedure given in Example 1 was followed using benzotriazole as a reactant, instead of 1H-tetrazole, to give [3-Benzotriazol-1-yl-3-(3,4-dichloro-phenyl)-propyl]-dimethyl-amine.

1H-NMR (CDCl3, 200 MHz) δ 2.2 (s, 8H), 2.5 (m, 1H), 2.8 (m, 1H), 6.0 (m, 1H), 7.4 (m, 6H), 8.0 (t, 1H)

Example 24

2-[1-(3,4-Dichloro-phenyl)-3-pyrrolidin-1-yl-propyl]-2H-[1,2,3]triazole

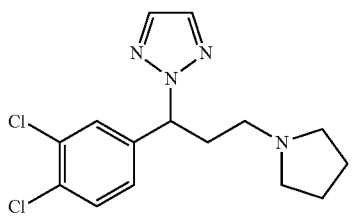 [SMILES: Clc1ccc(C(CCN2CCCC2)n2nccn2)cc1Cl]

The procedure given in Example 1 was followed using pyrrolidine and 1H-1,2,3-triazole as reactants, instead of dimethylamine and 1H-tetrazole, to give 2-[1-(3,4-Dichloro-phenyl)-3-pyrrolidin-1-yl-propyl]-2H-[1,2,3]triazole.

1H-NMR (CDCl3, 200 MHz) δ 1.84 (m, 4H), 2.2 (m, 7H), 2.7 (m, 1H), 6.0 (m, 1H), 7.2 (m, 3H), 7.6 (m, 2H)

Example 25

[3-(3,4-Dichloro-phenyl)-3-[1,2,3]triazol-2-yl-propyl]-diethyl-amine

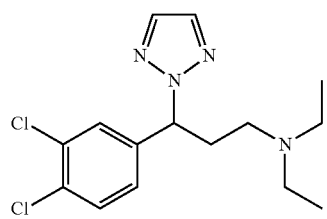 [SMILES: CCN(CC)CCC(c1ccc(Cl)c(Cl)c1)n1nccn1]

The procedure given in Example 1 was followed using diethylamine and 1H-1,2,3-triazole as reactants, instead of dimethylamine and 1H-tetrazole, to give [3-(3,4-Dichloro-phenyl)-3-[1,2,3]triazol-2-yl-propyl]-diethyl-amine.

1H-NMR (CDCl3, 200 MHz) δ 1.0 (m, 6H), 2.3 (m, 7H), 2.6 (m, 1H), 6.0 (m, 1H), 7.2 (m, 3H), 7.6 (m, 2H)

Example 26

[3-(3,4-Dichloro-phenyl)-3-tetrazol-2-yl-propyl]-diethyl-amine

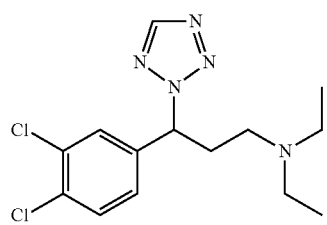 [SMILES: CCN(CC)CCC(c1ccc(Cl)c(Cl)c1)n1ncnn1]

The procedure given in Example 1 was followed using diethylamine as a reactant, instead of dimethylamine, to give [3-(3,4-Dichloro-phenyl)-3-tetrazol-2-yl-propyl]-diethyl-amine.

1H-NMR (CDCl3, 200 MHz) δ 1.0 (m, 6H), 2.3 (m, 7H), 2.6 (m, 1H), 6.0 (m, 1H), 7.2 (dd, 1H), 7.4 (dd, 1H), 7.6 (t, 1H), 8.5 (s, 1H)

Example 27

2-[1-(3,4-Dichloro-phenyl)-3-pyrrolidin-1-yl-propyl]-2H-tetrazole

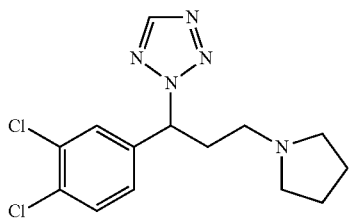 [SMILES: Clc1ccc(C(CCN2CCCC2)n2ncnn2)cc1Cl]

The procedure given in Example 1 was followed using pyrrolidine as a reactant, instead of dimethylamine, to give 2-[1-(3,4-Dichloro-phenyl)-3-pyrrolidin-1-yl-propyl]-2H-tetrazole.

1H-NMR (CDCl3, 200 MHz) δ 1.8 (m, 4H), 2.4 (m, 7H), 2.8 (m, 1H), 6.1 (m, 1H), 7.2 (dd, 1H), 7.4 (dd, 1H), 7.6 (t, 1H), 8.5 (s, 1H)

Example 28

Dimethyl-(3-naphthalen-1-yl-3-tetrazol-2-yl-propyl)-amine

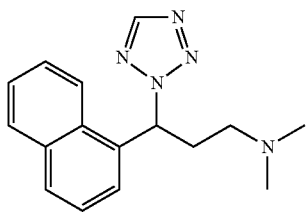 [SMILES: CN(C)CCC(c1cccc2ccccc12)n1ncnn1]

The procedure given in Example 1 was followed using 1-acetonaphthone as a reactant, instead of 3,4-dichloroacetophenone, to give Dimethyl-(3-naphthalen-1-yl-3-tetrazol-2-yl-propyl)-amine.

1H-NMR (CDCl3, 200 MHz) δ 2.2 (m, 8H), 2.6 (m, 1H), 2.9 (m, 1H), 7.0 (m, 1H), 7.5 (m, 4H), 7.9 (t, 2H), 8.3 (d, 1H), 8.5 (s, 1H)

Example 29

Dimethyl-(3-naphthalen-1-yl-3-[1,2,3]triazol-2-yl-propyl)-amine

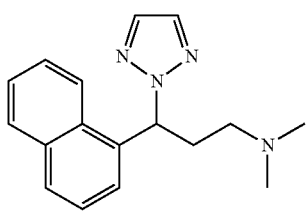 [SMILES: CN(C)CCC(c1cccc2ccccc12)n1nccn1]

The procedure given in Example 1 was followed using 1-acetonaphthone and 1H-1,2,3-triazole as reactants, instead of 3,4-dichloroacetophenone and 1H-tetrazole, to give Dimethyl-(3-naphthalen-1-yl-3-[1,2,3]triazol-2-yl-propyl)-amine.

1H-NMR (CDCl3, 200 MHz) δ 2.2 (m, 8H), 2.6 (m, 1H), 2.9 (m, 1H), 7.0 (m, 1H), 7.5 (m, 4H), 7.9 (t, 2H), 8.3 (d, 1H)

Example 30

[3-(3,4-Dichloro-phenyl)-3-(5-methyl-tetrazol-2-yl)-propyl]-dimethyl-amine

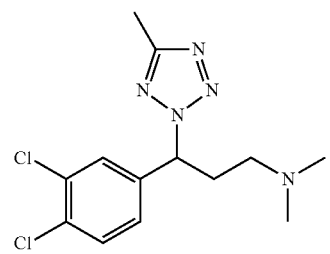 [SMILES: Cc1nnn(C(CCN(C)C)c2ccc(Cl)c(Cl)c2)n1]

The procedure given in Example 1 was followed using 5-methyl-1H-tetrazole e as a reactant, instead of 1H-tetrazole, to give [3-(3,4-Dichloro-phenyl)-3-(5-methyl-tetrazol-2-yl)-propyl]-dimethyl-amine.

1H-NMR (CDCl3, 200 MHz) δ 2.2 (m, 9H), 2.6 (m, 3H), 2.9 (m, 3H), 6.0 (t, 1H), 7.2 (dd, 1H), 7.4 (dd, 1H), 7.5 (s, 1H)

Example 31

[3-(3,4-Dichloro-phenyl)-3-(5-phenyl-tetrazol-2-yl)-propyl]-dimethyl-amine

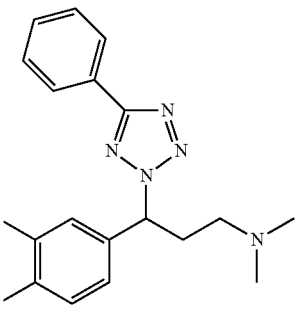

The procedure given in Example 1 was followed using 5-phenyl-1H-tetrazole as a reactant, instead of 1H-tetrazole, to give [3-(3,4-Dichloro-phenyl)-3-(5-phenyl-tetrazol-2-yl)-propyl]-dimethyl-amine.

1H-NMR (CDCl3, 200 MHz) δ 2.2 (m, 9H), 2.6 (m, 3H), 2.9 (m, 3H), 6.0 (t, 1H), 7.4 (m, 5H), 8.1 (m, 2H)

Example 32

[3-(3,4-Difluoro-phenyl)-3-tetrazol-1-yl-propyl]-dimethyl-amine

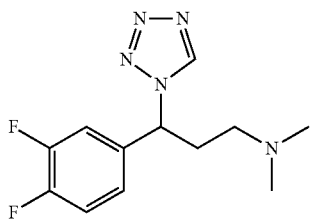 [SMILES: CN(C)CCC(c1ccc(F)c(F)c1)n1cnnn1]

The procedure given in Example 1 was followed using 3,4-difluoroacetophenone as a reactant, instead of 3,4-dichloroacetophenone, to give [3-(3,4-Difluoro-phenyl)-3-tetrazol-1-yl-propyl]-dimethyl-amine.

1H-NMR (CDCl3, 200 MHz) δ 2.2 (m, 8H), 2.6 (m, 2H), 2.9 (m, 1H), 6.4 (t, 1H), 7.4 (m, 4H), 8.7 (s, 1H)

Example 33

[3-(3,4-Difluoro-phenyl)-3-tetrazol-2-yl-propyl]-dimethyl-amine

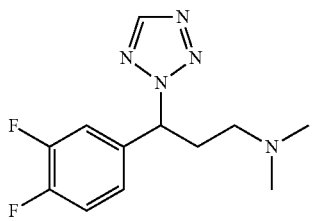

The procedure given in Example 1 was followed using 3,4-difluoroacetophenone as a reactant, instead of 3,4-dichloroacetophenone, to give [3-(3,4-Difluoro-phenyl)-3-tetrazol-2-yl-propyl]-dimethyl-amine.

1H-NMR (CDCl3, 200 MHz) δ 2.2 (m, 8H), 2.6 (m, 2H), 2.9 (m, 1H), 6.0 (t, 1H), 7.4 (m, 4H), 8.4 (s, 1H)

Example 34

[3-(3,4-Difluoro-phenyl)-3-[1,2,3]triazol-1-yl-propyl]-dimethyl-amine

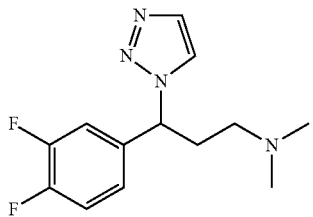 [SMILES: CN(C)CCC(c1ccc(F)c(F)c1)n1ccnn1]

The procedure given in Example 1 was followed using 3,4-difluoroacetophenone and 1H-1,2,3-triazole as reactants, instead of 3,4-dichloroacetophenone and 1H-tetrazole, to give [3-(3,4-Difluoro-phenyl)-3-[1,2,3]triazol-1-yl-propyl]-dimethyl-amine.

1H-NMR (CDCl3, 200 MHz) δ 2.2 (m, 8H), 2.6 (m, 2H), 2.9 (m, 1H), 6.0 (t, 1H), 7.4 (m, 3H), 7.5 (s, 1H), 7.7 (s, 1H)

Example 35

[3-(3,4-Difluoro-phenyl)-3-[1,2,3]triazol-2-yl-propyl]-dimethyl-amine

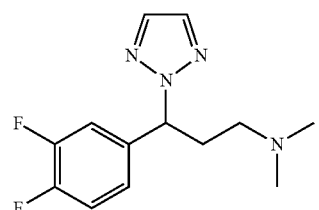

The procedure given in Example 1 was followed using 3,4-difluoroacetophenone and 1H-1,2,3-triazole as reactants, instead of 3,4-dichloroacetophenone and 1H-tetrazole, to give [3-(3,4-Difluoro-phenyl)-3-[1,2,3]triazol-2-yl-propyl]-dimethyl-amine 1H-NMR (CDCl3, 200 MHz) δ 2.2 (m, 8H), 2.6 (m, 2H), 2.9 (m, 1H), 6.0 (t, 1H), 7.4 (m, 3H), 7.6 (s, 2H)

Example 36

[3-(3,4-Dimethyl-phenyl)-3-[1,2,3]triazol-1-yl-propyl]-dimethyl-amine

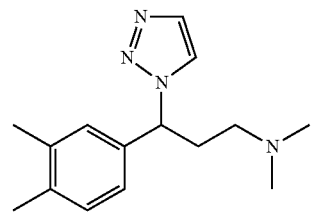

The procedure given in Example 1 was followed using 3,4-dimethylacetophenone and 1H-1,2,3-triazole as reactant, instead of 3,4-dichloroacetophenone, and 1H-tetrazole to give [3-(3,4-Dimethyl-phenyl)-3-[1,2,3]triazol-1-yl-propyl]-dimethyl-amine.

1H-NMR (CDCl3, 200 MHz) δ 2.2 (m, 14H), 2.6 (m, 2H), 2.9 (m, 2H), 6.0 (t, 1H), 7.4 (m, 3H), 7.5 (s, 1H), 7.7 (s, 1H)

Example 37

[3-(3,4-Dimethyl-phenyl)-3-[1,2,3]triazol-2-yl-propyl]-dimethyl-amine

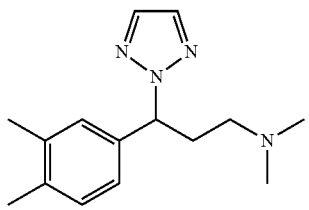

The procedure given in Example 1 was followed using 3,4-dimethylacetophenone and 1H-1,2,3-triazole as reactants, instead of 3,4-dichloroacetophenone and 1H-tetrazole, to give [3-(3,4-Dimethyl-phenyl)-3-[1,2,3]triazol-2-yl-propyl]-dimethyl-amine.

1H-NMR (CDCl3, 200 MHz) δ 2.2 (m, 14H), 2.6 (m, 2H), 2.9 (m, 2H), 6.0 (t, 1H), 7.4 (m, 3H), 7.5 (t, 2H)

Example 38

[3-(3,4-Dimethyl-phenyl)-3-tetrazol-1-yl-propyl]-dimethyl-amine

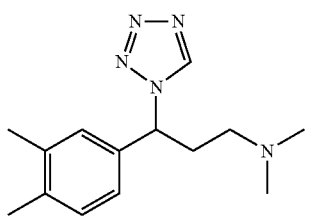

The procedure given in Example 1 was followed using 3,4-dimethylacetophenone as a reactant, instead of 3,4-dichloroacetophenone, to give [3-(3,4-Dimethyl-phenyl)-3-tetrazol-1-yl-propyl]-dimethyl-amine.

1H-NMR (CDCl3, 200 MHz) δ 2.2 (m, 14H), 2.6 (m, 2H), 2.9 (m, 2H), 6.0 (t, 1H), 7.4 (m, 3H), 8.5 (s, 1H)

Example 39

[3-(3,4-Dimethyl-phenyl)-3-tetrazol-2-yl-propyl]-dimethyl-amine

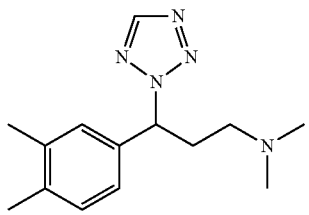

The procedure given in Example 1 was followed using 3,4-dimethylacetophenone as a reactant, instead of 3,4-dichloroacetophenone, to give [3-(3,4-Dimethyl-phenyl)-3-tetrazol-2-yl-propyl]-dimethyl-amine.

1H-NMR (CDCl3, 200 MHz) δ 2.2 (m, 14H), 2.6 (m, 2H), 2.9 (m, 2H), 6.0 (t, 1H), 7.4 (m, 3H), 8.3 (s, 1H)

Example 40

[3-(4-Chloro-phenyl)-3-tetrazol-1-yl-propyl]-dimethyl-amine

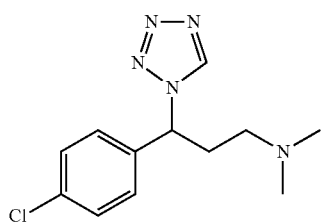 [SMILES: CN(C)CCC(c1ccc(Cl)cc1)n1cnnn1]

The procedure given in Example 1 was followed using 4-chloroacetophenone as a reactant, instead of 3,4-dichloroacetophenone, to give [3-(4-Chloro-phenyl)-3-tetrazol-1-yl-propyl]-dimethyl-amine.

1H-NMR (CDCl3, 200 MHz) δ 2.2 (m, 7H), 2.6 (m, 2H), 2.9 (m, 2H), 6.0 (t, 1H), 7.4 (m, 4H), 8.7 (s, 1H)

Example 41

[3-(4-Chloro-phenyl)-3-tetrazol-2-yl-propyl]-dimethyl-amine

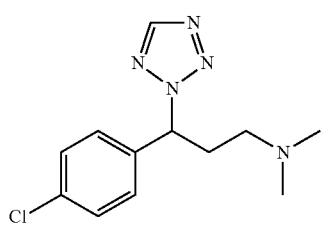 [SMILES: CN(C)CCC(c1ccc(Cl)cc1)n1ncnn1]

The procedure given in Example 1 was followed using 4-chloroacetophenone as a reactant, instead of 3,4-dichloroacetophenone, to give [3-(4-Chloro-phenyl)-3-tetrazol-2-yl-propyl]-dimethyl-amine 1H-NMR (CDCl3, 200 MHz) δ 2.2 (m, 7H), 2.6 (m, 2H), 2.9 (m, 2H), 6.0 (t, 1H), 7.4 (m, 4H), 8.7 (s, 1H)

Example 42

Dimethyl-(3-phenyl-3-[1,2,3]triazol-1-yl-propyl)-amine

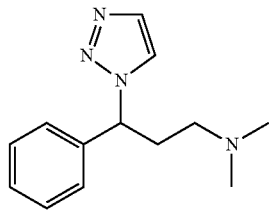 [SMILES: CN(C)CCC(c1ccccc1)n1ccnn1]

The procedure given in Example 1 was followed using acetophenone and 1H-1,2,3-triazole as reactants, instead of 3,4-dichloroacetophenone and 1H-tetrazole, to give Dimethyl-(3-phenyl-3-[1,2,3]triazol-1-yl-propyl)-amine.

1H-NMR (CDCl3, 200 MHz) δ 2.2 (m, 7H), 2.6 (m, 2H), 2.9 (m, 2H), 6.0 (t, 1H), 7.2 (m, 5H), 7.4 (s, 1H), 7.6 (s, 1H)

Example 43

Dimethyl-(3-phenyl-3-[1,2,3]triazol-2-yl-propyl)-amine

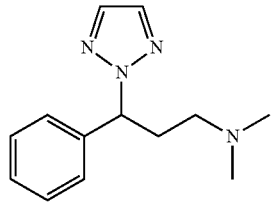 [SMILES: CN(C)CCC(c1ccccc1)n1nccn1]

The procedure given in Example 1 was followed using acetophenone and 1H-1,2,3-triazole as reactants, instead of 3,4-dichloroacetophenone and 1H-tetrazole, to give Dimethyl-(3-phenyl-3-[1,2,3]triazol-2-yl-propyl)-amine.

1H-NMR (CDCl3, 200 MHz) δ 2.2 (m, 7H), 2.6 (m, 2H), 6.0 (t, 1H), 7.2 (m, 5H), 7.4 (s, 2H)

Example 44

[3-(4-Chloro-phenyl)-3-[1,2,3]triazol-1-yl-propyl]-dimethyl-amine

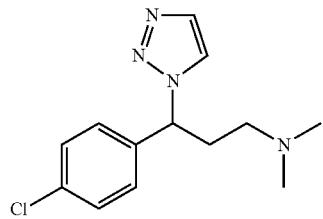 [SMILES: CN(C)CCC(c1ccc(Cl)cc1)n1ccnn1]

The procedure given in Example 1 was followed using 4-chloroacetophenone and 1H-1,2,3-triazole as reactant, instead of 3,4-dichloroacetophenone and 1H-tetrazole, to give [3-(4-Chloro-phenyl)-3-[1,2,3]triazol-1-yl-propyl]-dimethyl-amine.

1H-NMR (CDCl3, 200 MHz) δ 2.2 (m, 7H), 2.6 (m, 2H), 6.0 (t, 1H), 7.2 (m, 4H), 7.5 (s, 1H), 7.7 (s, 1H)

Example 45

[3-(4-Chloro-phenyl)-3-[1,2,3]triazol-2-yl-propyl]-dimethyl-amine

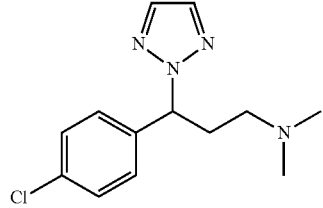 [SMILES: CN(C)CCC(c1ccc(Cl)cc1)n1nccn1]

The procedure given in Example 1 was followed using 4-chloroacetophenone and 1H-1,2,3-triazole as reactants, instead of 3,4-dichloroacetophenone and 1H-tetrazole, to give [3-(4-Chloro-phenyl)-3-[1,2,3]triazol-2-yl-propyl]-dimethyl-amine.

1H-NMR (CDCl3, 200 MHz) δ 2.2 (m, 7H), 2.6 (m, 2H), 6.0 (t, 1H), 7.2 (m, 4H), 7.6 (s, 2H)

Example 46

[3-(3,4-Dichloro-phenyl)-3-[1,2,3]triazol-2-yl-propyl]-dimethyl-amine

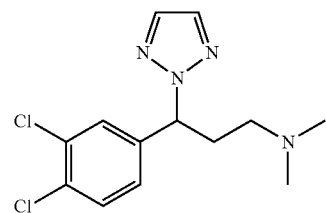 [SMILES: CN(C)CCC(c1ccc(Cl)c(Cl)c1)n1nccn1]

The procedure given in Example 1 was followed using 1H-1,2,3-triazole as a reactant, instead of 1H-tetrazole, to give [3-(3,4-Dichloro-phenyl)-3-[1,2,3]triazol-2-yl-propyl]-dimethyl-amine.

1H-NMR (CDCl3, 200 MHz) δ 2.2 (m, 7H), 2.4 (m, 2H), 2.6 (m, 2H), 6.0 (t, 1H), 7.2 (dd, 1H), 7.4 (dd, 2H), 7.6 (s, 2H)

Example 47

[3-(3,4-Dichloro-phenyl)-3-imidazol-1-yl-propyl]-dimethyl-amine

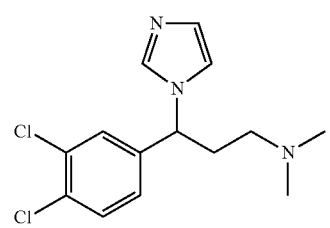 [SMILES: CN(C)CCC(c1ccc(Cl)c(Cl)c1)n1ccnc1]

The procedure given in Example 1 was followed using imidazole as a reactant, instead of 1H-tetrazole, to give [3-(3,4-Dichloro-phenyl)-3-imidazol-1-yl-propyl]-dimethyl-amine.

1H-NMR (CDCl3, 200 MHz) δ 2.2 (br, 10H), 5.3 (t, 1H), 7.2 (dd, 1H), 7.4 (dd, 2H), 7.6 (s, 2H)

Example 48

[3-(3-Methoxy-naphthalen-2-yl)-3-tetrazol-2-yl-propyl]-dimethyl-amine

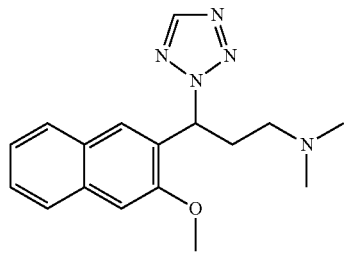 [SMILES: COc1cc2ccccc2cc1C(CCN(C)C)n1ncnn1]

The procedure given in Example 1 was followed using 1-(3-Methoxy-naphthalen-2-yl)-ethanone as reactants, instead of 3,4-dichloroacetophenone, to give [3-(3-Methoxy-naphthalen-2-yl)-3-tetrazol-2-yl-propyl]-dimethyl-amine.

1H-NMR (CDCl3, 200 MHz) δ 2.4 (m, 13H), 6.2 (m, 1H), 7.5 (m, 3H), 7.8 (m, 4H), 8.5 (s, 1H)

Example 49

[3-(3-Methoxy-naphthalen-2-yl)-3-(5-methyl-tetrazol-2-yl)-propyl]-dimethyl-amine

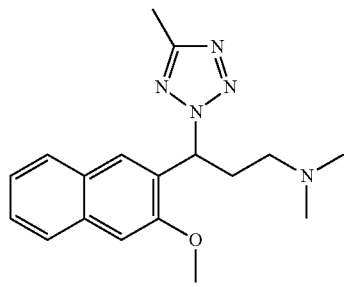 [SMILES: COc1cc2ccccc2cc1C(CCN(C)C)n1nnc(C)n1]

The procedure given in Example 1 was followed using 1-(3-Methoxy-naphthalen-2-yl)-ethanone and 5-Methyl-1H-tetrazole as reactants, instead of 3,4-dichloroacetophenone and 1H-tetrazole, to give [3-(3-Methoxy-naphthalen-2-yl)-3-(5-methyl-tetrazol-2-yl)-propyl]-dimethyl-amine.

1H-NMR (CDCl3, 200 MHz) δ 2.4 (m, 9H), 2.5 (m, 5H), 2.8 (m, 1H), 4.0 (s, 3H), 6.6 (m, 1H), 7.5 (m, 3H), 7.8 (m, 4H)

Example 50

[3-(6-Fluoro-naphthalen-2-yl)-3-tetrazol-2-yl-propyl]-dimethyl-amine

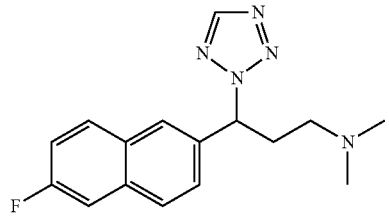 [SMILES: CN(C)CCC(c1ccc2cc(F)ccc2c1)n1ncnn1]

The procedure given in Example 1 was followed using 1-(6-Fluoro-naphthalen-2-yl)-ethanone as reactants, instead of 3,4-dichloroacetophenone, to give [3-(6-Fluoro-naphthalen-2-yl)-3-tetrazol-2-yl-propyl]-dimethyl-amine.

1H-NMR (CDCl3, 200 MHz) δ 2.4 (m, 12H), 2.5 (m, 1H), 2.8 (m, 1H), 6.2 (m, 1H), 7.2 (m, 1H), 7.4 (m, 1H), 7.5 (m, 1H), 7.8 (m, 3H), 8.5 (s, 1H)

Example 51

[3-(6-Fluoro-naphthalen-2-yl)-3-(5-methyl-tetrazol-2-yl)-propyl]-dimethyl-amine

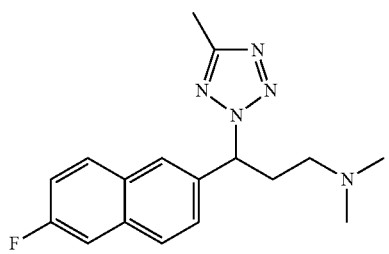 [SMILES: Cc1nnn(C(CCN(C)C)c2ccc3cc(F)ccc3c2)n1]

The procedure given in Example 1 was followed using 1-(6-Fluoro-naphthalen-2-yl)-ethanone and 5-Me-1H-tetrazole as reactants, instead of 3,4-dichloroacetophenone and 1H-tetrazole, to give [3-(6-Fluoro-naphthalen-2-yl)-3-(5-methyl-tetrazol-2-yl)-propyl]-dimethyl-amine 1H-NMR (CDCl3, 200 MHz) δ 2.4 (m, 9H), 2.5 (m, 4H), 2.8 (m, 1H), 6.2 (t, 1H), 7.2 (m, 1H), 7.4 (m, 1H), 7.5 (m, 1H), 7.8 (m, 3H)

Example 52

[3-(1,4-Dimethoxy-naphthalen-2-yl)-3-tetrazol-2-yl-propyl]-dimethyl-amine

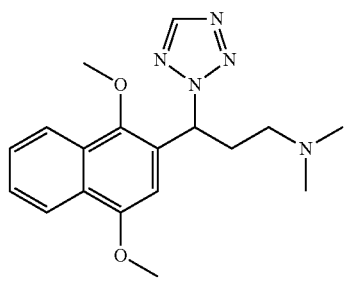 [SMILES: COc1cc(C(CCN(C)C)n2ncnn2)c(OC)c2ccccc12]

The procedure given in Example 1 was followed using 1-(1,4-Dimethoxy-naphthalen-2-yl)-ethanone as reactants, instead of 3,4-dichloroacetophenone, to give [3-(1,4-Dimethoxy-naphthalen-2-yl)-3-tetrazol-2-yl-propyl]-dimethyl-amine.

1H-NMR (CDCl3, 200 MHz) δ 2.4 (m, 12H), 2.5 (m, 1H), 2.8 (m, 1H), 4.0 (d, 6H), 6.2 (m, 1H), 7.2 (m, 1H), 7.4 (m, 1H), 7.5 (m, 1H), 7.8 (m, 2H), 8.5 (s, 1H)

Example 53

[3-(1,4-Dimethoxy-naphthalen-2-yl)-3-(5-methyl-tetrazol-2-yl)-propyl]-dimethyl-amine

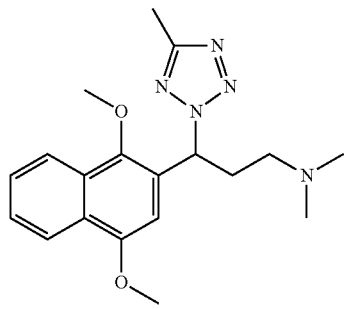 [SMILES: COc1cc(C(CCN(C)C)n2nnc(C)n2)c(OC)c2ccccc12]

The procedure given in Example 1 was followed using 1-(1,4-Dimethoxy-naphthalen-2-yl)-ethanone and 5-Me-1H-tetrazole as reactants, instead of 3,4-dichloroacetophenone and 1H-tetrazole, to give [3-(1,4-Dimethoxy-naphthalen-2-yl)-3-(5-methyl-tetrazol-2-yl)-propyl]-dimethyl-amine 1H-NMR (CDCl3, 200 MHz) δ 2.4 (m, 12H), 2.5 (m, 1H), 2.8 (m, 1H), 4.0 (d, 6H), 6.2 (m, 1H), 6.9 (s, 1H), 7.5 (m, 2H), 8.0 (s, 1H), 8.2 (d, 1H)

Example 54

[3-(3,5-Dimethoxy-naphthalen-2-yl)-3-tetrazol-2-yl-propyl]-dimethyl-amine

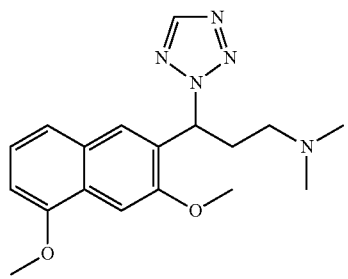 [SMILES: COc1cc2c(OC)cccc2cc1C(CCN(C)C)n1ncnn1]

The procedure given in Example 1 was followed using 1-(3,5-Dimethoxy-naphthalen-2-yl)-ethanone as reactants, instead of 3,4-dichloroacetophenone, to give [3-(3,5-Dimethoxy-naphthalen-2-yl)-3-tetrazol-2-yl-propyl]-dimethyl-amine.

1H-NMR (CDCl3, 200 MHz) δ 2.4 (m, 12H), 2.5 (m, 1H), 2.8 (m, 1H), 4.0 (m, 6H), 6.8 (m, 1H), 7.3 (s, 6H), 7.5 (m, 2H), 8.5 (s, 1H)

Example 55

[3-(3,5-Dimethoxy-naphthalen-2-yl)-3-(5-methyl-tetrazol-2-yl)-propyl]-dimethyl-amine

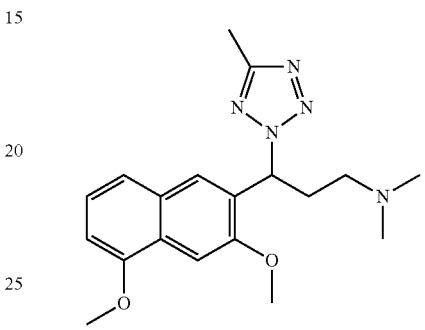

The procedure given in Example 1 was followed using 1-(3,5-Dimethoxy-naphthalen-2-yl)-ethanone and 5-Me-1H-tetrazole as reactants, instead of 3,4-dichloroacetophenone and 1H-tetrazole, to give [3-(3,5-Dimethoxy-naphthalen-2-yl)-3-(5-methyl-tetrazol-2-yl)-propyl]-dimethyl-amine.

1H-NMR (CDCl3, 200 MHz) δ 2.4 (m, 9H), 2.5 (m, 4H), 2.8 (m, 1H), 4.0 (m, 6H), 6.6 (m, 1H), 6.8 (m, 1H), 7.2 (s, 3H), 7.5 (s, 1H), 7.7 (s, 1H)

Example 56

[3-(3,5-Dimethoxy-naphthalen-2-yl)-3-tetrazol-1-yl-propyl]-dimethyl-amine

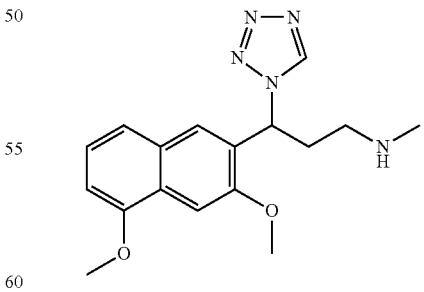

The procedure given in Example 1 was followed using 1-(3,5-Dimethoxy-naphthalen-2-yl)-ethanone as reactants, instead of 3,4-dichloroacetophenone, to give [3-(3,5-Dimethoxy-naphthalen-2-yl)-3-tetrazol-1-yl-propyl]-dimethyl-amine 1H-NMR (CDCl3, 200 MHz) δ 2.4 (m, 12H), 2.5 (m, 1H), 2.8 (m, 1H), 4.0 (m, 6H), 6.6 (m, 1H), 6.8 (m, 1H), 7.2 (s, 3H), 7.5 (s, 1H), 7.7 (s, 1H), 8.7 (s, 1H)

Example 57

Dimethyl-[3-(4-methyl-naphthalen-1-yl)-3-tetrazol-2-yl-propyl]-amine

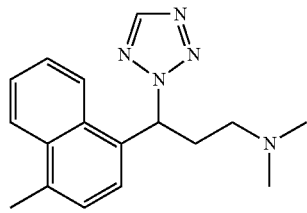

The procedure given in Example 1 was followed using 1-(4-Methyl-naphthalen-1-yl)-ethanone as reactants, instead of 3,4-dichloroacetophenone, to give Dimethyl-[3-(4-methyl-naphthalen-1-yl)-3-tetrazol-2-yl-propyl]-amine.

1H-NMR (CDCl3, 200 MHz) δ 2.2 (m, 10H), 2.4 (m, 1H), 2.8 (m, 4H), 3.0 (m, 1H), 7.0 (m, 1H), 7.2 (m, 1H), 7.5 (m, 4H), 8.0 (m, 1H), 8.3 (m, 1H), 8.5 (s, 1H)

Example 58

Dimethyl-[3-(4-methyl-naphthalen-1-yl)-3-(5-methyl-tetrazol-2-yl)-propyl]-amine

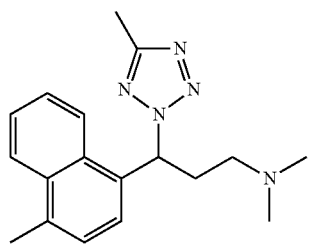

The procedure given in Example 1 was followed using 1-(4-Methyl-naphthalen-1-yl)-ethanone and 5-Me-1H-tetrazole as reactants, instead of 3,4-dichloroacetophenone and 1H-tetrazole, to give Dimethyl-[3-(4-methyl-naphthalen-1-yl)-3-(5-methyl-tetrazol-2-yl)-propyl]-amine.

1H-NMR (CDCl3, 200 MHz) δ 2.2 (m, 9H), 2.4 (m, 3H), 2.8 (m, 3H), 3.0 (m, 1H), 7.0 (m, 1H), 7.2 (m, 1H), 7.5 (m, 4H), 8.0 (m, 1H), 8.3 (m, 1H)

Example 59

[3-(4-Fluoro-naphthalen-1-yl)-3-tetrazol-2-yl-propyl]-dimethyl-amine

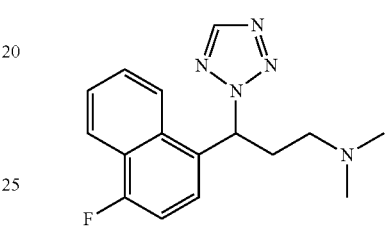

The procedure given in Example 1 was followed using 1-(4-Fluoro-naphthalen-1-yl)-ethanone as reactants, instead of 3,4-dichloroacetophenone, to give [3-(4-Fluoro-naphthalen-1-yl)-3-tetrazol-2-yl-propyl]-dimethyl-amine.

1H-NMR (CDCl3, 200 MHz) δ 2.2 (m, 12H), 2.4 (m, 1H), 2.8 (m, 1H), 7.0 (m, 1H), 7.2 (m, 1H), 7.5 (m, 4H), 8.0 (m, 1H), 8.3 (m, 1H), 8.5 (s, 1H)

Example 60

[3-(4-Fluoro-naphthalen-1-yl)-3-(5-methyl-tetrazol-2-yl)-propyl]-dimethyl-amine

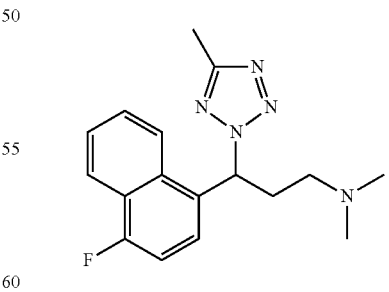

The procedure given in Example 1 was followed using 1-(4-Methyl-naphthalen-1-yl)-ethanone and 5-Me-1H-tetrazole as reactants, instead of 3,4-dichloroacetophenone and 1H-tetrazole, to give [3-(4-Fluoro-naphthalen-1-yl)-3-(5-methyl-tetrazol-2-yl)-propyl]-dimethylamine.

1H-NMR (CDCl3, 200 MHz) δ 2.2 (m, 9H), 2.4 (m, 4H), 2.8 (m, 1H), 7.0 (m, 1H), 7.2 (m, 1H), 7.5 (m, 3H), 8.1 (m, 1H), 8.3 (m, 1H)

Example 61

(3-Isoquinolin-1-yl-3-tetrazol-2-yl-propyl)-dimethyl-amine

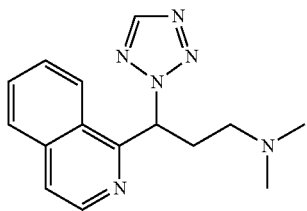 [SMILES: CN(C)CCC(c1nccc2ccccc12)n1ncnn1]

The procedure given in Example 1 was followed using 1-Isoquinolin-1-yl-ethanone as reactants, instead of 3,4-dichloroacetophenone, to give (3-Isoquinolin-1-yl-3-tetrazol-2-yl-propyl)-dimethyl-amine.

1H-NMR (CDCl3, 200 MHz) δ 2.2 (m, 9H), 2.4 (m, 1H), 2.8 (m, 1H), 7.2 (m, 1H), 7.6 (m, 2H), 7.8 (m, 2H), 8.4 (m, 1H), 8.5 (m, 1H), 9.1 (s, 1H)

Example 62

[3-Isoquinolin-1-yl-3-(5-methyl-tetrazol-2-yl-propyl]-dimethyl-amine

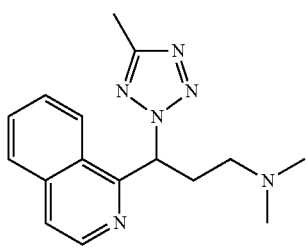 [SMILES: Cc1nnn(C(CCN(C)C)c2nccc3ccccc23)n1]

The procedure given in Example 1 was followed using 1-Isoquinolin-1-yl-ethanone and 5-Me-1H-tetrazole as reactants, instead of 3,4-dichloroacetophenone and 1H-tetrazole, to give [3-Isoquinolin-1-yl-3-(5-methyl-tetrazol-2-yl)-propyl]-dimethyl-amine 1H-NMR (CDCl3, 200 MHz) δ 2.2 (m, 9H), 2.5 (m, 3H), 2.8 (m, 3H), 7.2 (m, 1H), 7.6 (m, 2H), 7.8 (m, 2H), 8.4 (m, 1H), 8.5 (m, 1H)

Example 63

(3-Benzo[1,3]dioxol-5-yl-3-tetrazol-2-yl-propyl)-dimethyl-amine

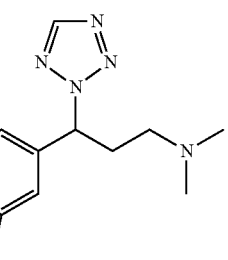

The procedure given in Example 1 was followed using 1-Benzo[1,3]dioxol-5-yl-ethanone as reactants, instead of 3,4-dichloroacetophenone, to give (3-Benzo[1,3]dioxol-5-yl-3-tetrazol-2-yl-propyl)-dimethyl-amine.

1H-NMR (CDCl3, 200 MHz) δ 2.2 (m, 9H), 2.5 (m, 1H), 2.8 (m, 1H), 6.0 (s, 2H), 6.1 (m, 1H), 6.8 (d, 1H), 7.0 (d, 2H), 8.5 (m, 1H)

Example 64

[3-Benzo[1,3]dioxol-5-yl-3-(5-methyl-tetrazol-2-yl)-propyl]-dimethyl-amine

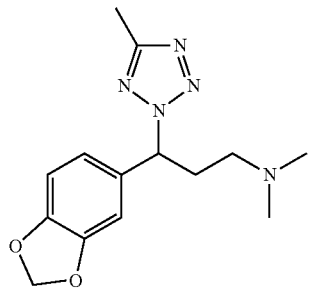 [SMILES: Cc1nnn(C(CCN(C)C)c2ccc3c(c2)OCO3)n1]

The procedure given in Example 1 was followed using 1-Benzo[1,3]dioxol-5-yl-ethanone and 5-Me-1H-tetrazole as reactants, instead of 3,4-dichloroacetophenone and 1H-tetrazole, to give [3-Benzo[1,3]dioxol-5-yl-3-(5-methyl-tetrazol-2-yl)-propyl]-dimethyl-amine.

1H-NMR (CDCl3, 200 MHz) δ 2.2 (m, 15H), 2.8 (m, 1H), 6.0 (s, 2H), 6.1 (m, 1H), 6.8 (d, 1H), 7.0 (d, 2H), 8.5 (m, 1H)

Example 65

[3-Benzo[1,3]dioxol-5-yl-3-(5-methyl-tetrazol-1-yl)-propyl]-dimethyl-amine

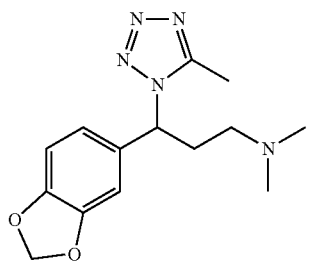 [SMILES: Cc1nnnn1C(CCN(C)C)c1ccc2c(c1)OCO2]

The procedure given in Example 1 was followed using 1-Benzo[1,3]dioxol-5-yl-ethanone and 5-Me-1H-tetrazole as reactants, instead of 3,4-dichloroacetophenone and 1H-tetrazole, to give [3-Benzo[1,3]dioxol-5-yl-3-(5-methyl-tetrazol-1-yl)-propyl]-dimethyl-amine.

1H-NMR (CDCl3, 200 MHz) δ 2.2 (m, 9H), 2.4 (m, 1H), 2.5 (s, 3H), 2.8 (m, 1H), 5.5 (t, 2H), 6.1 (s, 2H), 6.8 (m, 3H)

Example 66

[3-(3,4-Dimethoxy-phenyl)-3-tetrazol-2-yl-propyl]-dimethyl-amine

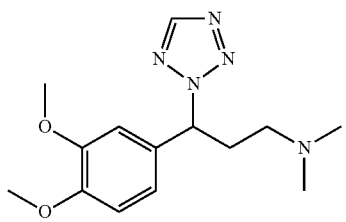

The procedure given in Example 1 was followed using 1-(3,4-Dimethoxy-phenyl)-ethanone as reactants, instead of 3,4-dichloroacetophenone, to give [3-(3,4-Dimethoxy-phenyl)-3-tetrazol-2-yl-propyl]-dimethyl-amine.

1H-NMR (CDCl3, 200 MHz) δ 2.2 (s, 12H), 2.4 (m, 1H), 2.8 (m, 1H), 4.0 (s, 6H), 6.1 (s, 2H), 6.8 (d, 1H), 7.0 (d, 2H), 8.5 (s, 1H)

Example 67

[3-(2,3-Dihydro-benzo[1,4]dioxin-2-yl)-3-tetrazol-2-yl-propyl]-dimethyl-amine

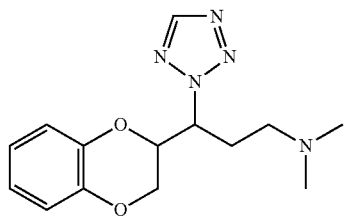 [SMILES: CN(C)CCC(C1COc2ccccc2O1)n1ncnn1]

The procedure given in Example 1 was followed using 1-(2,3-Dihydro-benzo[1,4]dioxin-2-yl)-ethanone as reactants, instead of 3,4-dichloroacetophenone, to give [3-(2,3-Dihydro-benzo[1,4]dioxin-2-yl)-3-tetrazol-2-yl-propyl]-dimethyl-amine.

1H-NMR (CDCl3, 200 MHz) δ 2.2 (s, 12H), 2.4 (m, 3H), 3.8 (m, 1H), 4.6 (m, 1H), 5.4 (m, 1H), 7.0 (s, 5H), 8.5 (s, 1H)

Example 68

[3-(2,3-Dihydro-benzo[1,4]dioxin-2-yl)-3-(5-methyl-tetrazol-2-yl)-propyl]-dimethyl-amine

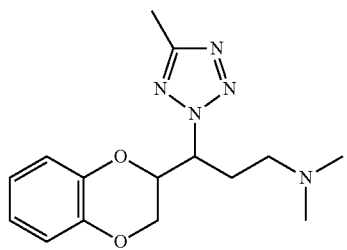 [SMILES: Cc1nnn(C(CCN(C)C)C2COc3ccccc3O2)n1]

The procedure given in Example 1 was followed using 1-(2,3-Dihydro-benzo[1,4]dioxin-2-yl)-ethanone and 5-Me-1H-tetrazole as reactants, instead of 3,4-dichloroacetophenone and 1H-tetrazole, to give [3-(2,3-Dihydro-benzo[1,4]dioxin-2-yl)-3-(5-methyl-tetrazol-2-yl)-propyl]-dimethyl-amine.

1H-NMR (CDCl3, 200 MHz) δ 2.2 (s, 10H), 2.4 (m, 3H), 2.8 (m, 4H), 3.8 (m, 1H), 4.0 (m, 1H), 4.8 (m, 1H), 5.3 (m, 1H), 7.0 (s, 4H)

Example 69

Dimethyl-(3-quinolin-2-yl-3-tetrazol-2-yl-propyl)-amine

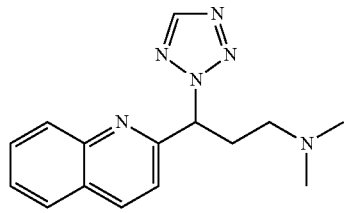

The procedure given in Example 1 was followed using 1-Quinolin-2-yl-ethanone as reactants, instead of 3,4-dichloroacetophenone, to give Dimethyl-(3-quinolin-2-yl-3-tetrazol-2-yl-propyl)-amine.

1H-NMR (CDCl3, 200 MHz) δ 2.2 (s, 10H), 2.8 (m, 2H), 6.5 (t, 1H), 7.3 (m, 2H), 7.5 (m, 1H), 7.8 (m, 2H), 8.0 (t, 2H), 8.5 (s, 1H)

Example 70

Dimethyl-[3-(5-methyl-tetrazol-2-yl)-3-quinolin-2-yl-propyl]-amine

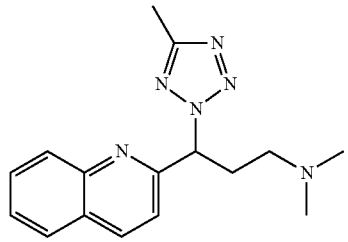

The procedure given in Example 1 was followed using 1-Quinolin-2-yl-ethanone and 5-Me-1H-tetrazole as reactants, instead of 3,4-dichloroacetophenone and 1H-tetrazole, to give Dimethyl-[3-(5-methyl-tetrazol-2-yl)-3-quinolin-2-yl-propyl]-amine.

1H-NMR (CDCl3, 200 MHz) δ 2.2 (s, 10H), 2.5 (s, 3H), 2.8 (m, 2H), 6.5 (t, 1H), 7.3 (m, 2H), 7.5 (m, 1H), 7.8 (m, 2H), 8.0 (t, 2H), 8.5 (s, 1H)

Example 71

Dimethyl-[3-(1-methyl-1H-indol-2-yl)-3-tetrazol-2-yl-propyl]-amine

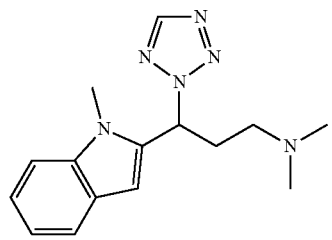 [SMILES: CN(C)CCC(c1cc2ccccc2n1C)n1ncnn1]

The procedure given in Example 1 was followed using 1-(1-Methyl-1H-indol-2-yl)-ethanone as reactants, instead of 3,4-dichloroacetophenone, to give Dimethyl-[3-(1-methyl-1H-indol-2-yl)-3-tetrazol-2-yl-propyl]-amine 1H-NMR (CDCl3, 200 MHz) δ 2.2 (s, 10H), 2.5 (s, 3H), 2.8 (m, 2H), 6.5 (t, 1H), 7.3 (m, 2H), 7.5 (m, 1H), 7.8 (m, 2H), 8.0 (t, 2H), 8.5 (s, 1H)

Example 72

Dimethyl-[3-(1-methyl-1H-indol-2-yl)-3-(5-methyl-tetrazol-2-yl)-propyl]-amine

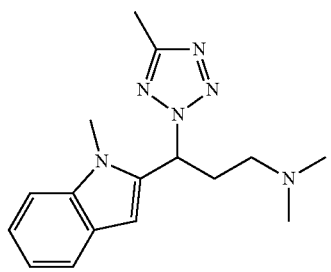 [SMILES: Cc1nnn(C(CCN(C)C)c2cc3ccccc3n2C)n1]

The procedure given in Example 1 was followed using 1-(1-Methyl-1H-indol-2-yl)-ethanone and 5-Me-1H-tetrazole as reactants, instead of 3,4-dichloroacetophenone and 1H-tetrazole, to give Dimethyl-[3-(1-methyl-1H-indol-2-yl)-3-(5-methyl-tetrazol-2-yl)-propyl]-amine.

1H-NMR (CDCl3, 200 MHz) δ 2.2 (s, 8H), 2.5 (s, 3H), 2.8 (m, 2H), 3.8 (s, 2H), 6.5 (t, 1H), 6.8 (s, 1H), 7.3 (m, 1H), 7.5 (m, 2H), 7.8 (m, 2H)

Example 73

Dimethyl-[3-(1,2,3,4-tetrahydro-naphthalen-2-yl)-3-tetrazol-2-yl-propyl]-amine

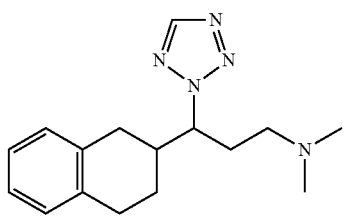

The procedure given in Example 1 was followed using 1-(1,2,3,4-Tetrahydro-naphthalen-2-yl)-ethanone as reactants, instead of 3,4-dichloroacetophenone, to give Dimethyl-[3-(1,2,3,4-tetrahydro-naphthalen-2-yl)-3-tetrazol-2-yl-propyl]-amine.

1H-NMR (CDCl3, 200 MHz) δ 2.2 (s, 11H), 2.8 (m, 8H), 5.0 (m, 1H), 7.0 (m, 4H), 8.5 (s, 1H)

Example 74

[3-(6-Chloro-pyridin-3-yl)-3-tetrazol-2-yl-propyl]-dimethyl-amine

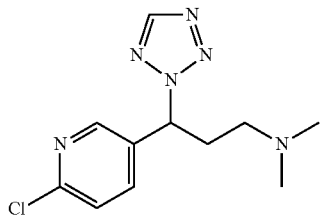 [SMILES: CN(C)CCC(c1ccc(Cl)nc1)n1ncnn1]

The procedure given in Example 1 was followed using 1-(6-Chloro-pyridin-3-yl)-ethanone as reactants, instead of 3,4-dichloroacetophenone, to give [3-(6-Chloro-pyridin-3-yl)-3-tetrazol-2-yl-propyl]-dimethyl-amine.

1H-NMR (CDCl3, 200 MHz) δ 2.2 (m, 10H), 2.5 (m, 1H), 2.8 (m, 1H), 6.2 (m, 1H), 7.2 (m, 1H), 7.8 (m, 1H), 8.5 (s, 1H)

Example 75

(3-Benzo[b]thiophen-2-yl-3-tetrazol-2-yl-propyl)-dimethyl-amine

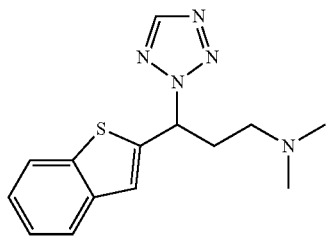 [SMILES: CN(C)CCC(c1cc2ccccc2s1)n1ncnn1]

The procedure given in Example 1 was followed using 1-Benzo[b]thiophen-2-yl-ethanone as reactants, instead of 3,4-dichloroacetophenone, to give (3-Benzo[b]thiophen-2-yl-3-tetrazol-2-yl-propyl)-dimethyl-amine.

1H-NMR (CDCl3, 200 MHz) δ 2.2 (m, 10H), 2.8 (m, 1H), 6.5 (m, 1H), 7.4 (m, 3H), 7.8 (m, 2H), 8.5 (s, 1H)

Example 76

[3-Benzo[b]thiophen-2-yl-3-(5-methyl-tetrazol-2-yl)-propyl]-dimethyl-amine

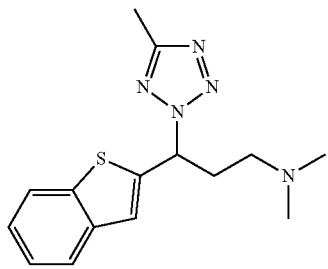 [SMILES: Cc1nnn(C(CCN(C)C)c2cc3ccccc3s2)n1]

The procedure given in Example 1 was followed using 1-Benzo[b]thiophen-2-yl-ethanone and 5-Me-1H-tetrazole as reactants, instead of 3,4-dichloroacetophenone and 1H-tetrazole, to give [3-Benzo[b]thiophen-2-yl-3-(5-methyl-tetrazol-2-yl)-propyl]-dimethyl-amine.

1H-NMR (CDCl3, 200 MHz) δ 2.2 (m, 9H), 2.8 (m, 5H), 6.5 (m, 1H), 7.4 (m, 3H), 7.8 (m, 2H)

Example 77

(3-Benzofuran-2-yl-3-tetrazol-2-yl-propyl)-dimethyl-amine

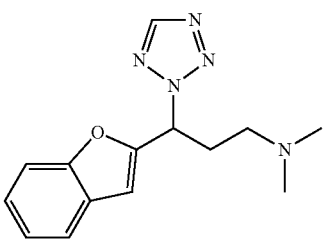 [SMILES: CN(C)CCC(c1cc2ccccc2o1)n1ncnn1]

The procedure given in Example 1 was followed using 1-Benzofuran-2-yl-ethanone as reactants, instead of 3,4-dichloroacetophenone, to give (3-Benzofuran-2-yl-3-tetrazol-2-yl-propyl)-dimethyl-amine.

1H-NMR (CDCl3, 200 MHz) δ 2.2 (m, 10H), 2.8 (m, 2H), 6.5 (m, 1H), 7.4 (m, 3H), 7.8 (m, 2H), 8.5 (s, 1H)

Example 78

[3-Benzofuran-2-yl-3-(5-methyl-tetrazol-2-yl)-propyl]-dimethyl-amine

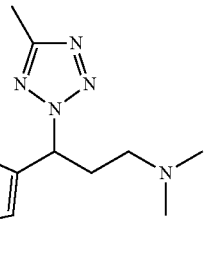

The procedure given in Example 1 was followed using 1-Benzofuran-2-yl-ethanone and 5-Me-1H-tetrazole as reactants, instead of 3,4-dichloroacetophenone and 1H-tetrazole, to give [3-Benzofuran-2-yl-3-(5-methyl-tetrazol-2-yl)-propyl]-dimethyl-amine.

1H-NMR (CDCl3, 200 MHz) δ 2.2 (m, 10H), 2.8 (m, 2H), 6.5 (m, 1H), 7.4 (m, 3H), 7.8 (m, 2H)

Example 79

(3-Benzofuran-2-yl-3-tetrazol-1-yl-propyl)-dimethyl-amine

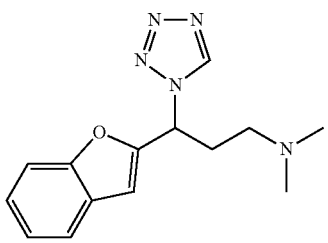 [SMILES: CN(C)CCC(c1cc2ccccc2o1)n1cnnn1]

The procedure given in Example 1 was followed using 1-Benzofuran-2-yl-ethanone as reactants, instead of 3,4-dichloroacetophenone, to give (3-Benzofuran-2-yl-3-tetrazol-1-yl-propyl)-dimethyl-amine 1H-NMR (CDCl3, 200 MHz) δ 2.2 (m, 10H), 2.8 (m, 2H), 6.2 (m, 1H), 7.4 (m, 3H), 7.8 (m, 2H)

Example 80

[3-(3,4-Difluoro-phenyl)-3-(5-methyl-tetrazol-2-yl)-propyl]-dimethyl-amine

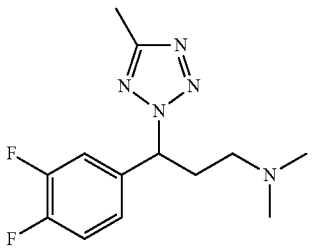

The procedure given in Example 1 was followed using 1-Benzofuran-2-yl-ethanone and 5-Me-1H-tetrazole as reactants, instead of 3,4-dichloroacetophenone and 1H-tetrazole, to give [3-(3,4-Difluoro-phenyl)-3-(5-methyl-tetrazol-2-yl)-propyl]-dimethyl-amine.

1H-NMR (CDCl3, 200 MHz) δ 2.2 (m, 10H), 2.8 (m, 4H), 6.2 (m, 1H), 7.4 (m, 4H)

Example 81

Dimethyl-[3-tetrazol-2-yl-3-(2,4,5-trifluoro-phenyl)-propyl]-amine

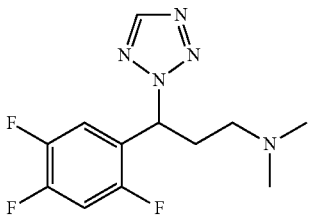

The procedure given in Example 1 was followed using 1-(2,4,5-Trifluoro-phenyl)-ethanone as reactants, instead of 3,4-dichloroacetophenone, to give Dimethyl-[3-tetrazol-2-yl-3-(2,4,5-trifluoro-phenyl)-propyl]-amine.

1H-NMR (CDCl3, 200 MHz) δ 2.2 (m, 12H), 2.8 (m, 2H), 6.5 (m, 1H), 7.0 (m, 1H), 7.4 (m, 1H), 8.6 (s, 1H)

Example 82

Dimethyl-[3-(5-methyl-tetrazol-2-yl)-3-(2,4,5-trifluoro-phenyl)-propyl]-amine

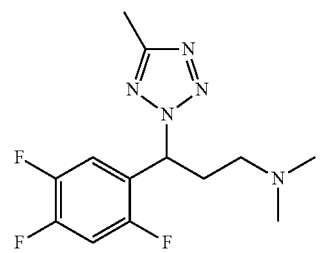 [SMILES: Cc1nnn(C(CCN(C)C)c2cc(F)c(F)cc2F)n1]

The procedure given in Example 1 was followed using 1-(2,4,5-Trifluoro-phenyl)-ethanone and 5-Me-1H-tetrazole as reactants, instead of 3,4-dichloroacetophenone and 1H-tetrazole, to give Dimethyl-[3-(5-methyl-tetrazol-2-yl)-3-(2,4,5-trifluoro-phenyl)-propyl]-amine.

1H-NMR (CDCl3, 200 MHz) δ 2.2 (m, 12H), 2.8 (m, 4H), 6.5 (m, 1H), 7.0 (m, 1H), 7.4 (m, 1H)

Example 83

[3-(3-Bromo-4-fluoro-phenyl)-3-tetrazol-2-yl-propyl]-dimethyl-amine

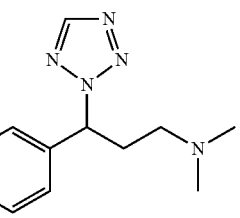

The procedure given in Example 1 was followed using 1-(3-Bromo-4-fluoro-phenyl)-ethanone as reactants, instead of 3,4-dichloroacetophenone, to give [3-(3-Bromo-4-fluoro-phenyl)-3-tetrazol-2-yl-propyl]-dimethyl-amine 1H-NMR (CDCl3, 200 MHz) δ 2.2 (m, 10H), 2.4 (m, 2H), 2.8 (m, 1H), 6.5 (m, 1H), 7.0 (m, 1H), 7.4 (m, 1H), 7.8 (m, 1H), 8.5 (s, 1H)

Example 84

[3-(3-Bromo-4-fluoro-phenyl)-3-(5-methyl-tetrazol-2-yl)-propyl]-dimethyl-amine

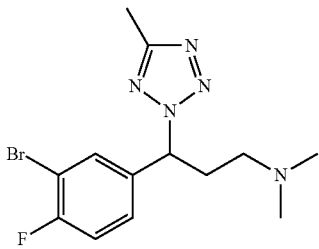

The procedure given in Example 1 was followed using 1-(3-Bromo-4-fluoro-phenyl)-ethanone and 5-Me-1H-tetrazole as reactants, instead of 3,4-dichloroacetophenone and 1H-tetrazole, to give [3-(3-Bromo-4-fluoro-phenyl)-3-(5-methyl-tetrazol-2-yl)-propyl]-dimethyl-amine.

1H-NMR (CDCl3, 200 MHz) δ 2.2 (m, 10H), 2.4 (m, 2H), 2.8 (m, 1H), 6.5 (m, 1H), 7.0 (m, 1H), 7.4 (m, 1H), 7.8 (m, 1H)

Example 85

[3-(6-Methoxy-naphthalen-2-yl)-3-(5-methyl-tetrazol-2-yl)-propyl]-dimethyl-amine

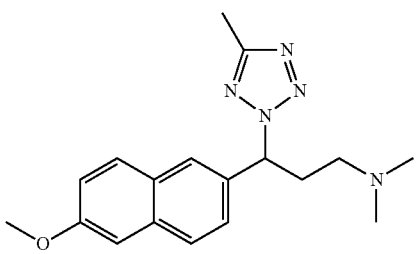

The procedure given in Example 1 was followed using 1-(6-Methoxy-naphthalen-2-yl)-ethanone and 5-Me-1H-tetrazole as reactants, instead of 3,4-dichloroacetophenone and 1H-tetrazole, to give [3-(6-Methoxy-naphthalen-2-yl)-3-(5-methyl-tetrazol-2-yl)-propyl]-dimethyl-amine.

1H-NMR (CDCl3, 200 MHz) δ 2.2 (m, 11H), 2.4 (m, 2H), 2.8 (m, 1H), 4.0 (s, 3H), 6.3 (m, 1H), 7.1 (m, 3H), 7.4 (m, 1H), 7.8 (m, 1H)

Example 86

Dimethyl-[3-(5-methyl-tetrazol-2-yl)-3-(4-phenoxy-phenyl)-propyl]-amine

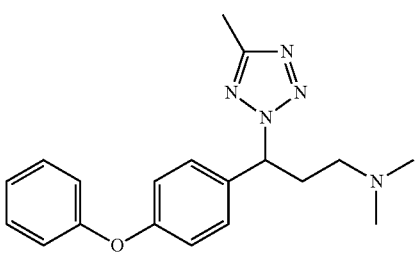 [SMILES: Cc1nnn(C(CCN(C)C)c2ccc(Oc3ccccc3)cc2)n1]

The procedure given in Example 1 was followed using 1-(4-Phenoxy-phenyl)-ethanone and 5-Me-1H-tetrazole as reactants, instead of 3,4-dichloroacetophenone and 1H-tetrazole, to give Dimethyl-[3-(5-methyl-tetrazol-2-yl)-3-(4-phenoxy-phenyl)-propyl]-amine.

1H-NMR (CDCl3, 200 MHz) δ 2.2 (m, 8H), 2.4 (m, 6H), 2.8 (m, 1H), 6.2 (m, 1H), 7.1 (m, 4H), 7.4 (m, 4H)

Example 87

[3-(4-Bromo-phenyl)-3-tetrazol-2-yl-propyl]-dimethyl-amine

The procedure given in Example 1 was followed using 1-(4-Bromo-phenyl)-ethanone as reactants, instead of 3,4-dichloroacetophenone, to give [3-(4-Bromo-phenyl)-3-tetrazol-2-yl-propyl]-dimethyl-amine.

1H-NMR (CDCl3, 200 MHz) δ 2.2 (m, 10H), 2.4 (m, 1H), 2.8 (m, 1H), 6.2 (m, 1H), 7.3 (m, 2H), 7.5 (m, 2H), 8.5 (s, 1H)

Example 88

[3-(4-Bromo-phenyl)-3-(5-methyl-tetrazol-2-yl)-propyl]-dimethyl-amine

The procedure given in Example 1 was followed using 1-(4-Bromo-phenyl)-ethanone and 5-Me-1H-tetrazole as reactants, instead of 3,4-dichloroacetophenone and 1H-tetrazole, to give [3-(4-Bromo-phenyl)-3-(5-methyl-tetrazol-2-yl)-propyl]-dimethyl-amine.

1H-NMR (CDCl3, 200 MHz) δ 2.2 (m, 9H), 2.3 (m, 1H), 2.5 (s, 3H), 2.8 (m, 1H), 6.0 (m, 1H), 7.3 (m, 2H), 7.5 (m, 2H)

Example 89

Dimethyl-[3-tetrazol-2-yl-3-(4-trifluoromethyl-phenyl)-propyl]-amine

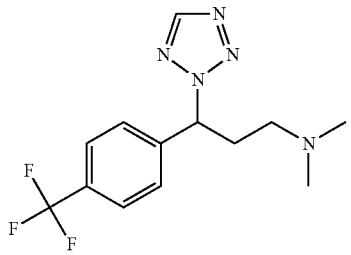 [SMILES: CN(C)CCC(c1ccc(C(F)(F)F)cc1)n1ncnn1]

The procedure given in Example 1 was followed using 1-(4-Trifluoromethyl-phenyl)-ethanone as reactants, instead of 3,4-dichloroacetophenone, to give Dimethyl-[3-tetrazol-2-yl-3-(4-trifluoromethyl-phenyl)-propyl]-amine.

1H-NMR (CDCl3, 200 MHz) δ 2.2 (m, 9H), 2.3 (m, 1H), 2.8 (m, 1H), 6.2 (m, 1H), 7.3 (m, 2H), 7.5 (m, 2H), 8.5 (s, 1H)

Example 90

Dimethyl-[3-(5-methyl-tetrazol-2-yl)-3-(4-trifluoromethyl-phenyl)-propyl]-amine

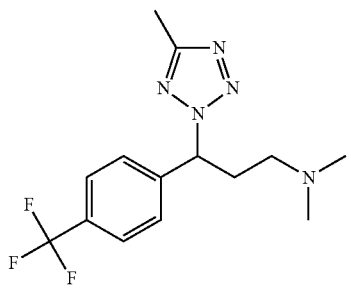 [SMILES: Cc1nnn(C(CCN(C)C)c2ccc(C(F)(F)F)cc2)n1]

The procedure given in Example 1 was followed using 1-(4-Trifluoromethyl-phenyl)-ethanone and 5-Me-1H-tetrazole as reactants, instead of 3,4-dichloroacetophenone and 1H-tetrazole, to give Dimethyl-[3-(5-methyl-tetrazol-2-yl)-3-(4-trifluoromethyl-phenyl)-propyl]-amine.

1H-NMR (CDCl3, 200 MHz) δ 2.2 (m, 9H), 2.3 (m, 1H), 2.5 (s, 3H), 2.8 (m, 1H), 6.0 (m, 1H), 7.6 (m, 4H)

Example 91

Dimethyl-[3-tetrazol-2-yl-3-(2,3,4-trichloro-phenyl)-propyl]-amine

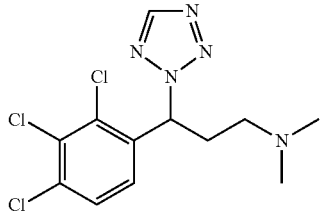 [SMILES: CN(C)CCC(c1ccc(Cl)c(Cl)c1Cl)n1ncnn1]

The procedure given in Example 1 was followed using 1-(2,3,4-Trichloro-phenyl)-ethanone as reactants, instead of 3,4-dichloroacetophenone, to give Dimethyl-[3-tetrazol-2-yl-3-(2,3,4-trichloro-phenyl)-propyl]-amine.

1H-NMR (CDCl3, 200 MHz) δ 2.2 (m, 9H), 2.3 (m, 1H), 2.8 (m, 1H), 6.2 (m, 1H), 7.3 (m, 3H), 8.5 (s, 1H)

Example 92

Dimethyl-[3-(5-methyl-tetrazol-2-yl)-3-(2,3,4-trichloro-phenyl)-propyl]-amine

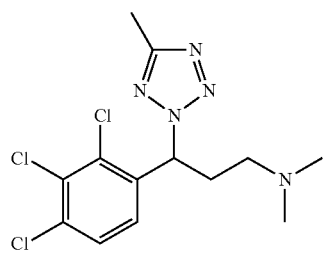 [SMILES: Cc1nnn(C(CCN(C)C)c2ccc(Cl)c(Cl)c2Cl)n1]

The procedure given in Example 1 was followed using 1-(2,3,4-Trichloro-phenyl)-ethanone and 5-Me-1H-tetrazole as reactants, instead of 3,4-dichloroacetophenone and 1H-tetrazole, to give Dimethyl-[3-(5-methyl-tetrazol-2-yl)-3-(2,3,4-trichloro-phenyl)-propyl]-amine.

1H-NMR (CDCl3, 200 MHz) δ 2.2 (m, 9H), 2.3 (m, 1H), 2.5 (s, 3H), 2.8 (m, 1H), 6.0 (m, 1H), 7.2 (m, 2H)

Example 93

[3-(3-Chloro-4-methoxy-phenyl)-3-tetrazol-2-yl-propyl]-dimethyl-amine

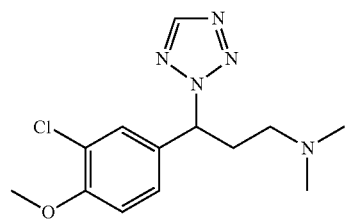

The procedure given in Example 1 was followed using 1-(3-Chloro-4-methoxy-phenyl)-ethanone as reactants, instead of 3,4-dichloroacetophenone, to give [3-(3-Chloro-4-methoxy-phenyl)-3-tetrazol-2-yl-propyl]-dimethyl-amine.

1H-NMR (CDCl3, 200 MHz) δ 2.2 (m, 10H), 2.3 (m, 1H), 2.8 (m, 1H), 4.0 (s, 3H), 6.1 (m, 1H), 6.9 (d, 1H), 7.3 (d, 1H), 7.5 (s, 1H), 8.5 (s, 1H)

Example 94

[3-(3-Chloro-4-methoxy-phenyl)-3-(5-methyl-tetrazol-2-yl)-propyl]-dimethyl-amine

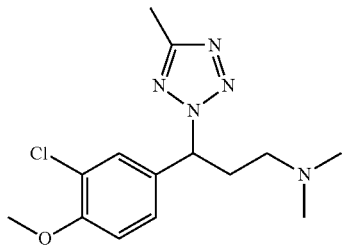

The procedure given in Example 1 was followed using 1-(3-Chloro-4-methoxy-phenyl)-ethanone and 5-Me-1H-tetrazole as reactants, instead of 3,4-dichloroacetophenone and 1H-tetrazole, to give [3-(3-Chloro-4-methoxy-phenyl)-3-(5-methyl-tetrazol-2-yl)-propyl]-dimethyl-amine.

1H-NMR (CDCl3, 200 MHz) δ 2.2 (m, 10H), 2.3 (m, 1H), 2.8 (m, 1H), 4.0 (s, 3H), 6.1 (m, 1H), 6.9 (d, 1H), 7.3 (d, 1H), 7.5 (s, 1H)

Example 95

[3-(4-tert-Butyl-phenyl)-3-(5-methyl-tetrazol-2-yl)-propyl]-dimethyl-amine

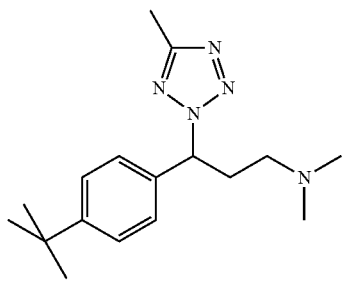 [SMILES: Cc1nnn(C(CCN(C)C)c2ccc(C(C)(C)C)cc2)n1]

The procedure given in Example 1 was followed using 1-(4-tert-Butyl-phenyl)-ethanone and 5-Me-1H-tetrazole as reactants, instead of 3,4-dichloroacetophenone and 1H-tetrazole, to give [3-(4-tert-Butyl-phenyl)-3-(5-methyl-tetrazol-2-yl)-propyl]-dimethyl-amine.

1H-NMR (CDCl3, 200 MHz) δ 1.2 (s, 9H), 2.4 (m, 3H), 2.5 (m, 6H), 2.7 (m, 1H), 6.2 (m, 1H), 7.4 (m, 4H)

Example 96

[3-(2,5-Difluoro-phenyl)-3-(5-methyl-tetrazol-2-yl)-propyl]-dimethyl-amine

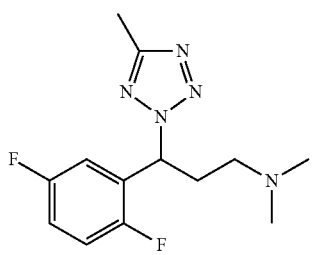 [SMILES: Cc1nnn(C(CCN(C)C)c2cc(F)ccc2F)n1]

The procedure given in Example 1 was followed using 1-(2,5-Difluoro-phenyl)-ethanone and 5-Me-1H-tetrazole as reactants, instead of 3,4-dichloroacetophenone and 1H-tetrazole, to give [3-(2,5-Difluoro-phenyl)-3-(5-methyl-tetrazol-2-yl)-propyl]-dimethyl-amine.

1H-NMR (CDCl3, 200 MHz) δ 2.4 (m, 10H), 2.5 (m, 3H), 2.7 (m, 1H), 6.4 (m, 1H), 7.4 (m, 3H)

Example 97

[3-(2,4-Dichloro-phenyl)-3-(5-methyl-tetrazol-2-yl)-propyl]-dimethyl-amine

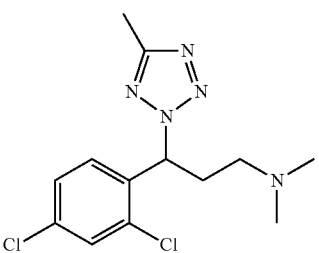 [SMILES: Cc1nnn(C(CCN(C)C)c2ccc(Cl)cc2Cl)n1]

The procedure given in Example 1 was followed using 1-(2,4-Dichloro-phenyl)-ethanone and 5-Me-1H-tetrazole as reactants, instead of 3,4-dichloroacetophenone and 1H-tetrazole, to give [3-(2,4-Dichloro-phenyl)-3-(5-methyl-tetrazol-2-yl)-propyl]-dimethyl-amine.

1H-NMR (CDCl3, 200 MHz) δ 2.4 (m, 10H), 2.5 (m, 3H), 2.7 (m, 1H), 6.4 (m, 1H), 7.4 (m, 3H)

Example 98

[3-(3-Chloro-phenyl)-3-(5-methyl-tetrazol-2-yl)-propyl]-dimethyl-amine

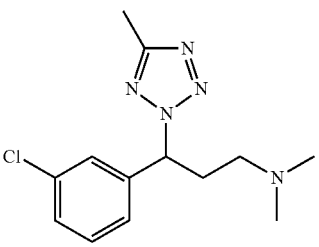 [SMILES: Cc1nnn(C(CCN(C)C)c2cccc(Cl)c2)n1]

The procedure given in Example 1 was followed using 1-(3-Chloro-phenyl)-ethanone and 5-Me-1H-tetrazole as reactants, instead of 3,4-dichloroacetophenone and 1H-tetrazole, to give [3-(3-Chloro-phenyl)-3-(5-methyl-tetrazol-2-yl)-propyl]-dimethyl-amine.

1H-NMR (CDCl3, 200 MHz) δ 2.4 (m, 10H), 2.5 (m, 3H), 2.7 (m, 1H), 6.4 (m, 1H), 7.4 (m, 4H)

Example 99

[3-(2-Chloro-phenyl)-3-(5-methyl-tetrazol-2-yl)-propyl]-dimethyl-amine

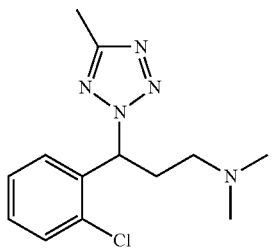 [SMILES: Cc1nnn(C(CCN(C)C)c2ccccc2Cl)n1]

The procedure given in Example 1 was followed using 1-(2-Chloro-phenyl)-ethanone and 5-Me-1H-tetrazole as reactants, instead of 3,4-dichloroacetophenone and 1H-tetrazole, to give [3-(2-Chloro-phenyl)-3-(5-methyl-tetrazol-2-yl)-propyl]-dimethyl-amine.

1H-NMR (CDCl3, 200 MHz) δ 2.4 (m, 10H), 2.5 (m, 3H), 2.7 (m, 1H), 6.4 (m, 1H), 7.4 (m, 4H)

Example 100

[3-(2,5-Difluoro-phenyl)-3-tetrazol-2-yl-propyl]-dimethyl-amine

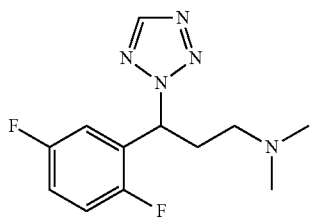 [SMILES: CN(C)CCC(c1cc(F)ccc1F)n1ncnn1]

The procedure given in Example 1 was followed using 1-(2,5-Difluoro-phenyl)-ethanone as reactants, instead of 3,4-dichloroacetophenone, to give [3-(2-5-difluoro-phenyl)-3-tetrazol-2-yl-propyl]-dimethyl-amine 1H-NMR (CDCl3, 200 MHz) δ 2.4 (m, 10H), 2.5 (m, 1H), 2.7 (m, 1H), 6.4 (m, 1H), 7.4 (m, 3H), 8.5 (s, 1H)

Example 101

[3-(2,4-Dichloro-phenyl)-3-tetrazol-2-O-propyl]-dimethyl-amine

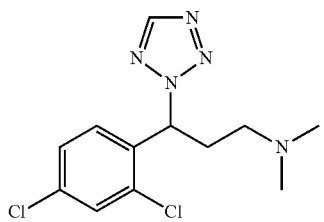 [SMILES: CN(C)CCC(c1ccc(Cl)cc1Cl)n1ncnn1]

The procedure given in Example 1 was followed using 1-(2,4-Dichloro-phenyl)-ethanone as reactants, instead of 3,4-dichloroacetophenone, to give [3-(2,4-dichloro-phenyl)-3-tetrazol-2-yl-propyl]-dimethyl-amine.

1H-NMR (CDCl3, 200 MHz) δ 2.4 (m, 10H), 2.5 (m, 1H), 2.7 (m, 1H), 6.4 (m, 1H), 7.4 (m, 3H), 8.5 (s, 1H)

Example 102

[3-(3-Chloro-phenyl)-3-tetrazol-2-yl-propyl]-dimethyl-amine

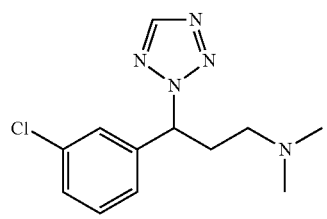 [SMILES: CN(C)CCC(c1cccc(Cl)c1)n1ncnn1]

The procedure given in Example 1 was followed using 1-(3-Chloro-phenyl)-ethanone as reactants, instead of 3,4-dichloroacetophenone, to give [3-(3-Chloro-phenyl)-3-tetrazol-2-yl-propyl]-dimethyl-amine.

1H-NMR (CDCl3, 200 MHz) δ 2.4 (m, 10H), 2.5 (m, 1H), 2.7 (m, 1H), 6.4 (m, 1H), 7.4 (m, 4H), 8.5 (s, 1H)

Example 103

Dimethyl-[3-(5-methyl-tetrazol-2-yl)-3-(4-trifluoromethoxy-phenyl)-propyl]-amine

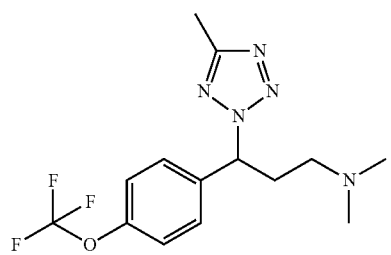 [SMILES: Cc1nnn(C(CCN(C)C)c2ccc(OC(F)(F)F)cc2)n1]

The procedure given in Example 1 was followed using 1-(4-Trifluoromethoxy-phenyl)-ethanone and 5-Me-1H-tetrazole as reactants, instead of 3,4-dichloroacetophenone and 1H-tetrazole, to give Dimethyl-[3-(5-methyl-tetrazol-2-yl)-3-(4-trifluoromethoxy-phenyl)-propyl]-amine.

1H-NMR (CDCl3, 200 MHz) δ 2.4 (m, 10H), 2.5 (m, 3H), 2.7 (m, 1H), 6.4 (m, 1H), 7.2 (m, 2H), 7.4 (m, 2H)

Example 104

[3-(3-Bromo-4-methyl-phenyl)-3-(5-methyl-tetrazol-2-yl)-propyl]-dimethyl-amine

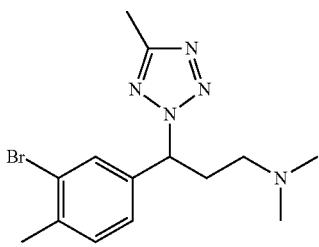

The procedure given in Example 1 was followed using 1-(3-Bromo-4-methyl-phenyl)-ethanone and 5-Me-1H-tetrazole as reactants, instead of 3,4-dichloroacetophenone and 1H-tetrazole, to give [3-(3-Bromo-4-methyl-phenyl)-3-(5-methyl-tetrazol-2-yl)-propyl]-dimethyl-amine.

1H-NMR (CDCl3, 200 MHz) δ 2.4 (m, 10H), 2.5 (m, 3H), 2.7 (m, 1H), 6.4 (m, 1H), 7.4 (m, 3H)

Example 105

Dimethyl-[3-tetrazol-2-yl-3-(4-trifluoromethoxy-phenyl)-propyl]-amine

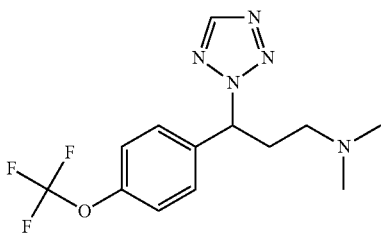 [SMILES: CN(C)CCC(c1ccc(OC(F)(F)F)cc1)n1ncnn1]

The procedure given in Example 1 was followed using 1-(4-Trifluoromethoxy-phenyl)-ethanone as reactants, instead of 3,4-dichloroacetophenone, to give Dimethyl-[3-tetrazol-2-yl-3-(4-trifluoromethoxy-phenyl)-propyl]-amine.

1H-NMR (CDCl3, 200 MHz) δ 2.4 (m, 10H), 2.5 (m, 1H), 2.7 (m, 1H), 6.4 (m, 1H), 7.2 (m, 2H), 7.4 (m, 2H), 8.5 (s, 1H)

Example 106

[3-(4-Bromo-3-methyl-phenyl)-3-tetrazol-2-yl-propyl]-dimethyl-amine

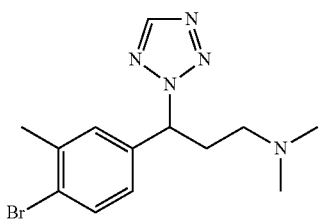

The procedure given in Example 1 was followed using 1-(3-Bromo-4-methyl-phenyl)-ethanone as reactants, instead of 3,4-dichloroacetophenone, to give [3-(4-Bromo-3-methyl-phenyl)-3-tetrazol-2-yl-propyl]-dimethyl-amine.

1H-NMR (CDCl3, 200 MHz) δ 2.4 (m, 10H), 2.5 (m, 1H), 2.7 (m, 1H), 6.4 (m, 1H), 7.4 (m, 3H), 8.5 (s, 1H)

Example 107

[3-(4-Methanesulfonyl-phenyl)-3-(5-methyl-tetrazol-2-yl)-propyl]-dimethyl-amine

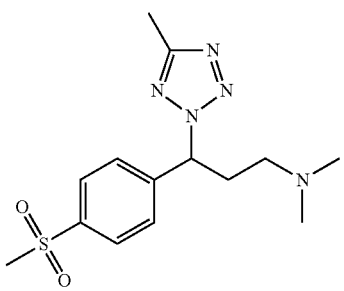

The procedure given in Example 1 was followed using 1-(4-Methanesulfonyl-phenyl)-ethanone and 5-Me-1H-tetrazole as reactants, instead of 3,4-dichloroacetophenone and 1H-tetrazole, to give [3-(4-Methanesulfonyl-phenyl)-3-(5-methyl-tetrazol-2-yl)-propyl]-dimethyl-amine.

1H-NMR (CDCl3, 200 MHz) δ 2.4 (m, 10H), 2.5 (m, 3H), 2.7 (m, 1H), 3.0 (m, 3H), 6.4 (m, 1H), 7.2 (m, 2H), 7.4 (m, 2H)

Example 108

[3-(4-Isopropyl-phenyl)-3-(5-methyl-tetrazol-2-yl)-propyl]-dimethyl-amine

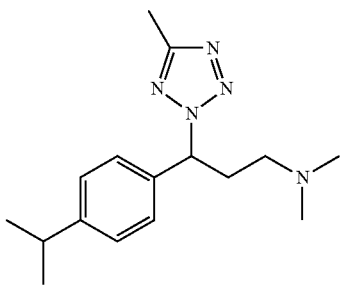 [SMILES: Cc1nnn(C(CCN(C)C)c2ccc(C(C)C)cc2)n1]

The procedure given in Example 1 was followed using 1-(4-Isopropyl-phenyl)-ethanone and 5-Me-1H-tetrazole as reactants, instead of 3,4-dichloroacetophenone and 1H-tetrazole, to give [3-(4-Isopropyl-phenyl)-3-(5-methyl-tetrazol-2-yl)-propyl]-dimethyl-amine.

1H-NMR (CDCl3, 200 MHz) δ 1.0 (s, 6H), 2.4 (m, 10H), 2.7 (m, 1H), 3.0 (m, 3H), 6.4 (m, 1H), 7.2 (m, 2H), 7.4 (m, 2H)

Example 109

[3-(9H-Fluoren-2-yl)-3-(5-methyl-tetrazol-2-yl)-propyl]-dimethyl-amine

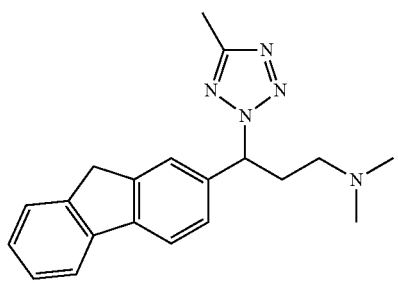 [SMILES: Cc1nnn(C(CCN(C)C)c2ccc3c(c2)Cc2ccccc2-3)n1]

The procedure given in Example 1 was followed using 1-(9H-Fluoren-2-yl)-ethanone and 5-Me-1H-tetrazole as reactants, instead of 3,4-dichloroacetophenone and 1H-tetrazole, to give [3-(9H-Fluoren-2-yl)-3-(5-methyl-tetrazol-2-yl)-propyl]-dimethyl-amine.

1H-NMR (CDCl3, 200 MHz) δ 2.4 (m, 10H), 2.5 (m, 3H), 2.7 (m, 1H), 4.0 (m, 3H), 6.4 (m, 1H), 7.2 (m, 2H), 7.4 (m, 2H)

Example 110

Methyl-(3-naphthalen-2-yl-3-[1,2,3]triazol-2-yl-propyl)-amine

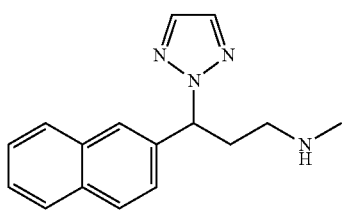

The procedure given in Example 2 was followed using dimethyl-(3-naphthalen-2-yl-3-[1,2,3]triazol-2-yl-propyl)-amine as a reactant, instead of [3-(3,4-Dichloro-phenyl)-3-tetrazol-2-yl-propyl]-dimethyl-amine, to give Methyl-(3-naphthalen-2-yl-3-[1,2,3]triazol-2-yl-propyl)-amine.

1H-NMR (CDCl3, 200 MHz) δ 2.4 (m, 3H), 2.5 (m, 6H), 2.7 (m, 1H), 6.2 (m, 1H), 7.2 (m, 3H) 7.6 (d, 2H), 7.8 (m, 4H)

Example 111

[3-Benzotriazol-2-yl-3-(3,4-dichloro-phenyl)-propyl]-methyl-amine

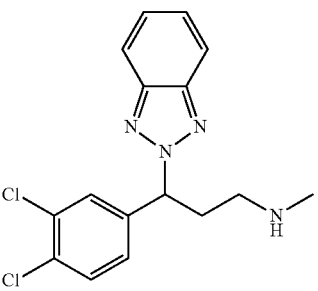

The procedure given in Example 2 was followed using [3-benzotriazol-2-yl-3-(3,4-dichloro-phenyl)-propyl]-dimethyl-amine as a reactant, instead of [3-(3,4-Dichloro-phenyl)-3-tetrazol-2-yl-propyl]-dimethyl-amine, to give [3-Benzotriazol-2-yl-3-(3,4-dichloro-phenyl)-propyl]-methyl-amine.

1H-NMR (CDCl3, 200 MHz) δ 2.4 (m, 3H), 2.5 (m, 3H), 2.7 (m, 1H), 6.2 (m, 1H), 7.2 (m, 4H), 7.6 (s, 1H), 7.9 (m, 2H)

Example 112

Methyl-[3-(5-methyl-tetrazol-2-yl)-3-naphthalen-2-yl-propyl]-amine

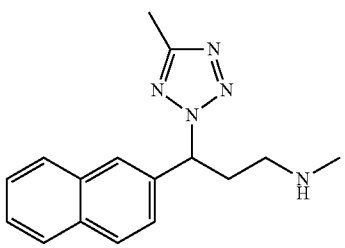 [SMILES: CNCCC(c1ccc2ccccc2c1)n1nnc(C)n1]

The procedure given in Example 2 was followed using [dimethyl-[3-(5-methyl-tetrazol-2-yl)-3-naphthalen-2-yl-propyl]-amine a reactant, instead of [3-(3,4-Dichloro-phenyl)-3-tetrazol-2-yl-propyl]-dimethyl-amine, to give methyl-[3-(5-methyl-tetrazol-2-yl)-3-naphthalen-2-yl-propyl]-amine.

1H-NMR (CDCl3, 200 MHz) δ 2.4 (s, 1H), 2.6 (m, 6H), 2.8 (m, 1H), 6.2 (m, 1H), 7.5 (m, 3H), 7.8 (m, 4H)

Example 113

(3-Benzotriazol-2-yl-3-naphthalen-2-yl-propyl)-methyl-amine

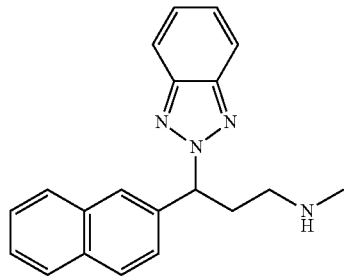 [SMILES: CNCCC(c1ccc2ccccc2c1)n1nc2ccccc2n1]

The procedure given in Example 2 was followed using (3-benzotriazol-2-yl-3-naphthalen-2-yl-propyl)-dimethyl-amine as a reactant, instead of [3-(3,4-dichloro-phenyl)-3-tetrazol-2-yl-propyl]-dimethyl-amine, to give (3-benzotriazol-2-yl-3-naphthalen-2-yl-propyl)-methyl-amine.

1H-NMR (CDCl3, 200 MHz) δ 2.4 (s, 1H), 2.6 (m, 6H), 2.8 (m, 1H), 6.2 (m, 1H), 7.4 (m, 4H), 7.6 (d, 1H), 7.9 (m, 6H)

Example 114

(3-Biphenyl-4-yl-3-tetrazol-2-yl-propyl)-methyl-amine

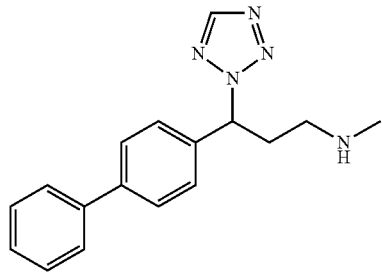 [SMILES: CNCCC(c1ccc(-c2ccccc2)cc1)n1ncnn1]

The procedure given in Example 2 was followed using (3-biphenyl-4-yl-3-tetrazol-2-yl-propyl)-dimethyl-amine as a reactant, instead of [3-(3,4-dichloro-phenyl)-3-tetrazol-2-yl-propyl]-dimethyl-amine, to give (3-Biphenyl-4-yl-3-tetrazol-2-yl-propyl)-methyl-amine.

1H-NMR (CDCl3, 200 MHz) δ 2.4 (s, 1H), 2.6 (m, 6H), 2.8 (m, 1H), 6.2 (m, 1H), 7.4 (m 9H), 8.5 (s, 1H)

Example 115

[3-(3,4-Dichloro-phenyl)-3-(5-methyl-tetrazol-2-yl)-propyl]-methyl-amine

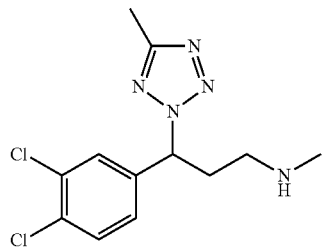

The procedure given in Example 2 was followed using [3-(3,4-dichloro-phenyl)-3-(5-methyl-tetrazol-2-yl)-propyl]-dimethyl-amine as a reactant, instead of [3-(3,4-dichloro-phenyl)-3-tetrazol-2-yl-propyl]-dimethyl-amine, to give [3-(3,4-dichloro-phenyl)-3-(5-methyl-tetrazol-2-yl)-propyl]-methyl-amine.

1H-NMR (CDCl3, 200 MHz) δ 2.4 (m, 3H), 2.5 (m, 6H), 2.7 (m, 1H), 6.2 (m, 1H), 7.2 (m, 1H), 7.4 (m, 1H), 7.5 (s, 1H)

Example 116

[3-(4-Chloro-phenyl)-3-tetrazol-2-yl-propyl]-methyl-amine

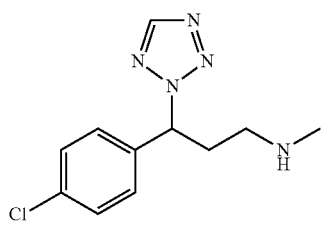 [SMILES: CNCCC(c1ccc(Cl)cc1)n1ncnn1]

The procedure given in Example 2 was followed using [3-(4-chloro-phenyl)-3-tetrazol-2-yl-propyl]-dimethyl-amine as a reactant, instead of [3-(3,4-dichloro-phenyl)-3-tetrazol-2-yl-propyl]-dimethyl-amine, to give [3-(4-chloro-phenyl)-3-tetrazol-2-yl-propyl]methyl-amine.

1H-NMR (CDCl3, 200 MHz) δ 2.4 (m, 3H), 2.5 (m, 6H), 2.7 (m, 1H), 6.2 (m, 1H), 7.3 (m, 4H), 8.5 (s, 1H)

Example 117

[3-(3,4-Dichloro-phenyl)-3-[1,2,3]triazol-2-yl-propyl]-methyl-amine

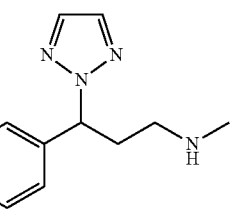

The procedure given in Example 2 was followed using [3-(3,4-dichloro-phenyl)-3-[1,2,3]triazol-2-yl-propyl]-dimethyl-amine as a reactant, instead of [3-(3,4-dichloro-phenyl)-3-tetrazol-2-yl-propyl]-dimethyl-amine, to give [3-(3,4-dichloro-phenyl)-3-[1,2,3]triazol-2-yl-propyl]-methyl-amine.

1H-NMR (CDCl3, 200 MHz) δ 2.4 (m, 3H), 2.5 (m, 3H), 2.7 (m, 1H), 6.2 (m, 1H), 7.2 (m, 1H), 7.4 (m, 1H), 7.5 (s, 1H), 7.6 (d, 2H)

Example 118

[3-(3,4-Dichloro-phenyl)-3-tetrazol-2-yl-propyl]-methyl-amine

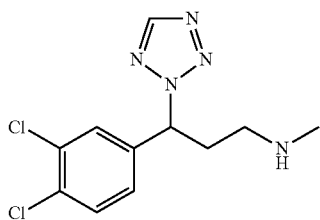

The procedure given in Example 2 was followed using [3-(3,4-dichloro-phenyl)-3-tetrazol-2-yl-propyl]-dimethyl-amine as a reactant, instead of [3-(3,4-dichloro-phenyl)-3-tetrazol-2-yl-propyl]-dimethyl-amine, to give [3-(3,4-dichloro-phenyl)-3-tetrazol-2-yl-propyl]-methyl-amine.

1H-NMR (CDCl3, 200 MHz) δ 2.4 (m, 3H), 2.5 (m, 3H), 2.7 (m, 1H), 6.2 (m, 1H), 7.2 (m, 1H), 7.4 (m, 1H), 7.5 (s, 1H), 8.5 (s, 1H)

Example 119

Methyl-(3-naphthalen-2-yl-3-tetrazol-2-yl-propyl)-amine

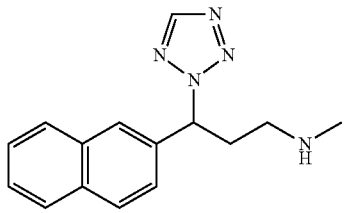

The procedure given in Example 2 was followed using dimethyl-(3-naphthalen-2-yl-3-tetrazol-2-yl-propyl)-amine as a reactant, instead of [3-(3,4-dichloro-phenyl)-3-tetrazol-2-yl-propyl]-dimethyl-amine, to give methyl-(3-naphthalen-2-yl-3-tetrazol-2-yl-propyl)-amine.

1H-NMR (CDCl3, 200 MHz) δ 2.4 (m, 3H), 2.5 (m, 3H), 2.7 (m, 1H), 6.2 (m, 1H), 7.5 (m, 3H), 7.8 (m, 4H), 8.5 (s, 1H)

Example 120

[3-(6-Chloro-naphthalen-2-yl)-3-tetrazol-2-yl-propyl]-methyl-amine

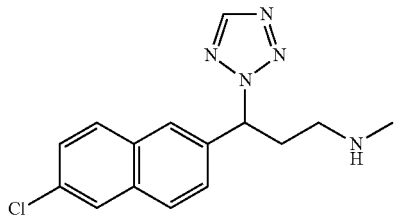 [SMILES: CNCCC(c1ccc2cc(Cl)ccc2c1)n1ncnn1]

The procedure given in Example 2 was followed using [3-(6-chloro-naphthalen-2-yl)-3-tetrazol-2-yl-propyl]-dimethyl-amine as a reactant, instead of [3-(3,4-dichloro-phenyl)-3-tetrazol-2-yl-propyl]-dimethyl-amine, to give [3-(6-Chloro-naphthalen-2-yl)-3-tetrazol-2-yl-propyl]-methyl-amine.

1H-NMR (CDCl3, 200 MHz) δ 2.4 (m, 3H), 2.5 (m, 3H), 2.7 (m, 1H), 7.0 (m, 1H), 7.5 (m, 3H), 7.8 (m, 2H), 8.3 (s, 1H), 8.5 (s, 1H)

Example 121

Methyl-(3-naphthalen-1-yl-3-tetrazol-2-yl-propyl)-amine

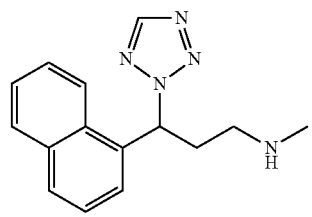 [SMILES: CNCCC(c1cccc2ccccc12)n1ncnn1]

The procedure given in Example 2 was followed using Dimethyl-(3-naphthalen-1-yl-3-tetrazol-2-yl-propyl)-amine as a reactant, instead of [3-(3,4-dichloro-phenyl)-3-tetrazol-2-yl-propyl]-dimethyl-amine, to give methyl-(3-naphthalen-1-yl-3-tetrazol-2-yl-propyl)-amine.

1H-NMR (CDCl3, 200 MHz) δ 2.4 (m, 3H), 2.5 (m, 3H), 2.7 (m, 1H), 7.5 (m, 4H), 7.9 (t, 2H), 8.3 (d, 1H), 8.5 (s, 1H)

Example 122

Methyl-[3-(6-methyl-naphthalen-2-yl)-3-tetrazol-2-yl-propyl]-amine

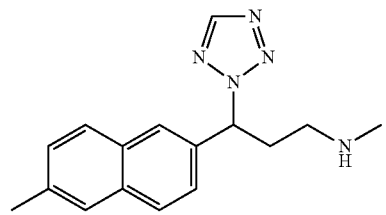

The procedure given in Example 2 was followed using Dimethyl-[3-(6-methyl-naphthalen-2-yl)-3-tetrazol-2-yl-propyl]-amine as a reactant, instead of [3-(3,4-dichloro-phenyl)-3-tetrazol-2-yl-propyl]-dimethyl-amine, to give methyl-[3-(6-methyl-naphthalen-2-yl)-3-tetrazol-2-yl-propyl]-amine 1H-NMR (CDCl3, 200 MHz) δ 2.4 (s, 3H), 2.5 (m, 6H), 2.8 (m, 1H), 6.3 (m, 1H), 7.3 (dd, 1H), 7.5 (m, 2H), 7.7 (dd, 2H), 7.8 (s, 1H), 8.5 (s, 1H)

Example 123

Methyl-[3-naphthalen-2-yl-3-(5-phenyl-tetrazol-2-yl)-propyl]-amine

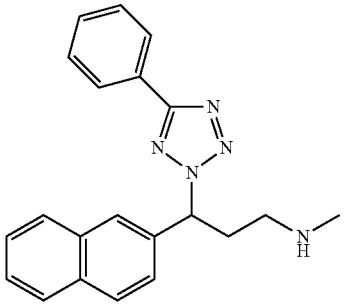 [SMILES: CNCCC(c1ccc2ccccc2c1)n1nnc(-c2ccccc2)n1]

The procedure given in Example 2 was followed using Dimethyl-[3-naphthalen-2-yl-3-(5-phenyl-tetrazol-2-yl)-propyl]-amine as a reactant, instead of [3-(3,4-dichloro-phenyl)-3-tetrazol-2-yl-propyl]-dimethyl-amine, to give methyl-[3-naphthalen-2-yl-3-(5-phenyl-tetrazol-2-yl)-propyl]-amine.

1H-NMR (CDCl3, 200 MHz) δ 2.4 (m, 3H), 2.5 (m, 3H), 2.7 (m, 1H), 6.3 (m, 1H), 7.5 (m, 5H), 7.6 (dd, 1H), 7.8 (m, 3H), 7.9 (s, 1H), 8.2 (m, 2H)

Example 124

(3S)-3-(3,4-dichlorophenyl)-N-methyl-3-(2H-tetrazol-2-yl)propan-1-amine

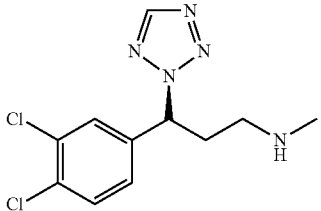

The procedure given in Example 3 was followed using [3-(3,4-Dichloro-phenyl)-3-tetrazol-2-yl-propyl]-methyl-amine, instead of [3-(3,4-Dichloro-phenyl)-3-tetrazol-2-yl-propyl]-methyl-amine, to give (3S)-3-(3,4-Dichloro-phenyl)-3-tetrazol-2-yl-propyl]-methyl-amine.

1H-NMR (CDCl3, 200 MHz) δ 2.4 (m, 3H), 2.5 (m, 3H), 2.7 (m, 1H), 6.2 (m, 1H), 7.2 (m, 1H), 7.4 (m, 1H), 7.5 (s, 1H), 8.5 (s, 1H)

Example 125

(3R)-3-(3,4-dichlorophenyl)-N-methyl-3-(2H-tetrazol-2-yl)propan-1-amine

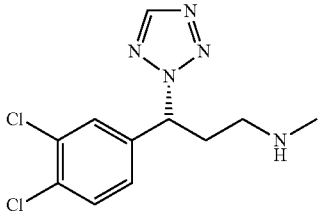

The procedure given in Example 3 was followed using [3-(3,4-Dichloro-phenyl)-3-tetrazol-2-yl-propyl]-methyl-amine, instead of [3-(3,4-Dichloro-phenyl)-3-tetrazol-2-yl-propyl]-methyl-amine, to give 3R-3-(3,4-Dichloro-phenyl)-3-tetrazol-2-yl-propyl]-methyl-amine.

1H-NMR (CDCl3, 200 MHz) δ 2.4 (m, 3H), 2.5 (m, 3H), 2.7 (m, 1H), 6.2 (m, 1H), 7.2 (m, 1H), 7.4 (m, 1H), 7.5 (s, 1H), 8.5 (s, 1H)

Example 126

(3S)-3-(2H-benzotriazol-2-yl)-3-(3,4-dichlorophenyl)-N-methylpropan-1-amine

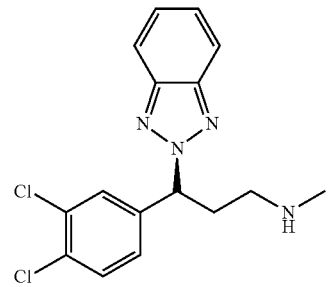

The procedure given in Example 3 was followed using [3-Benzotriazol-2-yl-3-(3,4-dichloro-phenyl)-propyl]-methyl-amine, instead of [3-(3,4-Dichloro-phenyl)-3-tetrazol-2-yl-propyl]-methyl-amine, to give S-[3-Benzotriazol-2-yl-3-(3,4-dichloro-phenyl)-propyl]-methyl-amine.

1H-NMR (CDCl3, 200 MHz) δ 2.4 (m, 3H), 2.5 (m, 3H), 2.7 (m, 1H), 6.2 (m, 1H), 7.2 (m, 4H), 7.6 (s, 1H), 7.9 (m, 2H)

Example 127

(3R)-3-(2H-benzotriazol-2-yl)-3-(3,4-dichlorophenyl)-N-methylpropan-1-amine

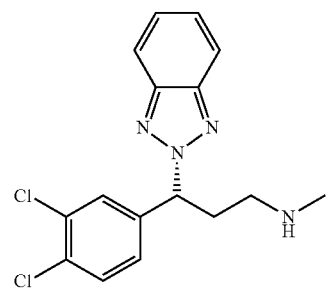

The procedure given in Example 3 was followed using [3-Benzotriazol-2-yl-3-(3,4-dichloro-phenyl)-propyl]-methyl-amine, instead of [3-(3,4-Dichloro-phenyl)-3-tetrazol-2-yl-propyl]-methyl-amine, to give R-[3-Benzotriazol-2-yl-3-(3,4-dichloro-phenyl)-propyl]-methyl-amine.

1H-NMR (CDCl3, 200 MHz) δ 2.4 (m, 3H), 2.5 (m, 3H), 2.7 (m, 1H), 6.2 (m, 1H), 7.2 (m, 4H), 7.6 (s, 1H), 7.9 (m, 2H)

Example 128

(3S)-3-(3,4-dichlorophenyl)-N-methyl-3-(2H-1,2,3-triazol-2-yl)propan-1-amine

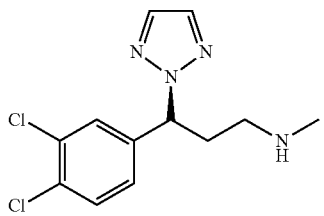

The procedure given in Example 3 was followed using [3-(3,4-Dichloro-phenyl)-3-[1,2,3]triazol-2-yl-propyl]-methyl-amine, instead of [3-(3,4-Dichloro-phenyl)-3-tetrazol-2-yl-propyl]-methyl-amine, to give S-[3-(3,4-Dichloro-phenyl)-3-[1,2,3]triazol-2-yl-propyl]-methyl-amine.

1H-NMR (CDCl3, 200 MHz) δ 2.4 (m, 3H), 2.5 (m, 3H), 2.7 (m, 1H), 6.2 (m, 1H), 7.2 (m, 1H), 7.4 (m, 1H), 7.5 (s, 1H), 7.6 (d, 2H)

Example 129

(3S)-3-(3,4-dichlorophenyl)-N-methyl-3-(5-methyl-2H-tetrazol-2-yl)propan-1-amine

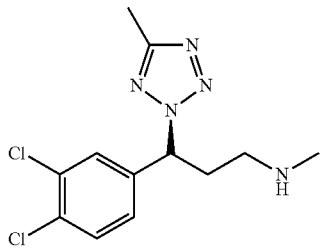

The procedure given in Example 3 was followed using [3-(3,4-Dichloro-phenyl)-3-(4-methyl-[1,2,3]triazol-2-yl)-propyl]-methyl-amine, instead of [3-(3,4-Dichloro-phenyl)-3-tetrazol-2-yl-propyl]-methyl-amine, to give S-[3-(3,4-Dichloro-phenyl)-3-(4-methyl-[1,2,3]triazol-2-yl)-propyl]-methyl-amine.

1H-NMR (CDCl3, 200 MHz) δ 2.4 (m, 3H), 2.5 (m, 6H), 2.7 (m, 1H), 6.2 (m, 1H), 7.2 (m, 1H), 7.4 (m, 1H), 7.5 (s, 1H)

Example 130

(3R)-3-(3,4-dichlorophenyl)-N-methyl-3-(5-methyl-2H-tetrazol-2-yl)propan-1-amine

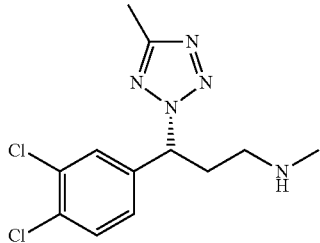

The procedure given in Example 3 was followed using [3-(3,4-Dichloro-phenyl)-3-(4-methyl-[1,2,3]triazol-2-yl)-propyl]-methyl-amine, instead of [3-(3,4-Dichloro-phenyl)-3-tetrazol-2-yl-propyl]-methyl-amine, to give R-[3-(3,4-Dichloro-phenyl)-3-(4-methyl-[1,2,3]triazol-2-yl)-propyl]-methyl-amine.

1H-NMR (CDCl3, 200 MHz) δ 2.4 (m, 3H), 2.5 (m, 6H), 2.7 (m, 1H), 6.2 (m, 1H), 7.2 (m, 1H), 7.4 (m, 1H), 7.5 (s, 1H)

Example 131

(3R)-3-(3,4-dichlorophenyl)-N-methyl-3-(2H-1,2,3-triazol-2-yl)propan-1-amine

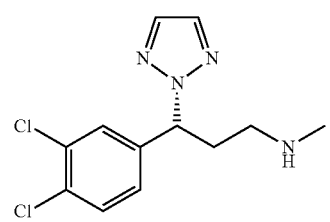

The procedure given in Example 3 was followed using [3-(3,4-Dichloro-phenyl)-3-[1,2,3]triazol-2-yl-propyl]-methyl-amine, instead of [3-(3,4-Dichloro-phenyl)-3-tetrazol-2-yl-propyl]-methyl-amine, to give R-[3-(3,4-Dichloro-phenyl)-3-[1,2,3]triazol-2-yl-propyl]-methyl-amine 1H-NMR (CDCl3, 200 MHz) δ 2.4 (m, 3H), 2.5 (m, 3H), 2.7 (m, 1H), 6.2 (m, 1H), 7.2 (m, 1H), 7.4 (m, 1H), 7.5 (s, 1H), 7.6 (d, 2H)

Example 132

(3R)-N-methyl-3-(2-naphthyl)-3-(2H-tetrazol-2-yl)propan-1-amine

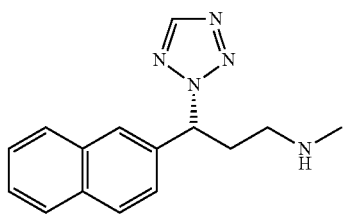

The procedure given in Example 3 was followed using Methyl-(3-naphthalen-2-yl-3-tetrazol-2-yl-propyl)-amine, instead of [3-(3,4-Dichloro-phenyl)-3-tetrazol-2-yl-propyl]-methyl-amine, to give R-Methyl-(3-naphthalen-2-yl-3-tetrazol-2-yl-propyl)-amine.

1H-NMR (CDCl3, 200 MHz) δ 2.4 (m, 3H), 2.5 (m, 3H), 2.7 (m, 1H), 6.2 (m, 1H), 7.5 (m, 3H), 7.8 (m, 4H), 8.5 (s, 1H)

Example 133

(3S)-N-methyl-3-(2-naphthyl)-3-(2H-tetrazol-2-yl)propan-1-amine

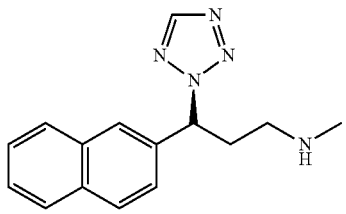

The procedure given in Example 3 was followed using Methyl-(3-naphthalen-2-yl-3-tetrazol-2-yl-propyl)-amine, instead of [3-(3,4-Dichloro-phenyl)-3-tetrazol-2-yl-propyl]-methyl-amine, to give S-Methyl-(3-naphthalen-2-yl-3-tetrazol-2-yl-propyl)-amine 1H-NMR (CDCl3, 200 MHz) δ 2.4 (m, 3H), 2.5 (m, 3H), 2.7 (m, 1H), 6.2 (m, 1H), 7.5 (m, 3H), 7.8 (m, 4H), 8.5 (s, 1H)

Example 134

[3-(3-Methoxy-naphthalen-2-yl)-3-tetrazol-2-yl-propyl]-methyl-amine

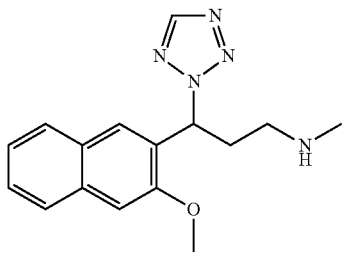

The procedure given in Example 2 was followed using [3-(3-Methoxy-naphthalen-2-yl)-3-tetrazol-2-yl-propyl]-dimethyl-amine as a reactant, instead of [3-(3,4-Dichloro-phenyl)-3-tetrazol-2-yl-propyl]-dimethyl-amine, to give [3-(3-Methoxy-naphthalen-2-yl)-3-tetrazol-2-yl-propyl]-methyl-amine.

1H-NMR (CDCl3, 200 MHz) δ 2.4 (m, 10), 6.2 (m, 1H), 7.5 (m, 3H), 7.8 (m, 4H), 8.5 (s, 1H)

Example 135

[3-(3-Methoxy-naphthalen-2-yl)-3-(5-methyl-tetrazol-2-yl)-propyl]-methyl-amine

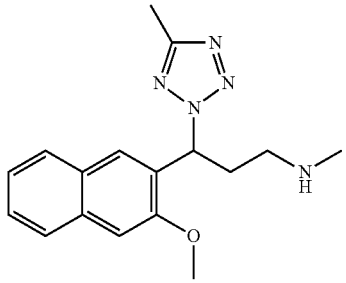

The procedure given in Example 2 was followed using [3-(3-Methoxy-naphthalen-2-yl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(3-Methoxy-naphthalen-2-yl)-3-(5-methyl-tetrazol-2-yl)-propyl]-methyl-amine.

1H-NMR (CDCl3, 200 MHz) δ 2.4 (m, 9H), 2.5 (m, 5H), 2.8 (m, 1H), 4.0 (s, 3H), 6.6 (m, 1H), 7.5 (m, 3H), 7.8 (m, 4H)

Example 136

[3-(6-Fluoro-naphthalen-2-yl)-3-tetrazol-2-yl-propyl]-methyl-amine

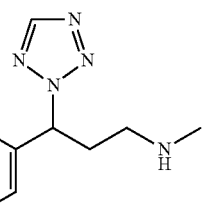

The procedure given in Example 2 was followed using [3-(6-Fluoro-naphthalen-2-yl)-3-tetrazol-2-yl-propyl]-dimethyl-amine as a reactant, instead of [3-(3,4-Dichloro-phenyl)-3-tetrazol-2-yl-propyl]-dimethyl-amine, to give [3-(6-Fluoro-naphthalen-2-yl)-3-tetrazol-2-yl-propyl]-methyl-amine.

1H-NMR (CDCl3, 200 MHz) δ 2.4 (m, 9H), 2.5 (m, 1H), 2.8 (m, 1H), 6.2 (m, 1H), 7.2 (m, 1H), 7.4 (m, 1H), 7.5 (m, 1H), 7.8 (m, 3H), 8.5 (s, 1H)

Example 137

[3-(6-Fluoro-naphthalen-2-yl)-3-(5-methyl-tetrazol-2-yl)-propyl]-methyl-amine

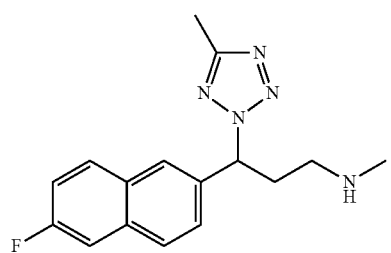

The procedure given in Example 2 was followed using [3-(6-Fluoro-naphthalen-2-yl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(6-Fluoro-naphthalen-2-yl)-3-(5-methyl-tetrazol-2-yl)-propyl]-methyl-amine.

1H-NMR (CDCl3, 200 MHz) δ 2.4 (m, 6H), 2.5 (m, 2H), 2.8 (m, 1H), 6.2 (t, 1H), 7.2 (m, 1H), 7.4 (m, 1H), 7.5 (m, 1H), 7.8 (m, 3H)

Example 138

[3-(1,4-Dimethoxy-naphthalen-2-yl)-3-tetrazol-2-yl-propyl]-methyl-amine

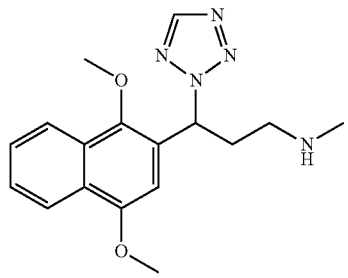 [SMILES: CNCCC(c1cc(OC)c2ccccc2c1OC)n1ncnn1]

The procedure given in Example 2 was followed using [3-(1,4-Dimethoxy-naphthalen-2-yl)-3-tetrazol-2-yl-propyl]-dimethyl-amine as a reactant, instead of [3-(3,4-Dichloro-phenyl)-3-tetrazol-2-yl-propyl]-dimethyl-amine, to give [3-(1,4-Dimethoxy-naphthalen-2-yl)-3-tetrazol-2-yl-propyl]-methyl-amine.

1H-NMR (CDCl3, 200 MHz) δ 2.4 (m, 9H), 2.5 (m, 1H), 2.8 (m, 1H), 4.0 (d, 6H), 6.2 (m, 1H), 7.2 (m, 1H), 7.4 (m, 1H), 7.5 (m, 1H), 7.8 (m, 2H), 8.5 (s, 1H)

Example 139

[3-(1,4-Dimethoxy-naphthalen-2-yl)-3-(5-methyl-tetrazol-2-yl)-propyl]-methyl-amine

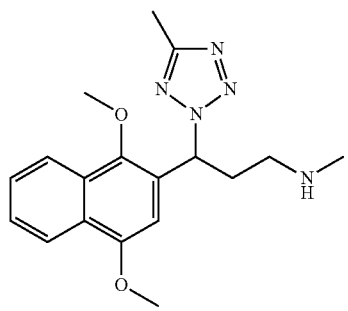 [SMILES: CNCCC(c1cc(OC)c2ccccc2c1OC)n1nnc(C)n1]

The procedure given in Example 2 was followed using [3-(1,4-Dimethoxy-naphthalen-2-yl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(1,4-Dimethoxy-naphthalen-2-yl)-3-(5-methyl-tetrazol-2-yl)-propyl]-methyl-amine.

1H-NMR (CDCl3, 200 MHz) δ 2.4 (m, 9H), 2.5 (m, 1H), 2.8 (m, 1H), 4.0 (d, 6H), 6.2 (m, 1H), 6.9 (s; 1H), 7.5 (m, 2H), 8.0 (s, 1H), 8.2 (d, 1H)

Example 140

[3-(3,5-Dimethoxy-naphthalen-2-yl)-3-tetrazol-2-yl-propyl]-methyl-amine

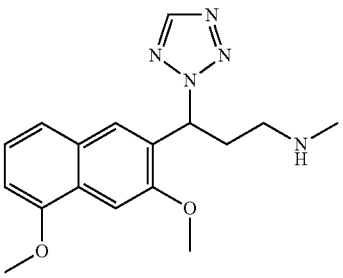 [SMILES: CNCCC(c1cc2cccc(OC)c2cc1OC)n1ncnn1]

The procedure given in Example 2 was followed using [3-(3,5-Dimethoxy-naphthalen-2-yl)-3-tetrazol-2-yl-propyl]-dimethyl-amine as a reactant, instead of [3-(3,4-Dichloro-phenyl)-3-tetrazol-2-yl-propyl]-dimethyl-amine, to give [3-(3,5-Dimethoxy-naphthalen-2-yl)-3-tetrazol-2-yl-propyl]-methyl-amine 1H-NMR (CDCl3, 200 MHz) δ 2.4 (m, 9H), 2.5 (m, 1H), 2.8 (m, 1H), 4.0 (m, 6H), 6.8 (m, 1H), 7.3 (s, 6H), 7.5 (m, 2H), 8.5 (s, 1H)

Example 141

[3-(3,5-Dimethoxy-naphthalen-2-yl)-3-(5-methyl-tetrazol-2-yl)-propyl]-methyl-amine

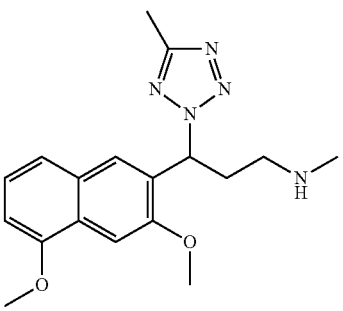 [SMILES: CNCCC(c1cc2cccc(OC)c2cc1OC)n1nnc(C)n1]

The procedure given in Example 2 was followed using [3-(3,5-Dimethoxy-naphthalen-2-yl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(3,5-Dimethoxy-naphthalen-2-yl)-3-(5-methyl-tetrazol-2-yl)-propyl]-methyl-amine.

1H-NMR (CDCl3, 200 MHz) δ 2.0 (s, 6H), 2.4 (m, 6H), 2.5 (m, 2H), 2.8 (m, 1H), 4.0 (m, 6H), 6.6 (m, 1H), 6.8 (m, 1H), 7.2 (s, 3H), 7.7 (d, 2H)

Example 142

[3-(3,5-Dimethoxy-naphthalen-2-yl)-3-tetrazol-1-yl-propyl]-methyl-amine

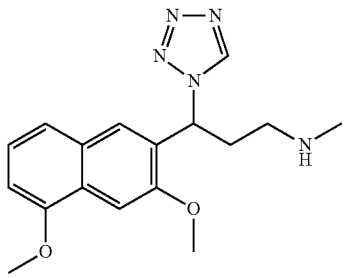 [SMILES: CNCCC(c1cc2cccc(OC)c2cc1OC)n1cnnn1]

The procedure given in Example 2 was followed [3-(3,5-Dimethoxy-naphthalen-2-yl)-3-tetrazol-1-yl-propyl]-dimethyl-amine as a reactant, instead of [3-(3,4-Dichloro-phenyl)-3-tetrazol-2-yl-propyl]-dimethyl-amine, to give [3-(3,5-Dimethoxy-naphthalen-2-yl)-3-tetrazol-1-yl-propyl]-methyl-amine.

1H-NMR (CDCl3, 200 MHz) δ 2.4 (m, 9H), 2.5 (m, 4H), 2.8 (m, 1H), 4.0 (m, 6H), 6.6 (m, 1H), 6.8 (m, 1H), 7.2 (s, 3H), 7.5 (s, 1H), 7.7 (s, 1H), 8.7 (s, 1H)

Example 143

Methyl-[3-(4-methyl-naphthalen-1-yl)-3-tetrazol-2-yl)-propyl]-amine

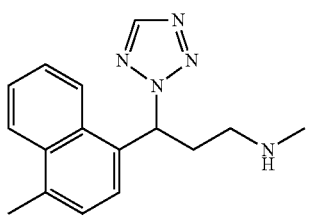 [SMILES: CNCCC(c1ccc(C)c2ccccc12)n1ncnn1]

The procedure given in Example 2 was followed Dimethyl-[3-(4-methyl-naphthalen-1-yl)-3-tetrazol-2-yl-propyl]-amine as a reactant, instead of [3-(3,4-Dichloro-phenyl)-3-tetrazol-2-yl-propyl]-dimethyl-amine, to give Methyl-[3-(4-methyl-naphthalen-1-yl)-3-tetrazol-2-yl-propyl]-amine.

1H-NMR (CDCl3, 200 MHz) δ 2.2 (m, 9H), 2.4 (m, 1H), 2.8 (m, 4H), 3.0 (m, 1H), 7.0 (m, 1H), 7.2 (m, 1H), 7.5 (m, 4H), 8.0 (m, 1H), 8.3 (m, 1H), 8.5 (s, 1H)

Example 144

Methyl-[3-(4-methyl-naphthalen-1-yl)-3-(5-methyl-tetrazol-2-yl)-propyl]-amine

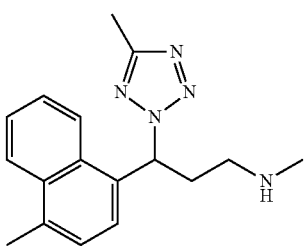 [SMILES: CNCCC(c1ccc(C)c2ccccc12)n1nnc(C)n1]

The procedure given in Example 2 was followed Dimethyl-[3-(4-methyl-naphthalen-1-yl)-3-(5-methyl-tetrazol-2-yl)-propyl]-amine as a reactant, instead of [3-(3,4-Dichloro-phenyl)-3-tetrazol-2-yl-propyl]-dimethyl-amine, to give Methyl-[3-(4-methyl-naphthalen-1-yl)-3-(5-methyl-tetrazol-2-yl)-propyl]-amine.

1H-NMR (CDCl3, 200 MHz) δ 2.2 (m, 6H), 2.4 (m, 3H), 2.8 (m, 3H), 3.0 (m, 1H), 7.0 (m, 1H), 7.2 (m, 1H), 7.5 (m, 4H), 8.0 (m, 1H), 8.3 (m, 1H)

Example 145

[3-(4-Fluoro-naphthalen-1-yl)-3-tetrazol-2-yl-propyl]-methyl-amine

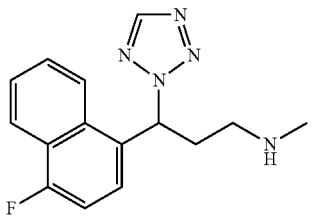

The procedure given in Example 2 was followed [3-(4-Fluoro-naphthalen-1-yl)-3-tetrazol-2-yl-propyl]-dimethyl-amine as a reactant, instead of [3-(3,4-Dichloro-phenyl)-3-tetrazol-2-yl-propyl]-dimethyl-amine, to give [3-(4-Fluoro-naphthalen-1-yl)-3-tetrazol-2-yl-propyl]-methyl-amine 1H-NMR (CDCl3, 200 MHz) δ 2.2 (m, 9H), 2.4 (m, 1H), 2.8 (m, 1H), 7.0 (m, 1H), 7.2 (m, 1H), 7.5 (m, 4H), 8.0 (m, 1H), 8.3 (m, 1H), 8.5 (s, 1H)

Example 146

[3-(4-Fluoro-naphthalen-1-yl)-3-(5-methyl-tetrazol-2-yl)-propyl]-methyl-amine

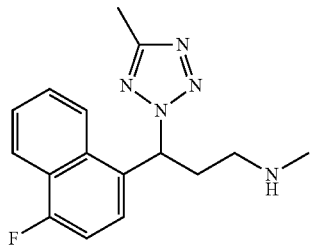 [SMILES: CNCCC(c1ccc(F)c2ccccc12)n1nnc(C)n1]

The procedure given in Example 2 was followed [3-(4-Fluoro-naphthalen-1-yl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(4-Fluoro-naphthalen-1-yl)-3-(5-methyl-tetrazol-2-yl)-propyl]-methyl-amine.

1H-NMR (CDCl3, 200 MHz) δ 2.2 (m, 4H), 2.4 (m, 6H), 2.8 (m, 1H), 7.0 (m, 1H), 7.2 (m, 1H), 7.5 (m, 3H), 8.1 (m, 1H), 8.3 (m, 1H)

Example 147

(3-Benzo[1,3]dioxol-5-yl-3-tetrazol-2-yl-propyl)-methyl-amine

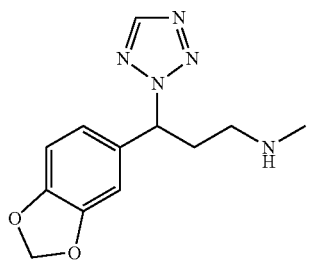

The procedure given in Example 2 was followed (3-Benzo[1,3]dioxol-5-yl-3-tetrazol-2-yl-propyl)-dimethyl-amine as a reactant, instead of [3-(3,4-Dichloro-phenyl)-3-tetrazol-2-yl-propyl]-dimethyl-amine, to give (3-Benzo[1,3]dioxol-5-yl-3-tetrazol-2-yl-propyl)-methyl-amine 1H-NMR (CDCl3, 200 MHz) δ 2.2 (m, 6H), 2.5 (m, 1H), 2.8 (m, 1H), 6.0 (s, 2H), 6.1 (m, 1H), 6.8 (d, 1H), 7.0 (d, 2H), 8.5 (m, 1H)

Example 148

[3-Benzo[1,3]dioxol-5-yl-3-(5-methyl-tetrazol-2-yl)-propyl]-methyl-amine

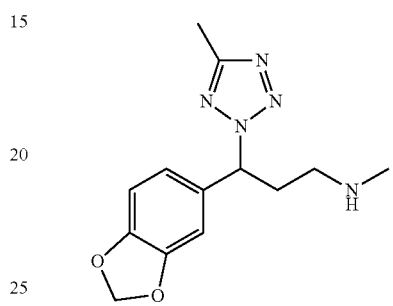

The procedure given in Example 2 was followed [3-Benzo[1,3]dioxol-5-yl-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-Benzo[1,3]dioxol-5-yl-3-(5-methyl-tetrazol-2-yl)-propyl]-methyl-amine.

1H-NMR (CDCl3, 200 MHz) δ 2.2 (m, 12H), 2.8 (m, 1H), 6.0 (s, 2H), 6.1 (m, 1H), 6.8 (d, 1H), 7.0 (d, 2H), 8.5 (m, 1H)

Example 149

[3-Benzo[1,3]dioxol-5-yl-3-(5-methyl-tetrazol-1-yl)-propyl]-methyl-amine

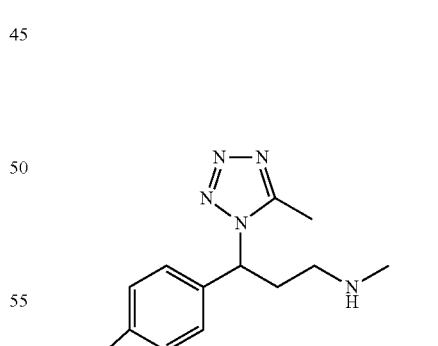

The procedure given in Example 2 was followed [3-Benzo[1,3]dioxol-5-yl-3-(5-methyl-tetrazol-1-yl)-propyl]-dimethyl-amine as a reactant, instead of [3-(3,4-Dichloro-phenyl)-3-tetrazol-2-yl-propyl]-dimethyl-amine, to give [3-Benzo[1,3]dioxol-5-yl-3-(5-methyl-tetrazol-1-yl)-propyl]-methyl-amine.

1H-NMR (CDCl3, 200 MHz) δ 2.2 (m, 6H), 2.4 (m, 1H), 2.5 (s, 3H), 2.8 (m, 1H), 5.5 (t, 2H), 6.1 (s, 2H), 6.8 (m, 3H)

Example 150

[3-(3,4-Dimethoxy-phenyl)-3-tetrazol-2-yl-propyl]-methyl-amine

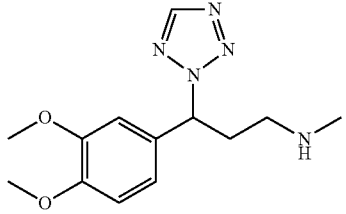

The procedure given in Example 2 was followed [3-(3,4-Dimethoxy-phenyl)-3-tetrazol-2-yl-propyl]-dimethyl-amine as a reactant, instead of [3-(3,4-Dichloro-phenyl)-3-tetrazol-2-yl-propyl]-dimethyl-amine, to give [3-(3,4-Dimethoxy-phenyl)-3-tetrazol-2-yl-propyl]-methyl-amine.

1H-NMR (CDCl3, 200 MHz) δ 2.2 (s, 9H), 2.4 (m, 1H), 2.8 (m, 1H), 4.0 (s, 6H), 6.1 (s, 2H), 6.8 (d, 1H), 7.0 (d, 2H), 8.5 (s, 1H)

Example 151

[3-(2,3-Dihydro-benzo[1,4]dioxin-2-yl)-3-tetrazol-2-yl-propyl]-methyl-amine

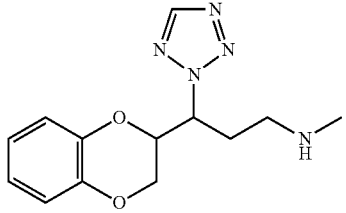

The procedure given in Example 2 was followed [3-(2,3-Dihydro-benzo[1,4]dioxin-2-yl)-3-tetrazol-2-yl-propyl] dimethyl-amine as a reactant, instead of [3-(3,4-Dichloro-phenyl)-3-tetrazol-2-yl-propyl]-dimethyl-amine, to give [3-(2,3-Dihydro-benzo[1,4]dioxin-2-yl)-3-tetrazol-2-yl-propyl]-methyl-amine.

1H-NMR (CDCl3, 200 MHz) δ 2.2 (s, 9H), 2.4 (m, 3H), 3.8 (m, 1H), 4.6 (m, 1H), 5.4 (m, 1H), 7.0 (s, 5H), 8.5 (s, 1H)

Example 152

[3-(2,3-Dihydro-benzo[1,4]dioxin-2-yl)-3-(5-methyl-tetrazol-2-yl)-propyl]-methyl-amine

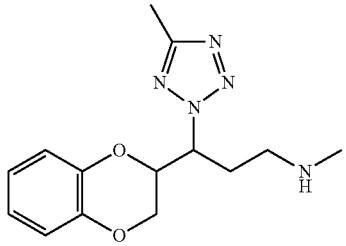 [SMILES: CNCCC(C1COc2ccccc2O1)n1nnc(C)n1]

The procedure given in Example 2 was followed [3-(2,3-Dihydro-benzo[1,4]dioxin-2-yl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(2,3-Dihydro-benzo[1,4]dioxin-2-yl)-3-(5-methyl-tetrazol-2-yl)-propyl]-methyl-amine 1H-NMR (CDCl3, 200 MHz) δ 2.2 (s, 7H), 2.4 (m, 3H), 2.8 (m, 4H), 3.8 (m, 1H), 4.0 (m, 1H), 4.8 (m, 1H), 5.3 (m, 1H), 7.0 (s, 4H)

Example 153

Methyl-[3-(1,2,3,4-tetrahydro-naphthalen-2-yl)-3-tetrazol-2-yl-propyl]-amine

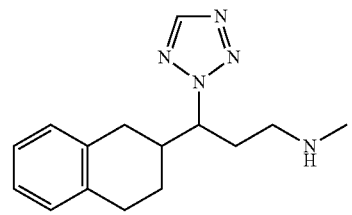 [SMILES: CNCCC(C1CCc2ccccc2C1)n1ncnn1]

The procedure given in Example 2 was followed Dimethyl-[3-(1,2,3,4-tetrahydro-naphthalen-2-yl)-3-tetrazol-2-yl-propyl]-amine as a reactant, instead of [3-(3,4-Dichloro-phenyl)-3-tetrazol-2-yl-propyl]-dimethyl-amine, to give Methyl-[3-(1,2,3,4-tetrahydro-naphthalen-2-yl)-3-tetrazol-2-yl-propyl]-amine.

1H-NMR (CDCl3, 200 MHz) δ 2.2 (s, 8H), 2.8 (m, 8H), 5.0 (m, 1H), 7.0 (m, 4H), 8.5 (s, 1H)

Example 154

[3-(6-Chloro-pyridin-3-yl)-3-tetrazol-2-yl-propyl]-methyl-amine

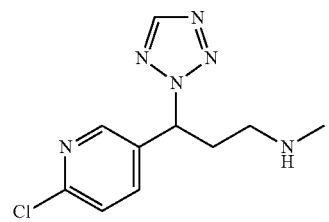 [SMILES: CNCCC(c1ccc(Cl)nc1)n1ncnn1]

The procedure given in Example 2 was followed [3-(6-Chloro-pyridin-3-yl)-3-tetrazol-2-yl-propyl]-dimethyl-amine as a reactant, instead of [3-(3,4-Dichloro-phenyl)-3-tetrazol-2-yl-propyl]-dimethyl-amine, to give [3-(6-Chloro-pyridin-3-yl)-3-tetrazol-2-yl-propyl]-methyl-amine.

1H-NMR (CDCl3, 200 MHz) δ 2.2 (m, 7H), 2.5 (m, 1H), 2.8 (m, 1H), 6.2 (m, 1H), 7.2 (m, 1H), 7.8 (m, 1H), 8.5 (s, 1H)

Example 155

(3-Benzo[b]thiophen-2-yl-3-tetrazol-2-yl-propyl)-methyl-amine

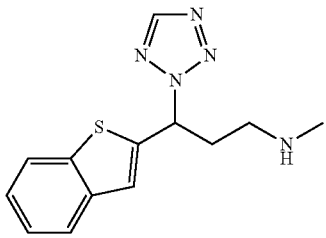

The procedure given in Example 2 was (3-Benzo[b]thiophen-2-yl-3-tetrazol-2-yl-propyl)-dimethyl-amine as a reactant, instead of [3-(3,4-Dichloro-phenyl)-3-tetrazol-2-yl-propyl]-dimethyl-amine, to give (3-Benzo[b]thiophen-2-yl-3-tetrazol-2-yl-propyl)-methyl-amine.

1H-NMR (CDCl3, 200 MHz) δ 2.2 (m, 7H), 2.8 (m, 1H), 6.5 (m, 1H), 7.4 (m, 3H), 7.8 (m, 2H), 8.5 (s, 1H)

Example 156

[3-Benzo[b]thiophen-2-yl-3-(5-methyl-tetrazol-2-yl)-propyl]-methyl-amine

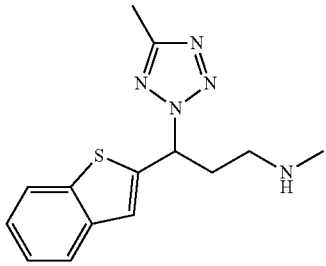

The procedure given in Example 2 was [3-Benzo[b]thiophen-2-yl-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-Benzo[b]thiophen-2-yl-3-(5-methyl-tetrazol-2-yl)-propyl]-methyl-amine.

1H-NMR (CDCl3, 200 MHz) δ 2.2 (m, 6H), 2.8 (m, 5H), 6.5 (m, 1H), 7.4 (m, 3H), 7.8 (m, 2H)

Example 157

(3-Benzofuran-2-yl-3-tetrazol-2-yl-propyl)-methyl-amine

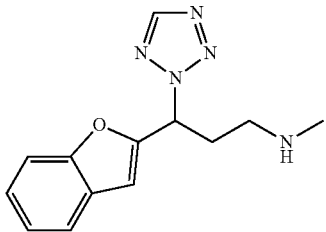 [SMILES: CNCCC(c1cc2ccccc2s1)n1ncnn1]

The procedure given in Example 2 was (3-Benzofuran-2-yl-3-tetrazol-2-yl-propyl)-dimethyl-amine as a reactant, instead of [3-(3,4-Dichloro-phenyl)-3-tetrazol-2-yl-propyl]-dimethyl-amine, to give (3-Benzofuran-2-yl-3-tetrazol-2-yl-propyl)-methyl-amine.

1H-NMR (CDCl3, 200 MHz) δ 2.2 (m, 7H), 2.8 (m, 2H), 6.5 (m, 1H), 7.4 (m, 3H), 7.8 (m, 2H), 8.5 (s, 1H)

Example 158

[3-Benzofuran-2-yl-3-(5-methyl-tetrazol-2-yl)-propyl]-methyl-amine

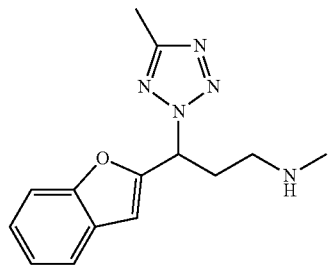

The procedure given in Example 2 was [3-Benzofuran-2-yl-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-Benzofuran-2-yl-3-(5-methyl-tetrazol-2-yl)-propyl]-methyl-amine.

1H-NMR (CDCl3, 200 MHz) δ 2.2 (m, 7H), 2.8 (m, 2H), 6.5 (m, 1H), 7.4 (m, 3H), 7.8 (m, 2H)

Example 159

(3-Benzofuran-2-yl-3-tetrazol-1-yl-propyl)-methyl-amine

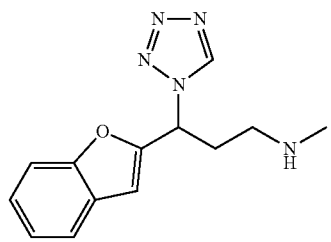 [SMILES: CNCCC(c1cc2ccccc2o1)n1cnnn1]

The procedure given in Example 2 was (3-Benzofuran-2-yl-3-tetrazol-1-yl-propyl)-dimethyl-amine as a reactant, instead of [3-(3,4-Dichloro-phenyl)-3-tetrazol-2-yl-propyl]-dimethyl-amine, to give (3-Benzofuran-2-yl-3-tetrazol-1-yl-propyl)-methyl-amine.

1H-NMR (CDCl3, 200 MHz) δ 2.2 (m, 7H), 2.8 (m, 2H), 6.2 (m, 1H), 7.4 (m, 3H), 7.8 (m, 2H)

Example 160

[3-(3,4-Difluoro-phenyl)-3-tetrazol-2-yl-propyl]-methyl-amine

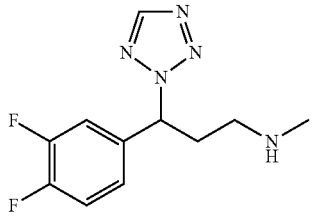 [SMILES: CNCCC(c1ccc(F)c(F)c1)n1ncnn1]

The procedure given in Example 2 was [3-(3,4-Difluoro-phenyl)-3-tetrazol-2-yl-propyl]-dimethyl-amine as a reactant, instead of [3-(3,4-Dichloro-phenyl)-3-tetrazol-2-yl-propyl]-dimethyl-amine, to give [3-(3,4-Difluoro-phenyl)-3-tetrazol-2-yl-propyl]-methyl-amine.

1H-NMR (CDCl3, 200 MHz) δ 2.2 (m, 12H), 6.2 (m, 1H), 7.4 (m, 4H), 8.5 (s, 1H)

Example 161

[3-(3,4-Difluoro-phenyl)-3-(5-methyl-tetrazol-2-yl)-propyl]-methyl-amine

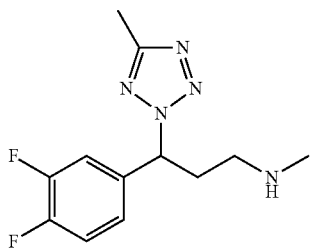 [SMILES: CNCCC(c1ccc(F)c(F)c1)n1nnc(C)n1]

The procedure given in Example 2 was [3-(3,4-Difluoro-phenyl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(3,4-Difluoro-phenyl)-3-(5-methyl-tetrazol-2-yl)-propyl]-methyl-amine.

1H-NMR (CDCl3, 200 MHz) δ 2.2 (m, 7H), 2.8 (m, 4H), 6.2 (m, 1H), 7.4 (m, 4H)

Example 162

Methyl-[3-tetrazol-2-yl-3-(2,4,5-trifluoro-phenyl)-propyl]-amine

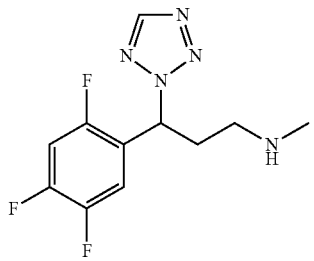 [SMILES: CNCCC(c1cc(F)c(F)cc1F)n1ncnn1]

The procedure given in Example 2 was Dimethyl-[3-tetrazol-2-yl-3-(2,4,5-trifluoro-phenyl)-propyl]-amine as a reactant, instead of [3-(3,4-Dichloro-phenyl)-3-tetrazol-2-yl-propyl]-dimethyl-amine, to give Methyl-[3-tetrazol-2-yl-3-(2,4,5-trifluoro-phenyl)-propyl]-amine.

1H-NMR (CDCl3, 200 MHz) δ 2.2 (m, 9H), 2.8 (m, 2H), 6.5 (m, 1H), 7.0 (m, 1H), 7.4 (m, 1H), 8.6 (s, 1H)

Example 163

Methyl-[3-(5-methyl-tetrazol-2-yl)-3-(2,4,5-trifluoro-phenyl)-propyl]-amine

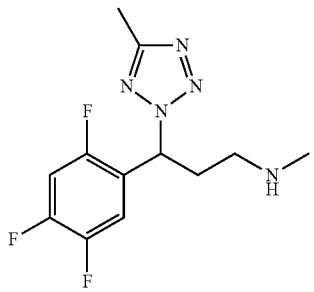 [SMILES: CNCCC(c1cc(F)c(F)cc1F)n1nnc(C)n1]

The procedure given in Example 2 was Dimethyl-[3-(5-methyl-tetrazol-2-yl)-3-(2,4,5-trifluoro-phenyl)-propyl]-amine as a reactant, instead of [3-(3,4-Dichloro-phenyl)-3-tetrazol-2-yl-propyl]-dimethyl-amine, to give Methyl-[3-(5-methyl-tetrazol-2-yl)-3-(2,4,5-trifluoro-phenyl)-propyl]-amine.

1H-NMR (CDCl3, 200 MHz) δ 2.2 (m, 12H), 6.4 (m, 1H), 7.0 (m, 1H), 7.4 (m, 1H)

Example 164

[3-(3-Bromo-4-fluoro-phenyl)-3-tetrazol-2-yl-propyl]-methyl-amine

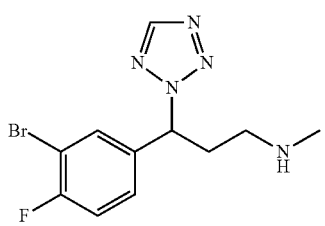

The procedure given in Example 2 was [3-(3-Bromo-4-fluoro-phenyl)-3-tetrazol-2-yl-propyl]-dimethyl-amine as a reactant, instead of [3-(3,4-Dichloro-phenyl)-3-tetrazol-2-yl-propyl]-dimethyl-amine, to give [3-(3-Bromo-4-fluoro-phenyl)-3-tetrazol-2-yl-propyl]-methyl-amine.

1H-NMR (CDCl3, 200 MHz) δ 2.2 (m, 7H), 2.4 (m, 2H), 2.8 (m, 1H), 6.5 (m, 1H), 7.0 (m, 1H), 7.4 (m, 1H), 7.8 (m, 1H), 8.5 (s, 1H)

Example 165

[3-(3-Bromo-4-fluoro-phenyl)-3-(5-methyl-tetrazol-2-yl)-propyl]-methyl-amine

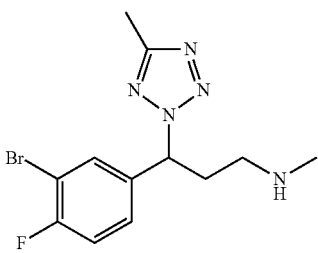

The procedure given in Example 2 was [3-(3-Bromo-4-fluoro-phenyl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(3-Bromo-4-fluoro-phenyl)-3-(5-methyl-tetrazol-2-yl)-propyl]-methyl-amine.

1H-NMR (CDCl3, 200 MHz) δ 2.2 (m, 7H), 2.4 (m, 2H), 2.8 (m, 1H), 6.5 (m, 1H), 7.0 (m, 1H), 7.4 (m, 1H), 7.8 (m, 1H)

Example 166

[3-(6-Methoxy-naphthalen-2-yl)-3-tetrazol-2-yl-propyl]-methyl-amine

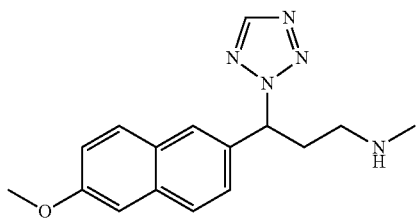

The procedure given in Example 2 was [3-(6-Methoxy-naphthalen-2-yl)-3-tetrazol-2-yl-propyl]-dimethyl-amine as a reactant, instead of [3-(3,4-Dichloro-phenyl)-3-tetrazol-2-yl-propyl]-dimethyl-amine, to give [3-(6-Methoxy-naphthalen-2-yl)-3-tetrazol-2-yl-propyl]-methyl-amine.

1H-NMR (CDCl3, 200 MHz) δ 2.2 (m, 5H), 2.4 (m, 2H), 2.8 (m, 1H), 4.0 (s, 3H), 6.3 (m, 1H), 7.1 (m, 3H), 7.4 (m, 1H), 7.8 (m, 1H), 8.5 (s, 1H)

Example 167

[3-(6-Methoxy-naphthalen-2-yl)-3-(5-methyl-tetrazol-2-yl)-propyl]-methyl-amine

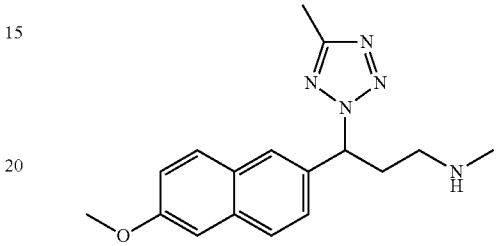

The procedure given in Example 2 was [3-(6-Methoxy-naphthalen-2-yl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(6-Methoxy-naphthalen-2-yl)-3-(5-methyl-tetrazol-2-yl)-propyl]-methyl-amine.

1H-NMR (CDCl3, 200 MHz) δ 2.2 (m, 8H), 2.4 (m, 2H), 2.8 (m, 1H), 4.0 (s, 3H), 6.3 (m, 1H), 7.1 (m, 3H), 7.4 (m, 1H), 7.8 (m, 1H)

Example 168

Methyl-[3-(4-phenoxy-phenyl)-3-tetrazol-2-yl-propyl]-amine

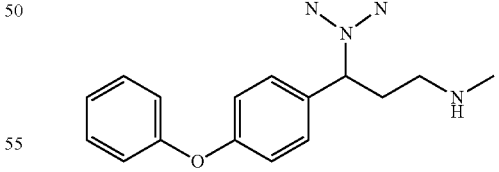

The procedure given in Example 2 was Dimethyl-[3-(4-phenoxy-phenyl)-3-tetrazol-2-yl-propyl]-amine as a reactant, instead of [3-(3,4-Dichloro-phenyl)-3-tetrazol-2-yl-propyl]-dimethyl-amine, to give Methyl-[3-(4-phenoxy-phenyl)-3-tetrazol-2-yl-propyl]amine.

1H-NMR (CDCl3, 200 MHz) δ 2.2 (m, 7H), 2.4 (m, 1H), 2.8 (m, 1H), 6.2 (m, 1H), 7.1 (m, 3H), 7.4 (m, 1H), 7.6 (m, 4H), 8.5 (s, 1H)

Example 169

Methyl-[3-(5-methyl-tetrazol-2-yl)-3-(4-phenoxy-phenyl)-propyl]-amine

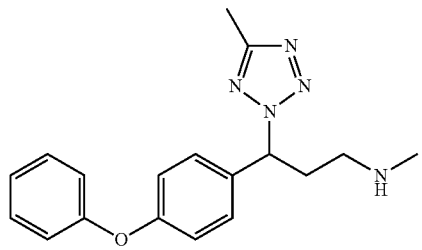 [SMILES: CNCCC(c1ccc(Oc2ccccc2)cc1)n1nnc(C)n1]

The procedure given in Example 2 was Dimethyl-[3-(5-methyl-tetrazol-2-yl)-3-(4-phenoxy-phenyl)-propyl]-amine as a reactant, instead of [3-(3,4-Dichloro-phenyl)-3-tetrazol-2-yl-propyl]-dimethyl-amine, to give Methyl-[3-(5-methyl-tetrazol-2-yl)-3-(4-phenoxy-phenyl)-propyl]-amine.

1H-NMR (CDCl3, 200 MHz) δ 2.2 (m, 5H), 2.4 (m, 6H), 2.8 (m, 1H), 6.2 (m, 1H), 7.1 (m, 4H), 7.4 (m, 4H)

Example 170

[3-(4-Bromo-phenyl)-3-tetrazol-2-yl-propyl]-methyl-amine

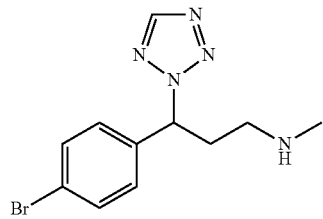

The procedure given in Example 2 was [3-(4-Bromo-phenyl)-3-tetrazol-2-yl-propyl]-dimethyl-amine as a reactant, instead of [3-(3,4-Dichloro-phenyl)-3-tetrazol-2-yl-propyl]-dimethyl-amine, to give [3-(4-Bromo-phenyl)-3-tetrazol-2-yl-propyl]-methyl-amine.

1H-NMR (CDCl3, 200 MHz) δ 2.2 (m, 7H), 2.4 (m, 1H), 2.8 (m, 1H), 6.2 (m, 1H), 7.3 (m, 2H), 7.5 (m, 2H), 8.5 (s, 1H)

Example 171

[3-(4-Bromo-phenyl)-3-(5-methyl-tetrazol-2-yl)-propyl]-methyl-amine

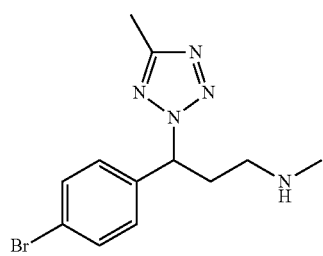 [SMILES: CNCCC(c1ccc(Br)cc1)n1nnc(C)n1]

The procedure given in Example 2 was [3-(4-Bromo-phenyl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(4-Bromo-phenyl)-3-(5-methyl-tetrazol-2-yl)-propyl]-methyl-amine.

1H-NMR (CDCl3, 200 MHz) δ 2.2 (m, 6H), 2.3 (m, 1H), 2.5 (s, 3H), 2.8 (m, 1H), 6.0 (m, 1H), 7.3 (m, 2H), 7.5 (m, 2H)

Example 172

Methyl-[3-tetrazol-2-yl-3-(4-trifluoromethyl-phenyl)-propyl]-amine

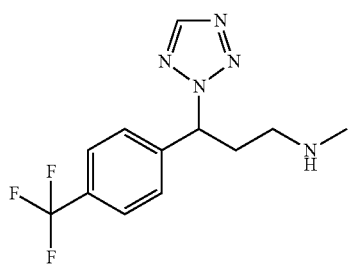 [SMILES: CNCCC(c1ccc(C(F)(F)F)cc1)n1ncnn1]

The procedure given in Example 2 was Dimethyl-[3-tetrazol-2-yl-3-(4-trifluoromethyl-phenyl)-propyl]-amine as a reactant, instead of [3-(3,4-Dichloro-phenyl)-3-tetrazol-2-yl-propyl]-dimethyl-amine, to give Methyl-[3-tetrazol-2-yl-3-(4-trifluoromethyl-phenyl)-propyl]-amine.

1H-NMR (CDCl3, 200 MHz) δ 2.2 (m, 6H), 2.3 (m, 1H), 2.8 (m, 1H), 6.2 (m, 1H), 7.3 (m, 2H), 7.5 (m, 2H), 8.5 (s, 1H)

Example 173

Methyl-[3-(5-methyl-tetrazol-2-yl)-3-(4-trifluoromethyl-phenyl)-propyl]-amine

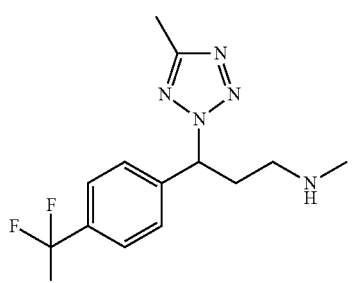

The procedure given in Example 2 was Dimethyl-[3-(5-methyl-tetrazol-2-yl)-3-(4-trifluoromethyl-phenyl)-propyl]-amine as a reactant, instead of [3-(3,4-Dichloro-phenyl)-3-tetrazol-2-yl-propyl]-dimethyl-amine, to give Methyl-[3-(5-methyl-tetrazol-2-yl)-3-(4-trifluoromethyl-phenyl)-propyl]-amine.

1H-NMR (CDCl3, 200 MHz) δ 2.2 (m, 6H), 2.3 (m, 1H), 2.5 (s, 3H), 2.8 (m, 1H), 6.0 (m, 1H), 7.6 (m, 4H)

Example 174

Methyl-[3-tetrazol-2-yl-3-(2,3,4-trichloro-phenyl)-propyl]-amine

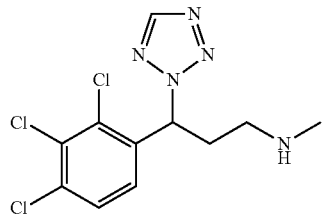 [SMILES: CNCCC(c1ccc(Cl)c(Cl)c1Cl)n1ncnn1]

The procedure given in Example 2 was Dimethyl-[3-tetrazol-2-yl-3-(2,3,4-trichloro-phenyl)-propyl]-amine as a reactant, instead of [3-(3,4-Dichloro-phenyl)-3-tetrazol-2-yl-propyl]-dimethyl-amine, to give Methyl-[3-tetrazol-2-yl-3-(2,3,4-trichloro-phenyl)-propyl]-amine.

1H-NMR (CDCl3, 200 MHz) δ 2.2 (m, 6H), 2.3 (m, 1H), 2.8 (m, 1H), 6.2 (m, 1H), 7.3 (m, 2H), 8.5 (s, 1H)

Example 175

Methyl-[3-(5-methyl-tetrazol-2-yl)-3-(2,3,4-trichloro-phenyl)-propyl]-amine

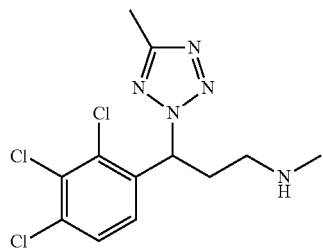 [SMILES: CNCCC(c1ccc(Cl)c(Cl)c1Cl)n1nnc(C)n1]

The procedure given in Example 2 was Dimethyl-[3-(5-methyl-tetrazol-2-yl)-3-(2,3,4-trichloro-phenyl)-propyl]-amine as a reactant, instead of [3-(3,4-Dichloro-phenyl)-3-tetrazol-2-yl-propyl]-dimethyl-amine, to give Methyl-[3-(5-methyl-tetrazol-2-yl)-3-(2,3,4-trichloro-phenyl)-propyl]-amine.

1H-NMR (CDCl3, 200 MHz) δ 2.2 (m, 6H), 2.3 (m, 1H), 2.5 (s, 3H), 2.8 (m, 1H), 6.0 (m, 1H), 7.2 (m, 2H)

Example 176

[3-(3-Chloro-4-methoxy-phenyl)-3-tetrazol-2-yl-propyl]-methyl-amine

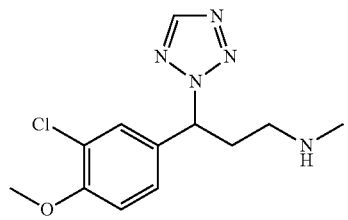

The procedure given in Example 2 was [3-(3-Chloro-4-methoxy-phenyl)-3-tetrazol-2-yl-propyl]-dimethyl-amine as a reactant, instead of [3-(3,4-Dichloro-phenyl)-3-tetrazol-2-yl-propyl]-dimethyl-amine, to give [3-(3-Chloro-4-methoxy-phenyl)-3-tetrazol-2-yl-propyl]-methyl-amine.

1H-NMR (CDCl3, 200 MHz) δ 2.2 (m, 7H), 2.3 (m, 1H), 2.8 (m, 1H), 4.0 (s, 3H), 6.1 (m, 1H), 6.9 (d, 1H), 7.3 (d, 1H), 7.5 (s, 1H), 8.5 (s, 1H)

Example 177

[3-(3-Chloro-4-methoxy-phenyl)-3-(5-methyl-tetrazol-2-yl)-propyl]-methyl-amine

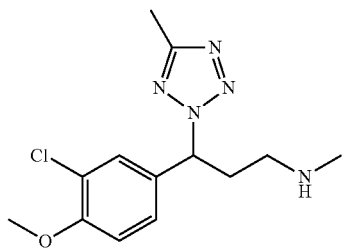

The procedure given in Example 2 was [3-(3-Chloro-4-methoxy-phenyl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(3-Chloro-4-methoxy-phenyl)-3-(5-methyl-tetrazol-2-yl)-propyl]-methyl-amine.

1H-NMR (CDCl3, 200 MHz) δ 2.2 (m, 7H), 2.3 (m, 1H), 2.8 (m, 1H), 4.0 (s, 3H), 6.1 (m, 1H), 6.9 (d, 1H), 7.3 (d, 1H), 7.5 (s, 1H)

Example 178

[3-(2-Chloro-phenyl)-3-(5-methyl-tetrazol-2-yl)-propyl]-methyl-amine

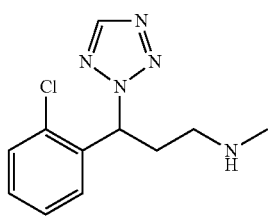 [SMILES: CNCCC(c1ccccc1Cl)n1ncnn1]

The procedure given in Example 2 was [3-(2-Chloro-phenyl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(2-Chloro-phenyl)-3-(5-methyl-tetrazol-2-yl)-propyl]-methyl-amine.

1H-NMR (CDCl3, 200 MHz) δ 2.2 (m, 6H), 2.3 (m, 3H), 2.5 (m, 1H), 2.8 (m, 1H), 7.2 (m, 2H), 7.4 (m, 2H)

Example 179

[3-(3-Chloro-phenyl)-3-(5-methyl-tetrazol-2-yl)-propyl]-methyl-amine

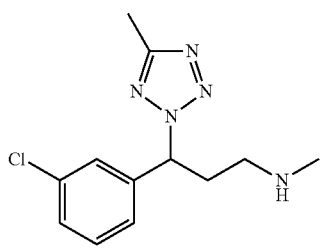 [SMILES: CNCCC(c1cccc(Cl)c1)n1nnc(C)n1]

The procedure given in Example 2 was [3-(3-Chloro-phenyl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(3-Chloro-phenyl)-3-(5-methyl-tetrazol-2-yl)-propyl]-methyl-amine.

1H-NMR (CDCl3, 200 MHz) δ 2.2 (m, 6H), 2.3 (m, 3H), 2.5 (m, 1H), 2.8 (m, 1H), 7.2 (m, 2H), 7.4 (m, 2H)

Example 180

[3-(2,4-Dichloro-phenyl)-3-(5-methyl-tetrazol-2-yl)-propyl]-methyl-amine

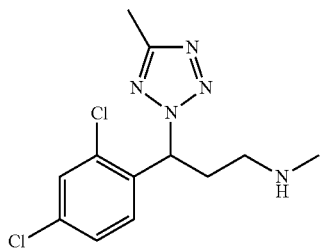 [SMILES: CNCCC(c1ccc(Cl)cc1Cl)n1nnc(C)n1]

The procedure given in Example 2 was [3-(2,4-Dichloro-phenyl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(2,4-Dichloro-phenyl)-3-(5-methyl-tetrazol-2-yl)-propyl]-methyl-amine.

1H-NMR (CDCl3, 200 MHz) δ 2.2 (m, 6H), 2.3 (m, 3H), 2.5 (m, 1H), 2.8 (m, 1H), 7.2 (m, 3H)

Example 181

[3-(2,5-Difluoro-phenyl)-3-(5-methyl-tetrazol-2-yl)-propyl]-methyl-amine

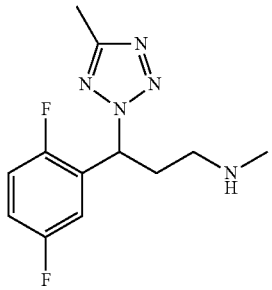 [SMILES: CNCCC(c1cc(F)ccc1F)n1nnc(C)n1]

The procedure given in Example 2 was [3-(2,5-Difluoro-phenyl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(2,5-Difluoro-phenyl)-3-(5-methyl-tetrazol-2-yl)-propyl]-methyl-amine.

1H-NMR (CDCl3, 200 MHz) δ 2.2 (m, 6H), 2.3 (m, 3H), 2.5 (m, 1H), 2.8 (m, 1H), 7.2 (m, 3H)

Example 182

[3-(3-Chloro-phenyl)-3-tetrazol-2-yl-propyl]-methyl-amine

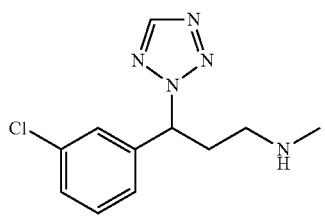 [SMILES: CNCCC(c1cccc(Cl)c1)n1ncnn1]

The procedure given in Example 2 was [3-(3-Chloro-phenyl)-3-tetrazol-2-yl-propyl]-dimethyl-amine as a reactant, instead of [3-(3,4-Dichloro-phenyl)-3-tetrazol-2-yl-propyl]-dimethyl-amine, to give [3-(3-Chloro-phenyl)-3-tetrazol-2-yl-propyl]-methyl-amine 1H-NMR (CDCl3, 200 MHz) δ 2.2 (m, 6H), 2.5 (m, 1H), 2.8 (m, 1H), 7.2 (m, 2H), 7.4 (m, 2H)

Example 183

[3-(2,4-Dichloro-phenyl)-3-tetrazol-2-yl-propyl]-methyl-amine

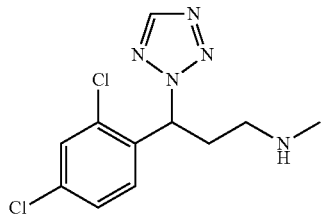 [SMILES: CNCCC(c1ccc(Cl)cc1Cl)n1ncnn1]

The procedure given in Example 2 was [3-(2,4-Dichloro-phenyl)-3-tetrazol-2-yl-propyl]-dimethyl-amine as a reactant, instead of [3-(3,4-Dichloro-phenyl)-3-tetrazol-2-yl-propyl]-dimethyl-amine, to give [3-(2,4-Dichloro-phenyl)-3-tetrazol-2-yl-propyl]-methyl-amine.

1H-NMR (CDCl3, 200 MHz) δ 2.2 (m, 6H), 2.3 (m, 3H), 2.5 (m, 1H), 2.8 (m, 1H), 7.2 (m, 3H)

Example 184

[3-(2,5-Difluoro-phenyl)-3-tetrazol-2-yl)-propyl]-methyl-amine

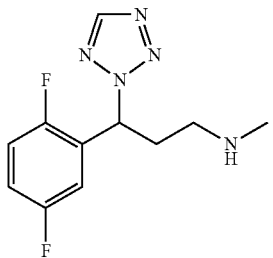 [SMILES: CNCCC(c1cc(F)ccc1F)n1ncnn1]

The procedure given in Example 2 was [3-(2-Chloro-phenyl)-3-tetrazol-2-yl-propyl]-dimethyl-amine as a reactant, instead of [3-(3,4-Dichloro-phenyl)-3-tetrazol-2-yl-propyl]-dimethyl-amine, to give [3-(2,5-Difluoro-phenyl)-3-tetrazol-2-yl-propyl]-methyl-amine.

1H-NMR (CDCl3, 200 MHz) δ 2.2 (m, 6H), 2.3 (m, 3H), 2.5 (m, 1H), 2.8 (m, 1H), 7.2 (m, 3H)

Example 185

[3-(4-Methanesulfonyl-phenyl)-3-(5-methyl-tetrazol-2-yl)-propyl]-methyl-amine

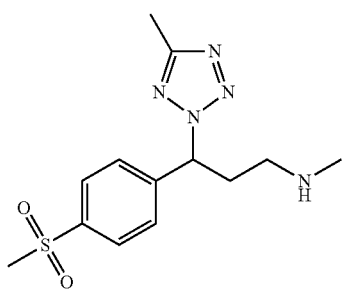

The procedure given in Example 2 was [3-(4-Methanesulfonyl-phenyl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(4-Methanesulfonyl-phenyl)-3-(5-methyl-tetrazol-2-yl)-propyl]-methyl-amine.

1H-NMR (CDCl3, 200 MHz) δ 2.2 (m, 6H), 2.3 (m, 3H), 2.5 (m, 1H), 2.8 (m, 1H), 3.0 (s, 3H), 7.2 (m, 3H)

Example 186

[3-(4-Isopropyl-phenyl)-3-(5-methyl-tetrazol-2-yl)-propyl]-methyl-amine

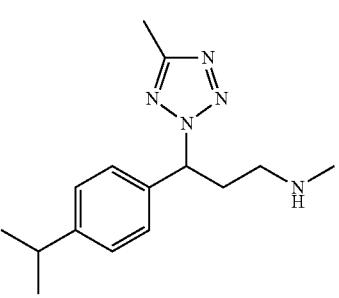 [SMILES: CNCCC(c1ccc(C(C)C)cc1)n1nnc(C)n1]

The procedure given in Example 2 was [3-(4-Isopropyl-phenyl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(4-Isopropyl-phenyl)-3-(5-methyl-tetrazol-2-yl)-propyl]-methyl-amine.

1H-NMR (CDCl3, 200 MHz) δ 2.2 (m, 6H), 2.3 (m, 3H), 2.5 (m, 1H), 2.8 (m, 1H), 4.0 (s, 6H), 7.2 (m, 3H)

Example 187

[3-(9H-Fluoren-2-yl)-3-(5-methyl-tetrazol-2-yl)-propyl]-methyl-amine

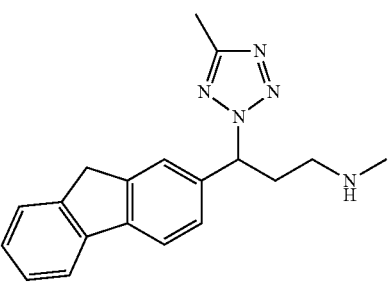 [SMILES: CNCCC(c1ccc2c(c1)Cc1ccccc1-2)n1nnc(C)n1]

The procedure given in Example 2 was [3-(9H-Fluoren-2-yl)-3-(5-methyl-tetrazol-2-yl)-propyl]-dimethyl-amine as a reactant, instead of [3-(3,4-Dichloro-phenyl)-3-tetrazol-2-yl-propyl]-dimethyl-amine, to give [3-(9H-Fluoren-2-yl)-3-(5-methyl-tetrazol-2-yl)-propyl]-methyl-amine.

1H-NMR (CDCl3, 200 MHz) δ 2.2 (m, 6H), 2.3 (m, 3H), 2.5 (m, 1H), 2.8 (m, 1H), 4.2 (s, 2H), 7.2 (m, 3H)

Example 188

(3S)-Methyl-[3-(5-methyl-tetrazol-2-yl)-3-naphthalen-2-yl-propyl]-amine

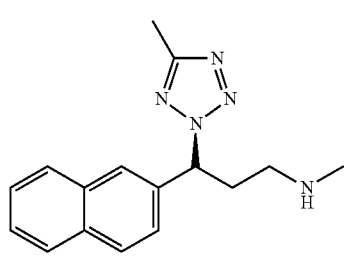

The procedure given in Example 3 was followed using Methyl-[3-(5-methyl-tetrazol-2-yl)-3-naphthalen-2-yl-propyl]-amine, instead of [3-(3,4-Dichloro-phenyl)-3-tetrazol-2-yl-propyl]-methyl-amine, to give (3S)-Methyl-[3-(5-methyl-tetrazol-2-yl)-3-naphthalen-2-yl-propyl]-amine.

1H-NMR (CDCl3, 200 MHz) δ 2.2 (m, 9H), 2.3 (m, 3H), 2.5 (m, 1H), 2.8 (m, 1H), 4.2 (s, 2H), 7.4 (m, 3H), 7.8 (m, 4H)

Example 189

(3S)-Methyl-[3-naphthalen-2-yl-3-(5-phenyl-tetrazol-2-yl)-propyl]-amine

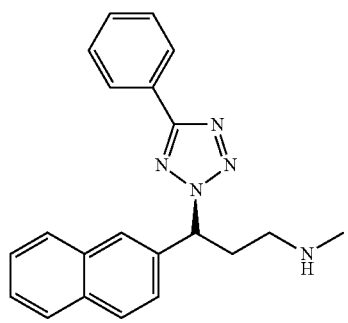

The procedure given in Example 3 was followed using Methyl-[3-naphthalen-2-yl-3-(5-phenyl-tetrazol-2-yl)-propyl]-amine, instead of [3-(3,4-Dichloro-phenyl)-3-tetrazol-2-yl-propyl]-methyl-amine, to give (3S)-Methyl-[3-naphthalen-2-yl-3-(5-phenyl-tetrazol-2-yl)-propyl]-amine.

1H-NMR (CDCl3, 200 MHz) δ 2.2 (m, 9H), 2.3 (m, 3H), 2.5 (m, 1H), 2.8 (m, 1H), 4.2 (s, 2H), 7.4 (m, 10H), 7.8 (m, 4H)

Example 190

(3R)-Methyl-[3-(5-methyl-tetrazol-2-yl)-3-naphthalen-2-yl-propyl]-amine

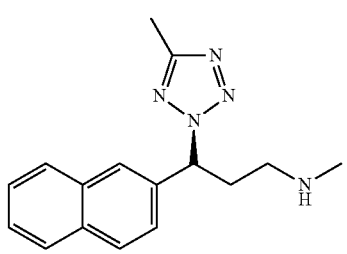

The procedure given in Example 3 was followed using Methyl-[3-(5-methyl-tetrazol-2-yl)-3-naphthalen-2-yl-propyl]-amine, instead of [3-(3,4-Dichloro-phenyl)-3-tetrazol-2-yl-propyl]-methyl-amine, to give (3R)-Methyl-[3-(5-methyl-tetrazol-2-yl)-3-naphthalen-2-yl-propyl]-amine.

1H-NMR (CDCl3, 200 MHz) δ 2.2 (m, 9H), 2.3 (m, 3H), 2.5 (m, 1H), 2.8 (m, 1H), 4.2 (s, 2H), 7.4 (m, 3H), 7.8 (m, 4H)

Example 191

(3R)-Methyl-[3-naphthalen-2-yl-3-(5-phenyl-tetrazol-2-yl)-propyl]-amine

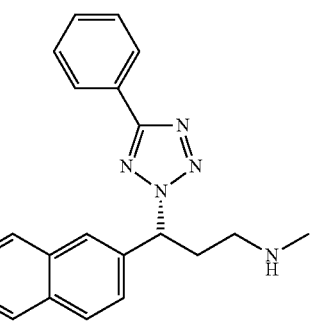

The procedure given in Example 3 was followed using Methyl-[3-naphthalen-2-yl-3-(5-phenyl-tetrazol-2-yl)-propyl]-amine, instead of [3-(3,4-Dichloro-phenyl)-3-tetrazol-2-yl-propyl]-methyl-amine, to give (3R)-Methyl-[3-naphthalen-2-yl-3-(5-phenyl-tetrazol-2-yl)-propyl]-amine.

1H-NMR (CDCl3, 200 MHz) δ 2.2 (m, 9H), 2.3 (m, 3H), 2.5 (m, 1H), 2.8 (m, 1H), 4.2 (s, 2H), 7.4 (m, 10H), 7.8 (m, 4H)

Example 192

(3R)-[3-(6-Fluoro-naphthalen-2-yl)-3-(5-methyl-tetrazol-2-yl)-propyl]-methyl-amine

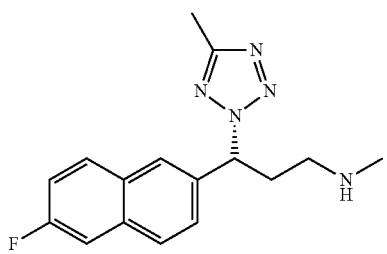

The procedure given in Example 3 was followed using [3-(6-Fluoro-naphthalen-2-yl)-3-(5-methyl-tetrazol-2-yl)-propyl]-methyl-amine, instead of [3-(3,4-Dichloro-phenyl)-3-tetrazol-2-yl-propyl]-methyl-amine, to give (3R)-[3-(6-Fluoro-naphthalen-2-yl)-3-(5-methyl-tetrazol-2-yl)-propyl]-methyl-amine 1H-NMR (CDCl3, 200 MHz) δ 2.2 (m, 9H), 2.3 (m, 3H), 2.5 (m, 1H), 2.8 (m, 1H), 4.2 (s, 2H), 7.4 (m, 3H), 7.8 (m, 4H)

Example 193

(3S)-[3-(6-Fluoro-naphthalen-2-yl)-3-(5-methyl-tetrazol-2-yl)-propyl]-methyl-amine

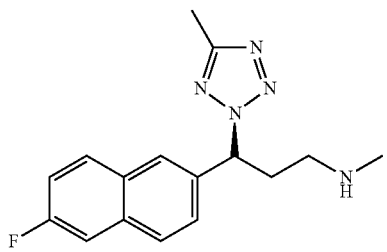

The procedure given in Example 3 was followed using [3-(6-Fluoro-naphthalen-2-yl)-3-(5-methyl-tetrazol-2-yl)-propyl]-methyl-amine, instead of [3-(3,4-Dichloro-phenyl)-3-tetrazol-2-yl-propyl]-methyl-amine, to give (3S)-[3-(6-Fluoro-naphthalen-2-yl)-3-(5-methyl-tetrazol-2-yl)-propyl]-methyl-amine.

1H-NMR (CDCl3, 200 MHz) δ 2.2 (m, 9H), 2.3 (m, 3H), 2.5 (m, 1H), 2.8 (m, 1H), 4.2 (s, 2H), 7.4 (m, 3H), 7.8 (m, 4H)

The therapeutic uses of the racemic or enantiomerically enriched compounds and their pharmaceutically useful salts according to present invention have been established by the following tests.

Serotonin Transporter Reuptake Inhibition Assay

The method to test the ability of compounds to inhibit transporters from reuptake of serotonin followed Gu H. et al., J Biol. Chem., 1994, 269, p 7214~7130.

The recombinant HEK-293 cells with human serotonin transporter were plated. Test compounds described in table 1 were pre-incubated with cells (2×10$^5$/ml) in modified Tris-HEPES buffer pH 7.1 for 20 minutes at 25° C. and then they were incubated for additional 10 minutes after 65 nM of [$^3$H]Serotonin was added. Bound cells were filtered and counted to determine [$^3$H]Serotonin uptake. Reduction of [$^3$H]Serotonin uptake by 50 percent or more (≧50%) relative to 10 μM fluoxetine indicates significant inhibitory activity. Compounds were screened at 10, 1, 0.1, 0.01 and 0.001 μM for IC50s.

Norepinephrine Transporter Reuptake Inhibition Assay

Norepinephrine transporter reuptake inhibition assay used the method described by Galli A. et al., J Exp Biol., 1995, 198, p 2197~2212.

MDCK cells with stably expressed human recombinant norepinephrine transporter were plated one day. Test compounds were pre-incubated with cells (2×10$^5$/ml) in modified Tris-HEPES buffer pH 7.1 for 20 minutes at 25° C. and then they were incubated for additional 10 minutes after 25 nM of [$^3$H]Norepinephrine was added. A lysate was obtained from solubilized cells and the filtered lysate was counted to determine [$^3$H]Norepinephrine uptake. Reduction of [$^3$H]Norepinephrine uptake by 50 percent or more (≧50%) relative to 10 μM desipramine indicates significant inhibitory activity. Compounds were screened at 10, 1, 0.1, 0.01 and 0.001 μM to determine their IC50s.

Dopamine Transporter Reuptake Inhibition Assay

The assay followed the method modified from Pristupa Z. B. et al., Mol. Pharmacol., 1994, p 125~135.

CHO-K1 cells with human recombinant dopamine transporter were plated. Test compounds were pre-incubated with cells (4×10$^5$/ml) in modified Tris-HEPES buffer pH 7.1 for 20 minutes at 25° C. and then they were incubated for additional 10 minutes after 50 nM of [$^3$H]Dopamine was added. A lysate is obtained from solubilized cells and counted to determine [$^3$H]Dopamine uptake. Reduction of [$^3$H]Dopamine uptake by 50 percent or more (≧50%) relative to 10 μM nomifensine indicates significant inhibitory activity. Compounds were tested at 10, 1, 0.1, 0.01 and 0.001 μM for IC50s.

The results obtained by testing compounds of the invention are given in the following table 1:

TABLE 1

| | Inhibition % at 100 nM | | |
|---|---|---|---|
| Test Compound | 5-HT reuptake | NE reuptake | DA reuptake |
| Example 1 | 27% | 37% | 58% |
| Example 2 | 35% | 56% | 48% |
| Example 6 | 41% | 30% | 20% |
| Example 14 | 46% | 32% | 18% |
| Example 21 | 44% | 39% | 36% |
| Example 50 | 61% | 12% | 7% |
| Example 51 | 61% | 10% | 6% |
| Example 119 | 78% | 84% | 10% |
| Example 122 | 93% | 55% | 3% |
| Example 129 | 43% | 84% | 62% |
| Example 135 | 47% | 17% | −1% |
| Example 136 | 59% | 25% | 6% |
| Example 137 | 58% | 39% | 10% |
| Example 166 | 88% | 70% | 4% |
| Example 167 | 82% | 84% | 3% |
| Example 188 | 82% | 79% | 7% |

The data in Table 1 show that racemic or enantiomerically enriched 3-substituted propanamine derivatives, the compounds of the invention have a significantly high inhibition potency of the serotonin, norepinephrine, dopamine transporter reuptake. This inhibition of serotonin, norepinephrine, dopamine transporter reuptake has been associated with the treatment of one or more of the CNS disorders such as depression, anxiety and pain disorder.

Forced Swimming Test in Mice (FST)

The Forced swimming test is an animal model based on the rodent's behavioral repertoire for screening drugs with potential antidepressant activity. As in several other models used for this goal, an uncontrollable stress stimulus produces behavioral changes that are sensitive to antidepressant treatment.

The mice were intraperitoneally treated with the test compound with an injection volume of 10 mg/kg. The group treated with 30% PEG400 served as a control group. Thirty minutes following administration, mice were individually forced to swim in a transparent glass vessel (14 cm high, 11.5 cm in diameter) filled with 10 cm of water at 25° C. The total duration of immobility (second) was measured during the last 4 minutes of a single 6-min test session. Mice were considered immobile when they made no further attempts to escape other than the movements necessary to keep their heads above the water. The potent ability of the compounds was determined as percent value of reduction in the duration of immobility comparing to the control group.

The results obtained by testing compounds of the invention are given in the following table 2:

TABLE 2

| Test Compound | Reduction % at 30ip FST |
|---|---|
| Example 1 | 24.9% |
| Example 2 | 82.4% |
| Example 6 | 41.4% |
| Example 50 | 35.0% |
| Example 51 | 24.5% |
| Example 119 | 43.2% |
| Example 122 | 43.7% |
| Example 129 | 36.7% |
| Example 166 | 28.9% |
| Example 167 | 17.9% |
| Example 188 | 36.7% |

Specially the results of forced swimming test (FST) in mice as noted in Table 2 show the compounds of the invention are related to the treatment of depression.

Marble Burying Test

The Marble burying test is a screening tool for putative anxiolytics. In this test, control mice naturally bury glass marbles in the cage bedding and the administration of anxiolytic compounds, including Diazepam, reduces the number of buried marbles. Positive compounds in the marble burying test including selective serotonin reuptake inhibitor may be especially beneficial to obsessive-compulsive disorder.

A group of mice was intraperitoneally treated with test compound dissolved in 30% PEG400 with an injection volume of 10 ml/kg. The group treated with only 30% PEG400 served as a control group. Thirty minutes after the treatment, the animals were individually placed in a polycarbonate cage which was same as used for animal housing with an open top located within a quiet room. Each cage consisted of ⅛ inch corn bedding 5 cm deep. Twenty four clean glass marbles (15 mm diameter) were evenly spaced in four rows of six on top of the bedding. Each mouse was left in the cage for 30 minutes and the number of marbles buried (buried more than ½ or ⅔) was counted. The potent ability of the compounds was determined as percent value of reduction in the number of marbles buried comparing to the control group.

The results obtained by testing compounds of the invention are given in the following table 3:

TABLE 3

| Test Compound | Reduction % at 30ip |
|---|---|
| Example 1 | 54.8% |
| Example 2 | 100% |
| Example 6 | 87.7% |
| Example 50 | 86.2% |
| Example 51 | 72.4% |
| Example 129 | 94.3% |
| Example 167 | 56.9% (at 10ip) |
| Example 188 | 70.7% |

Specially the results of Marble burying test (MB) in mice as noted in Table 3 show the compounds of the invention are related to the treatment of anxiety.

Acetic Acid Induced Writhing Test (AA Writhing Test)

The Acetic acid-induced writhing test is a well-established nociceptive test using a chemical stimulus. Although several animal models of nociceptive tests have been developed to examine and compare the anti-nociceptive effects of different drugs, the anti-nociceptive effects of antidepressants appear to be test-dependent. Indeed, the acetic acid-induced writhing test is more sensitive to antidepressants than other tests using thermal, mechanical or electrical stimuli.

The animals were subcutaneously treated with the test compound with an injection volume of 10 ml/kg. The group treated with 30% PEG400 or saline served as a control group. Thirty minutes later, the mice were intraperitoneally treated with 0.8% (v/v) acetic acid. Each mouse was then placed in a cage for individual observation. The writhing numbers for 10 minutes were counted. The writhe is operationally defined as a contraction of the abdomen followed by stretching of the hind limbs. The potent ability of the compounds was determined as percent value of reduction in the number of writhing comparing to the control group.

The results obtained by testing compounds of the invention are given in the following table 4:

TABLE 4

| Test Compound | Reduction % at 30sc |
|---|---|
| Example 1 | 55.3% |
| Example 2 | 50.3% |
| Example 6 | 60.2% |
| Example 50 | 53.8% |
| Example 51 | 51.4% |
| Example 129 | 94.4% |
| Example 167 | 52.1% |
| Example 188 | 39.5% |

Specially the results of Acetic acid induced writhing test (AA writhing test) in mice as noted in Table 4 show the compounds of the invention are related to the treatment of pain.

What is claimed is:

1. A method of treating depression, anxiety and pain disorders in a mammal in need of such treatment which comprises administering to said mammal an effective amount of a racemic or enantiomerically enriched 3-substituted propanamine compound represented by the following structural formula (I):

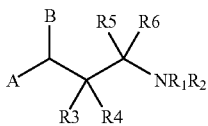

or a pharmaceutically acceptable salt thereof, wherein;
- A is selected from the group consisting of phenyl, naphthyl and benzodioxolyl which can be substituted with one or more identical or different substituents selected from the group consisting of hydrogen, halogen, straight- or branched-chain alkyl of from 1 to 4 carbon atoms, straight- or branched-chain alkoxy of from 1 to 3 carbon atoms, phenyl, phenyloxy, nitro, cyano, trifluoromethyl, trifluoromethoxy, methanesulfonyl and thienyl;
- $R_1$ and $R_2$ are same or different and independently selected from the group consisting of hydrogen, lower alkyl of from 1 to 4 carbon atoms, substituted or unsubstituted phenyl-$C_{1-4}$ alkyl or $R_1$ and $R_2$ are fused with nitrogen atom to form a cyclic group which has 4 to 7 carbon atoms;
- $R_3$, $R_4$, $R_5$ and $R_6$ are same or different and independently selected from the group consisting of hydrogen, lower alkyl of from 1 to 4 carbon atoms and substituted or unsubstituted phenyl;
- B is selected from the group consisting of an azole as represented by the following structural formulae (II):

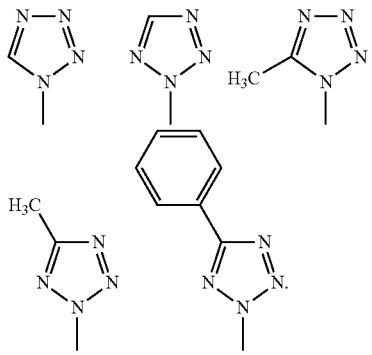

2. A method of treating depression, anxiety and pain disorders in a mammal in need of such treatment which comprises administering to said mammal an effective amount of a racemic or enantiomerically enriched 3-substituted propanamine compound in accordance with claim 1 wherein A, B, $R_1$ and $R_2$ are as defined therein and each of $R_3$ through $R_6$ is hydrogen, said compound being represented by the following structural formula (III):

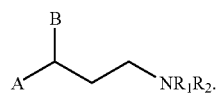

3. A method of treating depression, anxiety and pain disorders in a mammal in need of such treatment which comprises administering to said mammal an effective amount of a racemic or enantiomerically enriched 3-substituted propanamine compound in accordance with claim 1 wherein A and B are as defined therein, each of $R_3$ through $R_6$ is hydrogen and one of $R_1$ and $R_2$ is hydrogen and the other is methyl, said compound being represented by the following structural formula (XI):

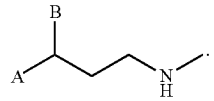

* * * * *